United States Patent
Francais et al.

(10) Patent No.: US 11,787,831 B2
(45) Date of Patent: Oct. 17, 2023

(54) NUCLEOSIDES AND NUCLEOTIDES WITH 3' ACETAL BLOCKING GROUP

(71) Applicant: Illumina Cambridge Limited, Cambridge (GB)

(72) Inventors: Antoine Francais, Cambridge (GB); Elena Cressina, Cambridge (GB); Angelica Mariani, Cambridge (GB); Adam Culley, Cambridge (GB); Anno Koetje, Cambridge (GB); Xiaohai Liu, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 207 days.

(21) Appl. No.: 17/353,512

(22) Filed: Jun. 21, 2021

(65) Prior Publication Data

US 2021/0403500 A1 Dec. 30, 2021

Related U.S. Application Data

(60) Provisional application No. 63/042,240, filed on Jun. 22, 2020.

(51) Int. Cl.
C07H 19/073 (2006.01)
C07H 19/173 (2006.01)
C12Q 1/6869 (2018.01)

(52) U.S. Cl.
CPC ......... *C07H 19/073* (2013.01); *C07H 19/173* (2013.01); *C12Q 1/6869* (2013.01)

(58) Field of Classification Search
None
See application file for complete search history.

(56) References Cited

U.S. PATENT DOCUMENTS

| | | |
|---|---|---|
| 4,772,691 A | 9/1988 | Herman |
| 4,804,748 A | 2/1989 | Seela |
| 5,242,796 A | 9/1993 | Prober et al. |
| 5,302,509 A | 4/1994 | Cheeseman |
| 5,429,807 A | 7/1995 | Matson et al. |
| 5,436,327 A | 7/1995 | Southern et al. |
| 5,547,839 A | 8/1996 | Dower et al. |
| 5,561,071 A | 10/1996 | Hollenberg et al. |
| 5,583,211 A | 12/1996 | Coassin et al. |
| 5,658,734 A | 8/1997 | Brock et al. |
| 5,837,858 A | 11/1998 | Brennan |
| 5,874,219 A | 2/1999 | Rava et al. |
| 5,919,523 A | 7/1999 | Sundberg et al. |
| 6,136,269 A | 10/2000 | Winkler et al. |
| 6,172,218 B1 | 1/2001 | Brenner |
| 6,210,891 B1 | 4/2001 | Nyren et al. |
| 6,232,465 B1 | 5/2001 | Hiatt |
| 6,258,568 B1 | 7/2001 | Nyren |
| 6,274,320 B1 | 8/2001 | Rothberg et al. |
| 6,287,768 B1 | 9/2001 | Chenchik et al. |
| 6,287,776 B1 | 9/2001 | Hefti |
| 6,288,220 B1 | 9/2001 | Kambara et al. |
| 6,291,193 B1 | 9/2001 | Khodadoust |
| 6,297,006 B1 | 10/2001 | Drmanac et al. |
| 6,306,597 B1 | 10/2001 | Macevicz |
| 6,335,155 B1 | 1/2002 | Wells et al. |
| 6,346,413 B1 | 2/2002 | Fodor et al. |
| 6,355,431 B1 | 3/2002 | Chee et al. |
| 6,416,949 B1 | 7/2002 | Dower et al. |
| 6,432,360 B1 | 8/2002 | Church |
| 6,465,178 B2 | 10/2002 | Chappa et al. |
| 6,482,591 B2 | 11/2002 | Lockhart et al. |
| 6,514,751 B2 | 2/2003 | Johann et al. |
| 6,524,793 B1 | 2/2003 | Chandler et al. |
| 6,610,482 B1 | 8/2003 | Fodor et al. |
| 6,664,079 B2 | 12/2003 | Ju et al. |
| 6,969,488 B2 | 11/2005 | Bridgham et al. |
| 7,001,792 B2 | 2/2006 | Sauer et al. |
| 7,057,026 B2 | 6/2006 | Barnes et al. |
| 7,078,499 B2 | 7/2006 | Odedra et al. |
| 7,211,414 B2 | 5/2007 | Hardin et al. |
| 7,270,951 B1 | 9/2007 | Stemple et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,785,796 B2 | 8/2010 | Balasubramanian et al. |
| 8,951,781 B2 | 2/2015 | Williamson et al. |
| 9,222,132 B2 | 12/2015 | Drmanac |
| 2002/0102578 A1 | 8/2002 | Dickinson et al. |

(Continued)

FOREIGN PATENT DOCUMENTS

| | | |
|---|---|---|
| CN | 105315318 | 2/2016 |
| EP | 0 104 857 | 4/1984 |

(Continued)

OTHER PUBLICATIONS

Beckman Coulter CEQ(TM) 2000 DNA Analysis System User's Guide, 606913-AC, dated Jun. 2000.
Boss et al., "Cleavage of Allyl Ethers with Pd/C", Angew. Chem. Int. Ed. Engl., 15:558-559 (1976).
Burns et al., 1991, Selective reduction of disulfides by Tris(2-carboxyethyl)phosphine. J. Org. Chem., 56:2648-2650.
Canard et al., 1994, DNA Polymerase Fluorescent Substrates with Reversible 3'-Tags, Gene, 148:1-6.
Cockroft, 2008, A single-molecule nanopore device detects DNA polymerase activity with single-nucleotide resolution, J. Am. Chem. Soc. 130:818-820.
Deamer, 2000, Nanopores and nucleic acids: prospects for ultrarapid sequencing. Trends Biotechnol. 18:147-151.
Deamer, 2002, Characterization of nucleic acids by nanopore analysis, Acc. Chem. Res. 35:817-825.
Faucher et al., 2003,Tris(2-Carboxyethyl)phosphine (TCEP) for the Reduction of Sulfoxides, Sulfonylchlorides, N-Oxides, and Azides, Synthetic Communications, 33(22):3503-3511.

(Continued)

*Primary Examiner* — Traviss C McIntosh, III
(74) *Attorney, Agent, or Firm* — Knobbe, Martens, Olson & Bear, LLP

(57) ABSTRACT

Embodiments of the present disclosure relate to nucleotide and nucleoside molecules with acetal 3'-OH blocking groups. Also provided herein are methods to prepare such nucleotide and nucleoside molecules, and the uses of fully functionalized nucleotides containing the 3' acetal blocking group for sequencing applications.

36 Claims, 13 Drawing Sheets

(56) References Cited

U.S. PATENT DOCUMENTS

| | | |
|---|---|---|
| 2008/0108082 A1 | 5/2008 | Rank et al. |
| 2009/0026082 A1 | 1/2009 | Rothberg et al. |
| 2009/0088327 A1 | 4/2009 | Rigatti et al. |
| 2009/0118128 A1 | 5/2009 | Liu et al. |
| 2009/0127589 A1 | 5/2009 | Rothberg et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg et al. |
| 2013/0079232 A1 | 3/2013 | Kain et al. |
| 2014/0079923 A1 | 3/2014 | George et al. |
| 2016/0040225 A1 | 2/2016 | Wu et al. |
| 2019/0352327 A1 | 11/2019 | Wu et al. |
| 2020/0131484 A1 | 4/2020 | Golynskiy et al. |
| 2020/0181587 A1 | 6/2020 | Klausing et al. |
| 2020/0216891 A1 | 7/2020 | Francais et al. |
| 2022/0220553 A1 | 7/2022 | Francais et al. |

FOREIGN PATENT DOCUMENTS

| | | | |
|---|---|---|---|
| EP | 0 742 287 | 11/1996 | |
| EP | 0 799 897 | 10/1997 | |
| JP | 59-036696 | 2/1984 | |
| WO | WO 91/06678 | 5/1991 | |
| WO | WO 93/17126 | 9/1993 | |
| WO | WO 95/11995 | 5/1995 | |
| WO | WO 95/35505 | 12/1995 | |
| WO | WO 96/27025 | 9/1996 | |
| WO | WO 98/33939 | 8/1998 | |
| WO | WO 98/44151 | 10/1998 | |
| WO | WO 98/44152 | 10/1998 | |
| WO | WO 98/53300 | 11/1998 | |
| WO | WO 00/06770 | 2/2000 | |
| WO | WO 00/18957 | 4/2000 | |
| WO | WO 00/31148 | 6/2000 | |
| WO | WO 00/53805 | 9/2000 | |
| WO | WO 00/63437 | 10/2000 | |
| WO | WO 01/01143 | 1/2001 | |
| WO | WO 01/57248 | 8/2001 | |
| WO | WO 02/012566 | 2/2002 | |
| WO | WO 02/029003 | 4/2002 | |
| WO | WO 03/014392 | 2/2003 | |
| WO | WO 04/018493 | 3/2004 | |
| WO | WO 04/018497 | 3/2004 | |
| WO | WO-2004018497 A2 * | 3/2004 | .............. C07H 1/00 |
| WO | WO 05/047301 | 5/2005 | |
| WO | WO 05/065814 | 7/2005 | |
| WO | WO 07/010251 | 1/2007 | |
| WO | WO 07/020457 | 2/2007 | |
| WO | WO 07/123744 | 11/2007 | |
| WO | WO 09/054922 | 4/2009 | |
| WO | WO 12/162429 | 11/2012 | |
| WO | WO 14/139596 | 9/2014 | |
| WO | WO 17/079498 | 5/2017 | |
| WO | WO 20/126593 | 6/2020 | |
| WO | WO 00/53812 | 9/2020 | |

OTHER PUBLICATIONS

Genet et al., 1994, Practical palladium-mediated deprotective method of allyloxycarbonyl in aqueous media, Tetrahedron, 50(2):497-503.
Gigg et al., "The Allyl Ether as a Protecting Group in Carbohydrate Chemistry Part II", J. Chem. Soc. (C), 1903-1911 (1968).
Goodwin et al., 2016, Coming of age: ten years of next-generation sequencing technologies, Nat Rev Genet. 17(6):333-351.
Greene & Wuts, 1999, Protective Groups in Organic Synthesis, Third Edition, John Wiley & Sons, New York.
Guillier et al., 2000, Linkers and cleavage strategies in solid-phase organic synthesis and combinatorial chemistry, Chem. Rev. 100:2092-2157.
Healy, 2007, Nanopore-based single-molecule DNA analysis. Nanomed, 2:459-481.
Heidmann et al., 1980, Festphasensynthese von oligonucleotides, 11. Verwendugn eines neuartigen hydrophilen perlpolymerisats als trager, Makromol. Chem and Physics, 181(12):2495-2506.
Jacobs et al., 1994, Combinatorial chemistry—application of light-directed chemical synthesis, Trends Biotech, 12:19-26.
Ju et. al., 2006, Four-color DNA sequencing by synthesis using cleavable fluorescent nucleotide reversible terminators, PNAS USA, 103:19635-40.
Kamal et al., Jul. 28, 1999, A Mild and Rapid Regeneration of Alcohols from their Allylic Ethers by Chlorotrimethyisilane/ Sodium Iodide, Tetrahedron Letters 40:371-372.
Korlach et al., 2008, Selective aluminum passivation for targeted immobilization of single DNA polymerase molecules in zero-mode waveguide nano structures. Proc. Natl. Acad. Sci. USA 105:1176-1181.
Levene et al., 2003, Zero-mode waveguides for single-molecule analysis at high concentrations. Science 299:682-686.
Li et al., 2003, DNA molecules and configurations in a solid-state nanopore microscope, Nat. Mater. 2:611-615.
Loubinoux et al., 1988, Protection of Phenols by the Azidomethylene Group Application to the Synthesis of Unstable Phenols, Tetrahedron 44:6055-6064.
Lundquist et al., 2008, Parallel confocal detection of single molecules in real time. Opt. Lett. 33:1026-1028.
Margulies et al., Sep. 15, 2005, Genome sequencing in microfabricated high-density picolitre reactors, Nature, 437:376-380.
Matsumoto et al., 1968, A Revised Structure of Pederin, 60 Tetrahedron Letters, 60:6297-6300.
Meinwald, 1977, An Approach to the Synthesis of Pederin, Pure and Appl. Chem., vol. 49, Pergoamon Press, pp. 1275-1290.
Metzker et al., 1994, Termination of DNA synthesis by novel 3'-modified-deoxyribonucleoside 5'-triphosphates, Nucleic Acids Research, 22(20):4259-4267.
Metzker et al., 2005, Emerging technologies in DNA sequencing, Genome Research, 15:1767-1776.
Mukaiyama et al. 1996, Catalytic stereoselective synthesis of pyrimidine 2-deoxyribonucleosides, Chemistry Letters, 56(2):99-100.
Peter G. M. Wuts, 2007, Preface to the Fourth Edition, in Greene's Protective Groups in Organic Synthesis, Greene & Wuts (Eds.), Hoboken, NJ: John Wiley & Sons.
Prestat et al. 2000, Synthesis of 3'-$O^2$-(azaheterocycle)-thymidines, Nucleosides, Nucleotides & Nucleic Acids 19(4):735-748.
Prober et al., Oct. 16, 1987, A System for Rapid DNA Sequencing with Fluorescent Chain-Terminating Dideoxynucleotides, Science, 238:336-341.
Qian et al., "Chemoenzymatic synthesis of α-(1→3)-Gal(NAc) terminating glycosides of complex tertiary sugar alcohols," J. Am. Chem. Soc. 121:12063-12072 (1999).
Qian et al., "Unexpected Enzymatic Fucosylation of the Hindered Tertiary Alcohol of 3-C-Methyl-N-Acetyllactosamine Produces a Novel Analogue of the LeX-Trisaccharide", Journal of the American Chemical Society, 120:2184-2185 (1998).
Qian, "Enzymatic and Chemical Synthesis of Oligosaccharide Analogs," Thesis, University of Alberta (2000).
Ronaghi et al., 1998, A sequencing method based on real-time pyrophosphate, Science 281(5375):363-365.
Ronaghi et al., 1996, Real-time DNA sequencing using detection of pyrophosphate release, Analytical Biochemistry, 242(1):84-89.
Ronaghi, 2001, Pyrosequencing sheds light on DNA sequencing, Genome Res. 11(1):3-11.
Ruby et al., 1990, Affinity Chromatography with Biotynlated RNAs, Methods in Enxymology, 181:97-121.
Scheit, Nucleotide Analogs: Synthesis and Biological Function, John Wiley & Son, New York, 1980.
Shendure et al., Sep. 9, 2005, Accurate multiplex polony sequencing of an evolved bacterial genome, Science, 309:1728-1732.
Soni et al., 2007, Progress toward ultrafast DNA sequencing using solid-state nanopores, Clin. Chem. 53:1996-2001.
Stimpson et al., 1995, Real-time detection of DNA hybridization and melting on oligonucleotide arrays by using optical wave guides, Proc. Natl. Acad. Sci. 92:6379-6383.
Ulhman et al., Jun. 1990, Antisense oligonucleotides: a new therapeutic principle, Chemical Reviews, 90(4):543-584.
Welch et al., "Syntheses of Nucleosides Designed for Combinatorial DNA Sequencing", Chem. Eur. J., 5:951-960 (1999).

(56) References Cited

OTHER PUBLICATIONS

Yamashita et al., 1987, Studies on antitumor agents. VII. Antitumor activities of O-alkoxyalkyl derivatives of 2'-deoxy-5-trifluoromethyluridine, Chemical and Pharmaceutical Bulletin, 35(6):2373-2381.

Young, A Strategy for the Synthesis of Sulfated Peptides, A dissertation submitted in partial fulfillment of the requirements for the degree of Doctor of Philosophy (Chemistry) at the University of Wisconsin-Madison (2001).

Zavgorodny et al., 1991, 1-Alkylthioalkylation of Nucleoside Hydroxyl Functions and its Synthetic Applications, Tetrahedron Letters, 32(51):7593-7596.

Zavgorodny et al., 2000, S,X-Acetals in Nucleoside Chemistry III. Synthesis of 2' and 3'-O-Azidomethyl Derivatives of Ribonucleosides, Nucleosides, Nucleotides & Nucleic Acids, 19(10-12):1977-1991.

International Search Report and Written Opinion dated Oct. 14, 2021 in application No. PCT/EP2021/066886.

Bentley et al., Nov. 6, 2008, Accurate whole human genome sequencing using reversible terminator chemistry, Nature, 456:53-59 and supplementary information.

Bi et al., 2006, Design and synthesis of a chemically cleavable fluorescent nucleotide, 3'-O-allyl-dGTP-allyl-Bodipy-FL-510, as a reversible terminator for DNA sequencing by synthesis, JACS, 128:2542-2543.

Guo et al., Apr. 20, 2010, An integrated system for DNA sequencing by synthesis using novel nucleotide analogues, Acc Chem Res., 43(4):551-563.

Guo et al., Jul. 8, 2008, Four-color DNA sequencing with 3'-O-modified nucleotide reversible terminators and chemically cleavable fluorescent dideoxynucleotides, PNAS, 105(27):9145-9150.

Hovinen et al., 1994, Synthesis of 3'-O-(ω-aminoalkoxymethyl)thymidine 5'-triphosphates, terminator of DNA synthesis that enable 3'-labelling, J. Chem. Soc. Perkin Trans, pp. 211-217.

Metzker, Jan. 2010, Sequencing technologies—the next generation, Nature Reviews Genetics, 11:31-46.

Wu et al., Oct. 16, 2007, 3'-O-modified nucleotides as reversible terminators for pyrosequencing, PNAS, 104(42):16462-16467.

\* cited by examiner

NUCLEOSIDES AND NUCLEOTIDES WITH 3' ACETAL BLOCKING GROUP

INCORPORATION BY REFERENCE TO PRIORITY APPLICATIONS

The present application claims the benefit of priority to U.S. Provisional Application No. 63/042,240, filed Jun. 22, 2020, which is incorporated by reference in its entirety.

BACKGROUND

Field

The present disclosure generally relates to nucleotides, nucleosides, or oligonucleotides comprising 3' acetal blocking group and their use in polynucleotide sequencing methods. Methods of preparing the 3' blocked nucleotides, nucleosides, or oligonucleotides are also disclosed.

Description of the Related Art

Advances in the study of molecules have been led, in part, by improvement in technologies used to characterize the molecules or their biological reactions. In particular, the study of the nucleic acids DNA and RNA has benefited from developing technologies used for sequence analysis and the study of hybridization events.

An example of the technologies that have improved the study of nucleic acids is the development of fabricated arrays of immobilized nucleic acids. These arrays consist typically of a high-density matrix of polynucleotides immobilized onto a solid support material. See, e.g., Fodor et al., *Trends Biotech.* 12: 19-26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., *Proc. Natl. Acad. Sci.* 92: 6379-6383, 1995).

One way of determining the nucleotide sequence of a nucleic acid bound to an array is called "sequencing by synthesis" or "SBS". This technique for determining the sequence of DNA ideally requires the controlled (i.e., one at a time) incorporation of the correct complementary nucleotide opposite the nucleic acid being sequenced. This allows for accurate sequencing by adding nucleotides in multiple cycles as each nucleotide residue is sequenced one at a time, thus preventing an uncontrolled series of incorporations from occurring. The incorporated nucleotide is read using an appropriate label attached thereto before removal of the label moiety and the subsequent next round of sequencing.

In order to ensure that only a single incorporation occurs, a structural modification ("protecting group" or "blocking group") is included in each labeled nucleotide that is added to the growing chain to ensure that only one nucleotide is incorporated. After the nucleotide with the protecting group has been added, the protecting group is then removed, under reaction conditions which do not interfere with the integrity of the DNA being sequenced. The sequencing cycle can then continue with the incorporation of the next protected, labeled nucleotide.

To be useful in DNA sequencing, nucleotides, which are usually nucleotide triphosphates, generally require a 3'-hydroxy protecting group so as to prevent the polymerase used to incorporate it into a polynucleotide chain from continuing to replicate once the base on the nucleotide is added. There are many limitations on the types of groups that can be added onto a nucleotide and still be suitable. The protecting group should prevent additional nucleotide molecules from being added to the polynucleotide chain whilst simultaneously being easily removable from the sugar moiety without causing damage to the polynucleotide chain. Furthermore, the modified nucleotide needs to be compatible with the polymerase or another appropriate enzyme used to incorporate it into the polynucleotide chain. The ideal protecting group must therefore exhibit long-term stability, be efficiently incorporated by the polymerase enzyme, cause blocking of secondary or further nucleotide incorporation, and have the ability to be removed under mild conditions that do not cause damage to the polynucleotide structure, preferably under aqueous conditions.

Reversible protecting groups have been described previously. For example, Metzker et al., (*Nucleic Acids Research*, 22 (20): 4259-4267, 1994) discloses the synthesis and use of eight 3'-modified 2-deoxyribonucleoside 5'-triphosphates (3'-modified dNTPs) and testing in two DNA template assays for incorporation activity. WO 2002/029003 describes a sequencing method which may include the use of an allyl protecting group to cap the 3'-OH group on a growing strand of DNA in a polymerase reaction.

In addition, the development of a number of reversible protecting groups and methods of deprotecting them under DNA compatible conditions was previously reported in International Application Publication Nos. WO 2004/018497 and WO 2014/139596, each of which is hereby incorporated by reference in its entirety.

SUMMARY

Some embodiments of the present disclosure relate to a nucleotide or nucleoside comprising a nucleobase attached to a detectable label via a cleavable linker, wherein the nucleoside or nucleotide comprises a ribose or 2' deoxyribose moiety and a 3'-OH blocking group, and wherein the cleavable linker comprises a moiety of the structure:

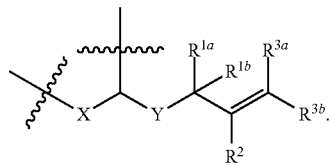

wherein each of X and Y is independently O or S; and each of $R^{1a}$, $R^{1b}$, $R^2$, $R^{3a}$ and $R^{3b}$ is independently H, halogen, unsubstituted or substituted $C_1$-$C_6$ alkyl, or $C_1$-$C_6$ haloalkyl.

Some embodiments of the present disclosure relate to an oligonucleotide or polynucleotide comprising a 3'-OH blocked labeled nucleotide described herein.

Some embodiments of the present disclosure relate to a method of preparing a growing polynucleotide complementary to a target single-stranded polynucleotide in a sequencing reaction, comprising incorporating a nucleotide molecule described herein into the growing complementary polynucleotide, wherein the incorporation of the nucleotide prevents the introduction of any subsequent nucleotide into the growing complementary polynucleotide. In some embodiments, the incorporation of the nucleotide is accomplished by a polymerase, a terminal deoxynucleotidyl transferase (TdT), or a reverse transcriptase. In one embodiment, the incorporation is accomplished by a polymerase (e.g., a DNA polymerase).

Some further embodiments of the present disclosure relate to a method for determining the sequence of a target single-stranded polynucleotide, comprising:

(a) incorporating a nucleotide described herein into a copy polynucleotide strand complementary to at least a portion of the target polynucleotide strand;

(b) detecting the identity of the nucleotide incorporated into the copy polynucleotide strand; and (c) chemically removing the label and the 3'-OH blocking group from the nucleotide incorporated into the copy polynucleotide strand.

In some embodiments, the detecting step comprises determining the identity of the nucleotide incorporated into the copy polynucleotide strand by taking one or more measurements of the fluorescent signal from the detectable label. In some embodiments, the sequencing method further comprises (d) using a post-cleavage washing solution to wash the chemically removed label and the 3'-OH blocking group away from the copy polynucleotide strand. In some embodiment, such washing step also removes the unincorporated nucleotides. In other embodiments, the method may comprise a separate washing step to wash the unincorporated nucleotides away from the copy polynucleotide strand before step (b). In some such embodiments, the 3'-OH blocking group and the detectable label of the incorporated nucleotide are removed prior to introducing the next complementary nucleotide. In some further embodiments, the 3'-OH blocking group and the detectable label are removed in a single step of chemical reaction. In some embodiments, the sequential incorporation described herein is performed at least 50 times, at least 100 times, at least 150 times, at least 200 times, or at least 250 times.

Some further embodiments of the present disclosure relate to kits comprising a plurality of nucleotide or nucleoside molecules described herein, and packaging materials therefor. The nucleotides, nucleosides, oligonucleotides, or kits that are set forth herein may be used to detect, measure, or identify a biological system (including, for example, processes or components thereof). Exemplary techniques that can employ the nucleotides, oligonucleotides, or kits include sequencing, expression analysis, hybridization analysis, genetic analysis, RNA analysis, cellular assay (e.g., cell binding or cell function analysis), or protein assay (e.g., protein binding assay or protein activity assay). The use may be on an automated instrument for carrying out a particular technique, such as an automated sequencing instrument. The sequencing instrument may contain two or more lasers operating at different wavelengths to distinguish between different detectable labels.

DETAILED DESCRIPTION

Figure 1:
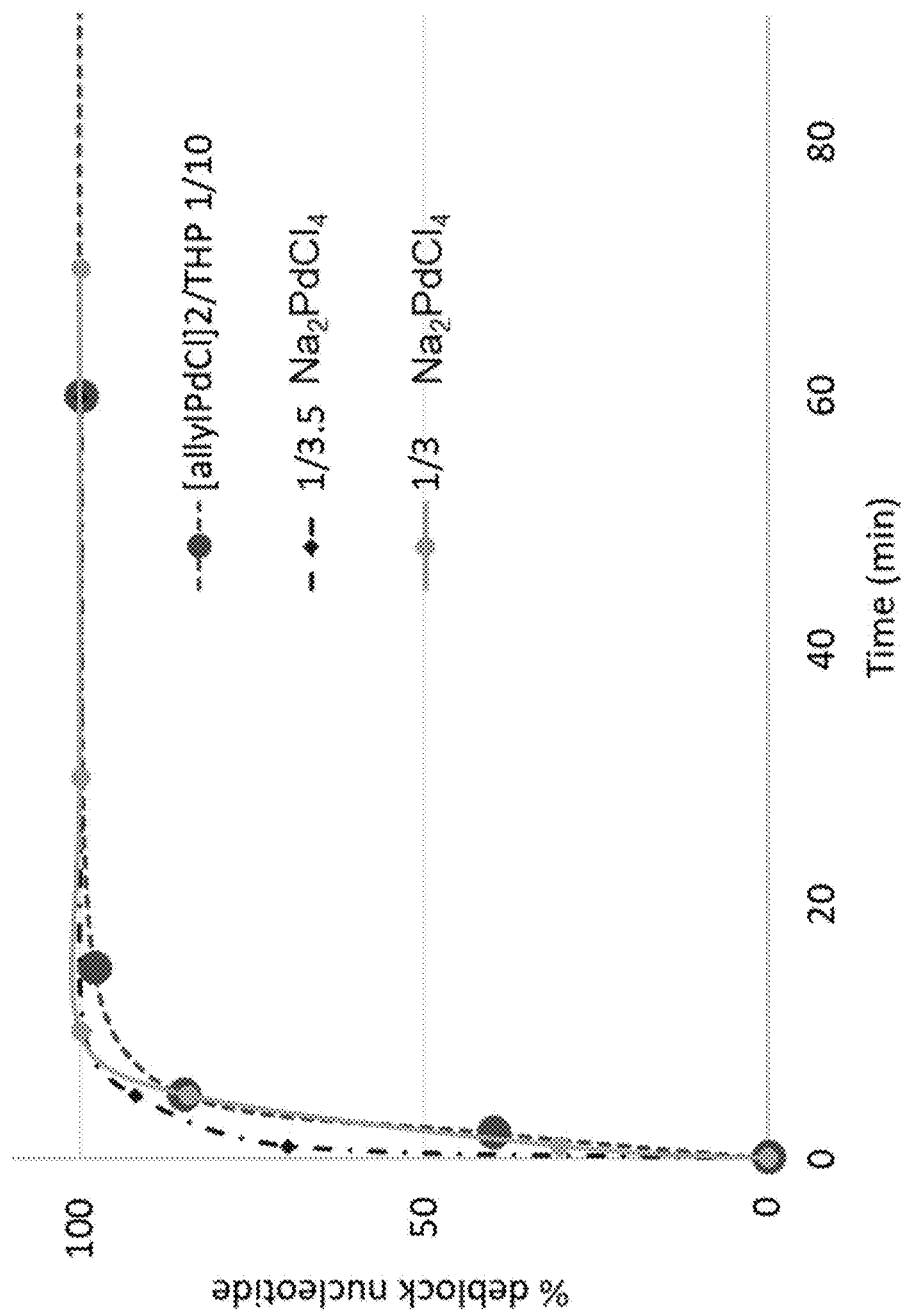
FIG. 1 is a line chart comparing the 3'-OH deblocking efficiency of [(allyl)PdCl]$_2$ with Na$_2$PdCl$_4$ when various ratio of tris(hydroxylpropyl)phosphine (THP) is used.

Embodiments of the present disclosure relate to nucleosides and nucleotides with 3' acetal blocking groups for sequencing applications, for example, sequencing-by-synthesis (SBS). In some embodiments, the nucleoside or nucleotide comprises a label covalently attached thereto through a cleavable linker comprising an acetal moiety that allows for cleavage of the 3' acetal blocking group and the label in a single step of reaction. The 3' acetal blocking groups offer improved stability during the synthesis of the fully functionalized nucleotides (ffNs) and also great stability in solution during formulation, storage and operation on the sequencing instruments. In addition, the 3' acetal blocking groups described herein may also achieve low prephasing, lower signal decay for improved data quality, which enables longer reads from the sequencing applications.

Definitions

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

Where a range of values is provided, it is understood that the upper and lower limit, and each intervening value between the upper and lower limit of the range is encompassed within the embodiments.

As used herein, common organic abbreviations are defined as follows:
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
ddNTP Dideoxynucleotide triphosphate
ffN Fully functionalized nucleotide
RT Room temperature
SBS Sequencing by Synthesis
SM Starting material As used herein, the term "array" refers to a population of different probe molecules that are attached to one or more substrates such that the different probe molecules can be differentiated from each other according to relative location. An array can include different probe molecules that are each located at a different addressable location on a substrate. Alternatively, or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, any "R" group(s) represent substituents that can be attached to the indicated atom. An R group may be substituted or unsubstituted. If two "R" groups are described as "together with the atoms to which they are attached" forming a ring or ring system, it means that the collective unit of the atoms, intervening bonds and the two R groups are the recited ring. For example, when the following substructure is present:

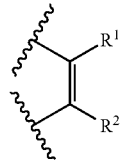

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

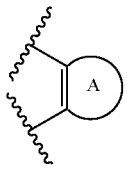

where A is an aryl ring or a carbocyclyl containing the depicted double bond.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "$C_a$ to $C_b$" in which "a" and "b" are integers refer to the number of carbon atoms in an alkyl, alkenyl or alkynyl group, or the number of ring atoms of a cycloalkyl or aryl group. That is, the alkyl, the alkenyl, the alkynyl, the ring of the cycloalkyl, and ring of the aryl can contain from "a" to "b", inclusive, carbon atoms. For example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, alkenyl, alkynyl, cycloalkyl, or aryl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_2$-$C_6$ alkenyl includes $C_2$, $C_3$, $C_4$, $C_5$ and $C_6$ alkenyl, $C_2$-$C_5$ alkenyl, $C_3$-$C_4$ alkenyl, etc.; and $C_2$-$C_6$ alkynyl includes $C_2$, $C_3$, $C_4$, $C_5$ and $C_6$ alkynyl, $C_2$-$C_5$ alkynyl, $C_3$-$C_4$ alkynyl, etc. $C_3$-$C_8$ cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_1$-$C_4$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_1$-$C_9$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. The alkenyl group may be designated as "$C_2$-$C_6$ alkenyl" or similar designations. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. The alkynyl group may be designated as "$C_2$-$C_6$ alkynyl" or similar designations. By way of example only, "$C_2$-$C_6$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 6 carbon atoms. The heteroalkyl group may be designated as "$C_1$-$C_6$ heteroalkyl" or similar designations. The heteroalkyl group may contain one or more heteroatoms. By way of example only, "$C_4$-$C_6$ heteroalkyl" indicates that there are four to six carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_6$-$C_{10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_1$-$C_6$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_1$-$C_6$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_3$-$C_6$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidinyl, pyrrolidonyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy)alkyl" refers to an alkoxy group connected via an —O-(alkylene) group, such as —O—($C_1$-$C_6$ alkoxy)$C_1$-$C_6$ alkyl, for example, —O—$(CH_2)_{1-3}$—$OCH_3$.

As used herein, "(heterocyclyl)alkyl" refer to a heterocyclic or a heterocyclyl group, as defined above, connected, as a substituent, via an alkylene group, as defined above. The alkylene and heterocyclyl groups of a (heterocyclyl)alkyl may be substituted or unsubstituted. Examples include but are not limited to (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

As used herein, "(cycloalkyl)alkyl" or "(carbocyclyl)alkyl" refers to a cycloalkyl or carbocyclyl group (as defined herein) connected, as a substituent, via an alkylene group. Examples include but are not limited to cyclopropylmethyl, cyclobutylmethyl, cyclopentylethyl, and cyclohexylpropyl.

An "O-carboxy" group refers to a "—OC(=O)R" group in which R is selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

A "C-carboxy" group refers to a "—C(=O)OR" group in which R is selected from the group consisting of hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein. A non-limiting example includes carboxyl (i.e., —C(=O)OH).

A "sulfonyl" group refers to an "—$SO_2$R" group in which R is selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

A "sulfino" group refers to a "—S(=O)OH" group.

A "S-sulfonamido" group refers to a "—$SO_2NR_AR_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

An "N-sulfonamido" group refers to a "—$N(R_A)SO_2R_B$" group in which $R_A$ and $R_b$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

A "C-amido" group refers to a "—C(=O)$NR_AR_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

An "N-amido" group refers to a "—$N(R_A)C(=O)R_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

An "amino" group refers to a "—$NR_AR_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein. A non-limiting example includes free amino (i.e., —$NH_2$).

An "aminoalkyl" group refers to an amino group connected via an alkylene group.

An "(alkoxy)alkyl" group refers to an alkoxy group connected via an alkylene group, such as a "($C_1$-$C_6$alkoxy)$C_1$-$C_6$ alkyl" and the like.

The term "hydroxy" as used herein refers to a —OH group.

The term "cyano" group as used herein refers to a "—CN" group.

The term "azido" as used herein refers to a —$N_3$ group.

The term "propargylamine" as used herein, refers to an amino group that is substituted with a propargyl group

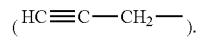

When propargylamine is used in the context as a bivalent moiety, it includes

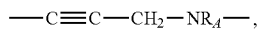

where $R_A$ is hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

The term "propargylamide" as used herein, refers to a C-amido or N-amido group that is substituted with a propargyl group

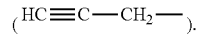

When propargylamide is used in the context as a bivalent moiety, it includes

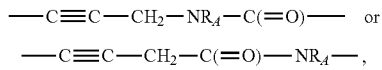

where $R_A$ is hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

The term "allylamine" as used herein, refers to an amino group that is substituted with an allyl group ($CH_2$=CH—$CH_2$—). When allylamine is used in the context as a bivalent moiety, it includes —CH=CH—$CH_2$—$NR_A$—, where $R_A$ is hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

The term "allylamide" as used herein, refers to a C-amido or N-amido group that is substituted with an allyl group ($CH_2$=CH—$CH_2$—). When allylamide is used in the context as a bivalent moiety, it includes —CH=CH—$CH_2$—$NR_A$—C(=O)— or —CH=CH—$CH_2$—C(=O)—$NR_A$—, where $R_A$ is hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

When a group is described as "optionally substituted" it may be either unsubstituted or substituted. Likewise, when a group is described as being "substituted", the substituent may be selected from one or more of the indicated substituents. As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), (aryl)$C_1$-$C_6$ alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), (5-10 membered heteroaryl)$C_1$-$C_6$ alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, —CN, hydroxy, $C_1$-$C_6$ alkoxy, ($C_1$-$C_6$ alkoxy)$C_1$-$C_6$ alkyl, —O($C_1$-$C_6$ alkoxy)$C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy, sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —$SO_3H$, sulfino, —$OSO_2C_{1-4}$alkyl, monophosphate, diphosphate, triphosphate, and oxo (=O). Wherever a group is described as "optionally substituted" that group can be substituted with the above substituents.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

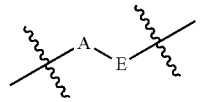

includes the substituent being oriented such that the A is attached at the leftmost attachment point of the molecule as well as the case in which A is attached at the rightmost attachment point of the molecule. In addition, if a group or substituent is depicted as

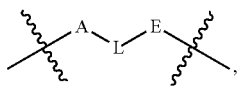

and L is defined an optionally present linker moiety; when L is not present (or absent), such group or substituent is equivalent to

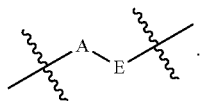

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, adenine, 7-deaza adenine, guanine, 7-deaza guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, when an oligonucleotide or polynucleotide is described as "comprising" or "labeled with" a nucleoside or nucleotide described herein, it means that the nucleoside or nucleotide described herein forms a covalent bond with the oligonucleotide or polynucleotide. Similarly, when a nucleoside or nucleotide is described as part of an oligonucleotide or polynucleotide, such as "incorporated into" an oligonucleotide or polynucleotide, it means that the nucleoside or nucleotide described herein forms a covalent bond with the oligonucleotide or polynucleotide. In some such embodiments, the covalent bond is formed between a 3' hydroxy group of the oligonucleotide or polynucleotide with the 5' phosphate group of a nucleotide described herein as a phosphodiester bond between the 3' carbon atom of the oligonucleotide or polynucleotide and the 5' carbon atom of the nucleotide.

As used herein, the term "cleavable linker" is not meant to imply that the whole linker is required to be removed. The cleavage site can be located at a position on the linker that ensures that part of the linker remains attached to the detectable label and/or nucleoside or nucleotide moiety after cleavage.

As used herein, "derivative" or "analog" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

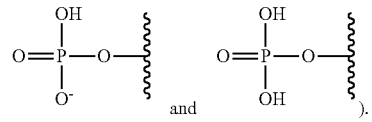

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Sometimes, "protecting group" and "blocking group" can be used interchangeably.

As used herein, the term "phasing" refers to a phenomenon in SBS that is caused by incomplete removal of the 3' terminators and fluorophores, and failure to complete the incorporation of a portion of DNA strands within clusters by polymerases at a given sequencing cycle. Pre-phasing is caused by the incorporation of nucleotides without effective 3' terminators, wherein the incorporation event goes 1 cycle ahead due to a termination failure. Phasing and pre-phasing cause the measured signal intensities for a specific cycle to consist of the signal from the current cycle as well as noise from the preceding and following cycles. As the number of cycles increases, the fraction of sequences per cluster affected by phasing and pre-phasing increases, hampering the identification of the correct base. Pre-phasing can be caused by the presence of a trace amount of unprotected or unblocked 3'-OH nucleotides during sequencing by synthesis (SBS). The unprotected 3'-OH nucleotides could be generated during the manufacturing processes or possibly during the storage and reagent handling processes. Accordingly, the discovery of nucleotide analogues which decrease the incidence of pre-phasing is surprising and provides a great advantage in SBS applications over existing nucleotide analogues. For example, the nucleotide analogues provided can result in faster SBS cycle time, lower phasing and pre-phasing values, and longer sequencing read lengths.

Nucleosides or Nucleotides with 3' Acetal Blocking Groups

Some embodiments of the present disclosure relate to a nucleotide or nucleoside molecule comprising a nucleobase attached to a detectable label via a cleavable linker and a ribose or deoxyribose moiety, wherein the cleavable linker comprises a moiety of the structure:

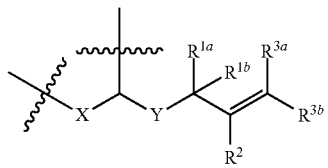

wherein each of X and Y is independently O or S; and each of $R^{1a}$, $R^{1b}$, $R^2$, $R^{3a}$ and $R^{3b}$ is independently H, halogen, unsubstituted or substituted $C_1$-$C_6$ alkyl, or $C_1$-$C_6$ haloalkyl. In some embodiment, the ribose or deoxyribose moiety comprises a 3'-OH protecting group described herein. In some embodiments, the cleavable linker may further comprise $L^1$ or $L^2$, or both, where $L^1$ and $L^2$ are described in details below.

In some embodiments, the nucleoside or nucleotide described herein comprises or has the structure of Formula (I):

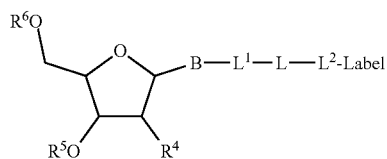

wherein B is the nucleobase;
$R^4$ is H or OH;
$R^5$ is H, a 3'-OH blocking group, or a phosphoramidite;
$R^6$ is H, monophosphate, diphosphate, triphosphate, thiophosphate, a phosphate ester analog, a reactive phosphorous containing group, or a hydroxy protecting group;
L is

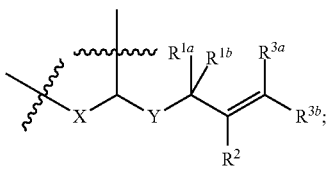

and
each of $L^1$ and $L^2$ is independently an optionally present linker moiety.

In some embodiments of the cleavable linker moiety described herein, each of X and Y is O. In some other embodiments, X is S and Y is O, or X is O and Y is S. In some embodiments, each of $R^{1a}$, $R^{1b}$, $R^2$, $R^{3a}$ and $R^{3b}$ is H. In other embodiments, at least one of $R^{1a}$, $R^{1b}$, $R^2$, $R^{3a}$ and $R^{3b}$ is halogen (e.g., fluoro, chloro) or unsubstituted $C_1$-$C_6$ alkyl (e.g., methyl, ethyl, isopropyl, isobutyl, or t-butyl). In some such instances, each of $R^{1a}$ and $R^{1b}$ is H and at least one of $R^2$, $R^{3a}$ and $R^{3b}$ is unsubstituted $C_1$-$C_6$ alkyl or halogen (for example, $R^2$ is unsubstituted $C_1$-$C_6$ alkyl and each of $R^{3a}$ and $R^{3b}$ is H; or $R^2$ is H and one or both of $R^{3a}$ and $R^{3b}$ is halogen or unsubstituted $C_1$-$C_6$ alkyl). In one embodiment, the cleavable linker or L comprises

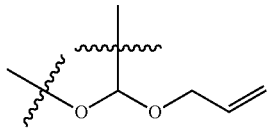 [SMILES: *OC(*)OCC=C]

("AOL" linker moiety).

In some embodiments of the nucleoside or nucleotide described herein, the nucleobase ("B" in Formula (I)) is purine (adenine or guanine), a deaza purine, or a pyrimidine (e.g., cytosine, thymine or uracil). In some further embodiments, the deaza purine is 7-deaza purine (e.g., 7-deaza adenine or 7-deaza guanine). Non-limiting examples of B comprises

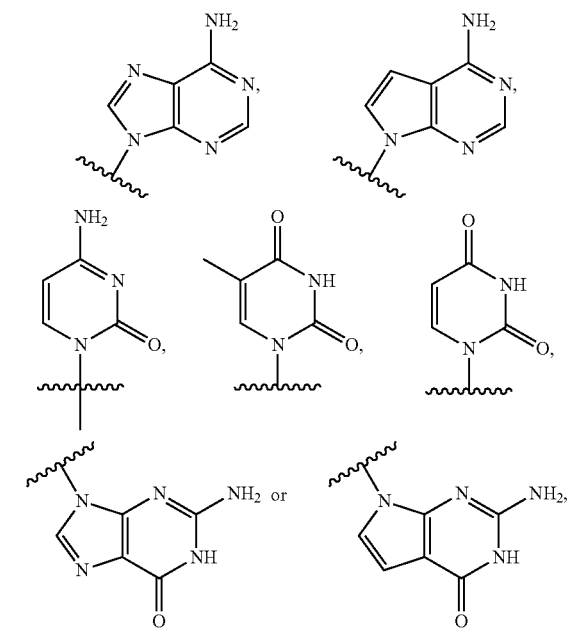

or optionally substituted derivatives and analogs thereof. In some further embodiments, the labeled nucleobase comprises the structure

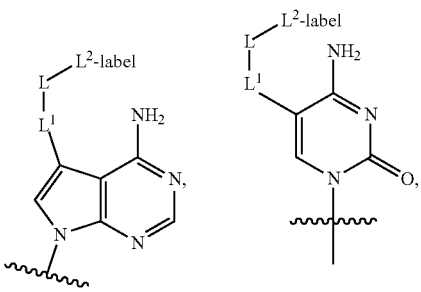

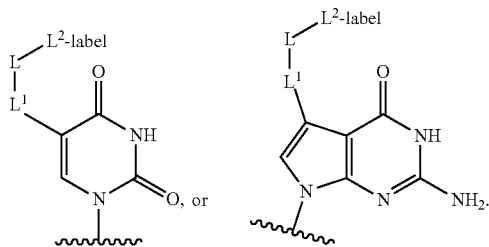

In some embodiments of the nucleoside or nucleotide described herein, the ribose or deoxyribose moiety comprises a 3'-OH blocking group (i.e., $R^5$ in Formula (I) is a 3'-OH blocking group). In some embodiments, the 3'-OH blocking group or $R^5$ is

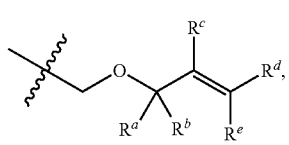

and wherein each of $R^a$, $R^b$, $R^c$, $R^d$ and $R^e$ is independently H, halogen, unsubstituted or substituted $C_1$-$C_6$ alkyl, or $C_1$-$C_6$ haloalkyl. In some further embodiments, each of $R^a$ and $R^b$ is H and at least one of $R^c$, $R^d$ and $R^e$ is independently halogen (e.g., fluoro, chloro) or unsubstituted $C_1$-$C_6$ alkyl (e.g., methyl, ethyl, isopropyl, isobutyl, or t-butyl). For example, $R^c$ is unsubstituted $C_1$-$C_6$ alkyl and each of $R^d$ and $R^e$ is H. In another example, $R^c$ is H and one or both of $R^d$ and $R^e$ is halogen or unsubstituted $C_1$-$C_6$ alkyl. Other non-limiting embodiments of $R^5$ include

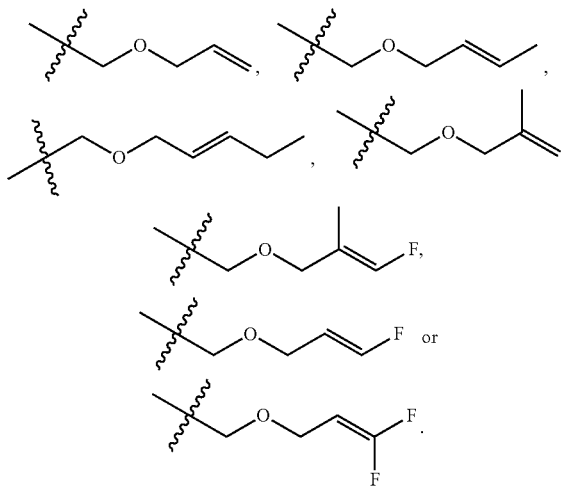

In one embodiment, $R^5$ is

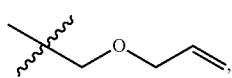

and together with the 3' oxygen it forms

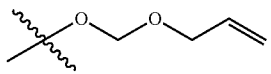 [SMILES: *OCOCC=C]

("AOM") group attached to the 3' carbon atom of the ribose or deoxyribose moiety. In other embodiments, the 3'-OH blocking group or $R^5$ may comprise an azido moiety (e.g., —$CH_2N_3$ or azidomethyl). Additional embodiments of the 3'-OH blocking groups are described in U.S. Patent Publication No. 2020/0216891 A1, which is incorporated by reference in its entirety and includes additional examples of 3' acetal blocking groups such as

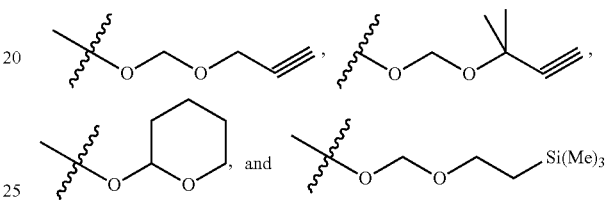

attached to the 3' carbon atom of the ribose or deoxyribose moiety.

In some other embodiments of the nucleoside or nucleotide described herein, $R^5$ in Formula (I) is a phosphoramidite. In such embodiments, $R^6$ is an acid-cleavable hydroxy protecting group which allows subsequent monomer coupling under automated synthesis conditions.

In some embodiments of the nucleoside or nucleotide described herein, $L^1$ is present and $L^1$ comprises a moiety selected from the group consisting of a propargylamine, a propargylamide, an allylamine, an allylamide, and optionally substituted variants thereof. In some further embodiments, $L^1$ comprises or is

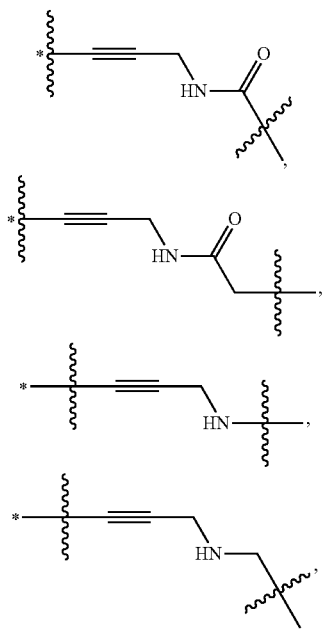

-continued

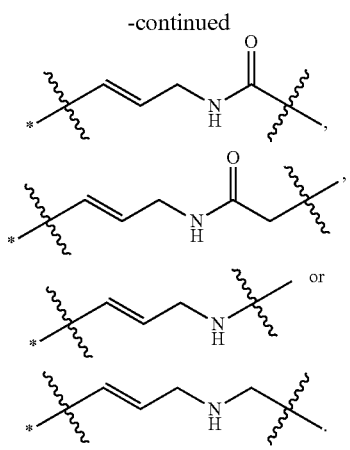

In some further embodiments, the asterisk * indicates the point of attachment of $L^1$ to the nucleobase (e.g., C5 position of a pyrimidine base or the C7 position of a 7-deaza purine base).

In some embodiments, the nucleotide described herein is a fully functionalized nucleotide (ffN) comprises a 3'-OH blocking group described herein and a dye compound covalently attached to the nucleobase through the cleavable linker described herein, where the cleavable linker comprises $L^1$ of the structure

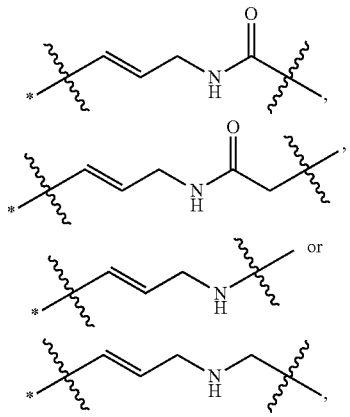

and * indicates the point of attachment of $L^1$ to the nucleobase (e.g., $C_5$ position of cytosine, thymine or uracil base, or the $C_7$ position of 7-deaza adenine or 7-deaza guanine). In some instances, ffNs with the allylamine or allylamide linker moiety described herein is also called ffN-DB or ffN-(DB), where "DB" refers to the double bond in the linker moiety. In some instances, sequencing runs with ffNs set (including ffA, ffT, ffC and ffG) where one or more ffNs is ffN-DB provide superior incorporation rate of the ffNs as compared to the ffNs set with propargylamine or propargylamide linker moiety (also known as ffN-PA or ffN-(PA)) described herein. For example, ffNs-DB set with allylamine or allylamide linker moiety and 3'-AOM blocking group described herein may confer at least 5%, 10%, 20%, 30%, 40%, 50%, 60%, 70%, 80%, 90%, 100%, 200%, 300%, 400%, or 500%, improvement on incorporation rate compared to the ffNs-PA set with 3'-O-azidomethyl blocking group at the same condition for the same period of time, thereby improve phasing values. In other embodiments, the incorporation rate/speed is measured by surface kinetics Vmax on the surface of a substrate (e.g., a flow cell or cBot system). For example, ffNs-DB set with 3'-AOM blocking group may confer at least 5%, 10%, 20%, 30%, 40%, 50%, 60%, 70%, 80%, 90%, 100%, 200%, 300%, 400%, or 500%, improvement on Vmax value ($ms^{-1}$) compared to the ffNs-PA set with 3'-O-azidomethyl blocking group at the same condition for the same period of time. In some embodiments, the incorporation rate/speed is measured at ambient temperature or a temperature below ambient temperature (such as 4-10° C.). In other embodiments, the incorporation rate/speed is measured at an elevated temperature, such as 40° C., 45° C., 50° C., 55° C., 60° C. or 65° C. In some such embodiments, the incorporation rate/speed is measured in solution in a basic pH environment, e.g., at pH 9.0, 9.2, 9.4, 9.6, 9.8 or 10.0. In some such embodiments, the incorporation rate/speed is measured with the presence of an enzyme, such as a polymerase (e.g., a DNA polymerase), a terminal deoxynucleotidyl transferase, or a reverse transcriptase. In some embodiments, the ffN-DB is ffT-DB, ffC-DB or ffA-DB. In one embodiment, the ffNs-DB set with improved phasing value described herein comprises ffT-DB, ffC, ffA and ffG. In another embodiment, the ffNs-DB set with improved phasing value described herein comprises ffT-DB, ffC-DB, ffA and ffG. In yet another embodiment, the ffNs-DB set with improved phasing value described herein comprises ffT-DB, ffC-DB, ffA-DB and ffG.

In some further embodiments, when the nucleobase of the nucleotide described herein is thymine or optionally substituted derivatives and analogs thereof (i.e., the nucleotide is T), $L^1$ comprises an allylamine moiety or an allylamide moiety, or optionally substituted variants thereof. In particular examples, $L^1$ comprises or is

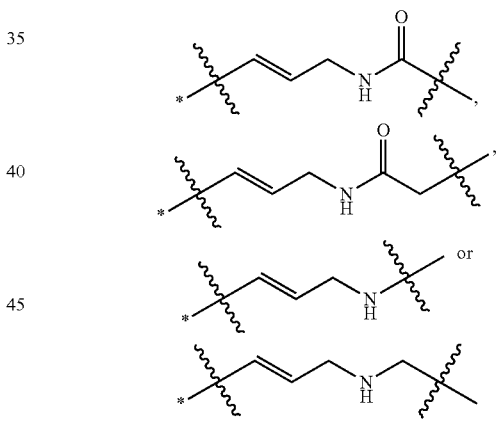

and * indicates the point of attachment of $L^1$ to the C5 position of the thymine base. In some embodiments, the T nucleotide described herein is a fully functionalized T nucleotide (ffT) labeled with a dye molecule through the cleavable linker comprising

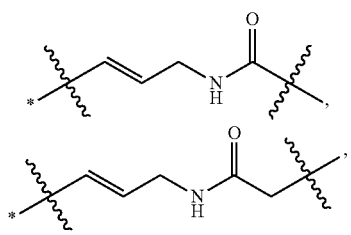

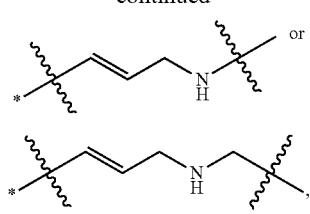

directly attached to the C5 position of the thymine base (i.e., ffT-DB). In some instances, when ffT-DB is used in sequencing applications in the presence of a palladium catalyst, it may substantially improve sequencing metrics such as phasing, pre-phasing and error rate. For example, when ffT-DB with 3'-AOM blocking group described herein is used, it may confer at least 50%, 100%, 200%, 300%, 400%, 500%, 600%, 700%, 800%, 900%, 1000%, 1500%, 2000%, 2500%, or 3000% improvement on one or more sequencing metrics described herein compared to when a standard ffT-PA with 3'-O-azidomethyl blocking group is used.

Some further embodiments of the nucleoside or nucleotide described herein include those with Formula (Ia), (Ia'), (Ib), (Ic), (Ic') or (Id):

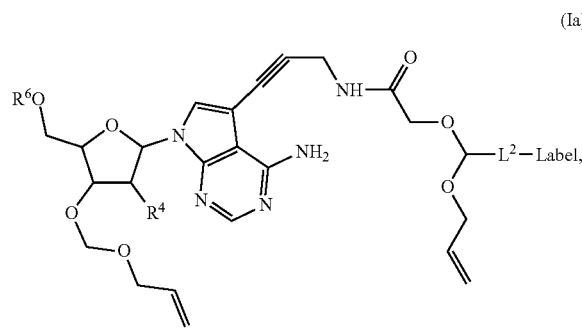

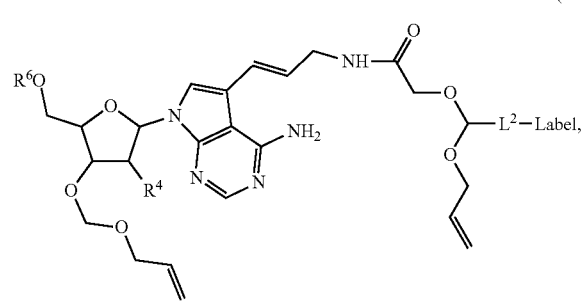

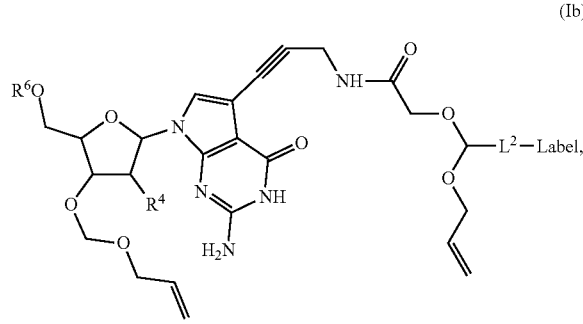

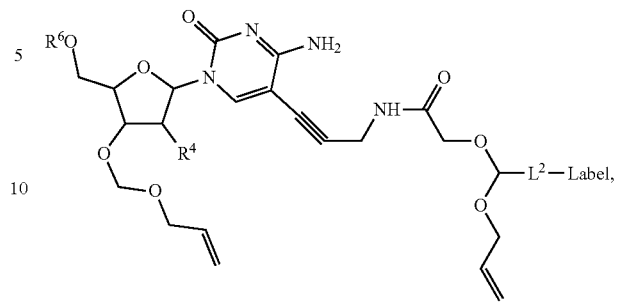

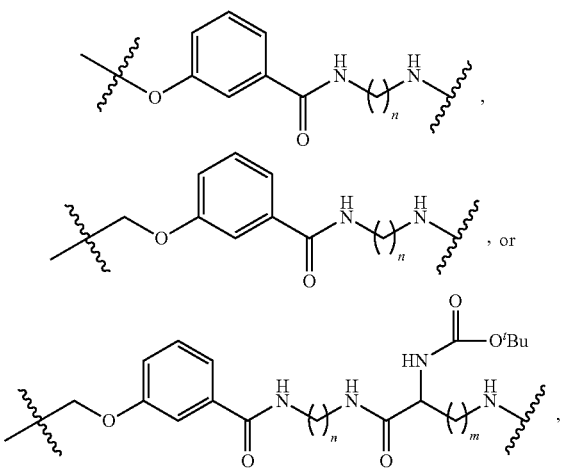

In some further embodiments of the nucleoside or nucleotide described herein, $L^2$ is present and $L^2$ comprises wherein each of n and m is independently an integer of 1, 2, 3, 4, 5, 6, 7, 8, 9 or 10 and the phenyl moiety is optionally substituted. In some such embodiments, n is 5 and the phenyl moiety of $L^2$ is unsubstituted. In some further embodiments, m is 4.

In any embodiments of the nucleoside or nucleotide described herein, the cleavable linker or $L^1/L^2$ may further comprise a disulfide moiety or azido moiety (such as

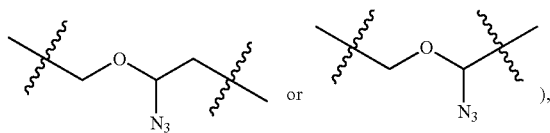 [SMILES: *COC(C*)N=[N+]=[N-] ; *COC(*)N=[N+]=[N-]]

or a combination thereof. Additional non-limiting examples of a linker moiety may be incorporated into $L^1$ or $L^2$ include:

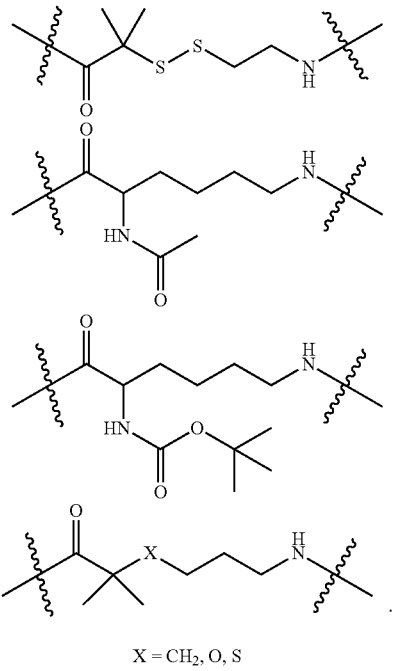

X = CH$_2$, O, S

Additional linker moieties are disclosed in WO 2004/018493 and U.S. Publication No. 2016/0040225, which are herein incorporated by references.

In any embodiments of nucleoside or nucleotide described herein, the nucleoside or nucleotide comprises a 2' deoxyribose moiety (i.e., $R^4$ is Formula (I) and (Ia)-(Id)) is H). In some further aspect, the 2' deoxyribose contains one, two or three phosphate groups at the 5' position of the sugar ring. In some further aspect, the nucleotides described herein are nucleotide triphosphate (i.e., $R^6$ in Formula (I) and (Ia)-(Id)) forms triphosphate).

In any embodiments of the nucleoside or nucleotide described herein, the detectable label may comprise a fluorescent dye.

Additional embodiments of the present disclosure relate to an oligonucleotide or a polynucleotide comprising a nucleoside or nucleotide described herein. For example, an oligonucleotide or polynucleotide incorporating a nucleotide of Formula (Ia') comprises the following structure:

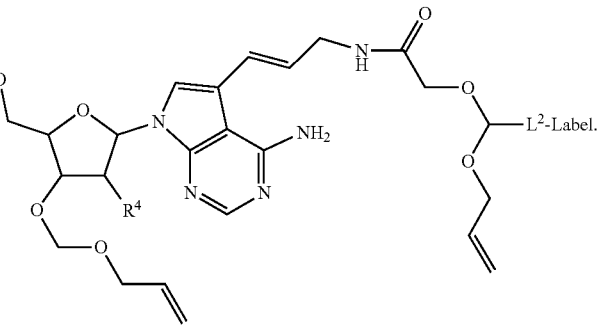

In some such embodiments, the oligonucleotide or polynucleotide is hybridized to a template or target polynucleotide. In some such embodiments, the template polynucleotide is immobilized on a solid support.

Additional embodiments of the present disclosure relate to a solid support comprises an array of a plurality of immobilized template or target polynucleotides and at least a portion of such immobilized template or target polynucleotides is hybridized to an oligonucleotide or a polynucleotide comprising a nucleoside or nucleotide described herein.

In any embodiments of the nucleotides or nucleosides described herein, the 3'-OH blocking group and the cleavable linker (and the attached label) may be removable under the same or substantially same chemical reaction conditions, for example, the 3'-OH blocking group and the detectable label may be removed in a single chemical reaction. In other embodiments, the 3'-OH blocking group and the detectable labeled are removed in two separate steps.

In some embodiments, the 3' blocked nucleotides or nucleosides described herein provide superior stability in solution or lyophilized form during storage, or reagent handling during sequencing applications, compared to the same nucleotides or nucleosides protected with a standard 3'-OH blocking group disclosed in the prior art, for example, the 3'-O-azidomethyl protecting group. For example, the acetal blocking groups disclosed herein may confer at least 5%, 10%, 20%, 30%, 40%, 50%, 60%, 70%, 80%, 90%, 100%, 200%, 300%, 400%, 500%, 600%, 700%, 800%, 900%, 1000%, 1500%, 2000%, 2500%, or 3000% improved stability compare to an azidomethyl protected 3'-OH at the same condition for the same period of time, thereby reducing the pre-phasing values and resulting in longer sequencing read lengths. In some embodiments, the stability is measured at ambient temperature or a temperature below ambient temperature (such as 4-10° C.). In other embodiments, the stability is measured at an elevated temperature, such as 40° C., 45° C., 50° C., 55° C., 60° C. or 65° C. In some such embodiments, the stability is measured in solution in a basic pH environment, e.g., at pH 9.0, 9.2, 9.4, 9.6, 9.8. or 10.0. In some such embodiments, the stability is measured with or without the presence of an enzyme, such as a polymerase (e.g., a DNA polymerase), a terminal deoxynucleotidyl transferase, or a reverse transcriptase.

In some embodiments, the 3' blocked nucleotides or nucleosides described herein provide superior deblocking rate in solution during the chemical cleavage step of the sequencing applications, compared to the same nucleotides or nucleosides protected with a standard 3'-OH blocking group disclosed in the prior art, for example, the 3'-O-azidomethyl protecting group. For example, the acetal blocking groups disclosed herein may confer at least 5%, 10%, 20%, 30%, 40%, 50%, 60%, 70%, 80%, 90%, 100%, 150%, 200%, 300%, 400%, 500%, 600%, 700%, 800%, 900%, 1000%, 1500%, or 2000% improved deblocking rate compare to an azidomethyl protected 3'-OH using the standard deblocking reagent (such as tris(hydroxypropyl)phosphine), thereby reducing the overall time for a sequencing cycle. In some embodiments, the deblocking rate is measured at ambient temperature or a temperature below ambient temperature (such as 4-10° C.). In other embodiments, the deblocking rate is measured at an elevated temperature, such as 40° C., 45° C., 50° C., 55° C., 60° C. or 65° C. In some such embodiments, the deblocking rate is measured in solution in a basic pH environment, e.g., at pH 9.0, 9.2, 9.4, 9.6, 9.8. or 10.0. In some such embodiments, the molar ratio of the deblocking reagent to substrate (i.e., 3' blocked nucleoside or nucleotide) is about 10:1, about 5:1, about 2:1 or about 1:1.

In some embodiments, a palladium deblocking reagent (e.g., Pd(0) is used to remove the 3' acetal blocking groups (e.g., AOM blocking group). Pd may forms a chelation complex with the two oxygen atoms of the AOM group, as well as the double bond of the allyl group, allowing the deblocking reagent in direct vicinity of the functionality to be removed and may result in accelerated deblocking rate. For example, after Pd cleavage of the linker and the 3' blocking group of an incorporated nucleotide described herein having Formula (Ia), (Ia'), (Ib), (Ic), (Ic') or (Id), the remaining linker construct on the copy polynucleotide may comprise the following structure:

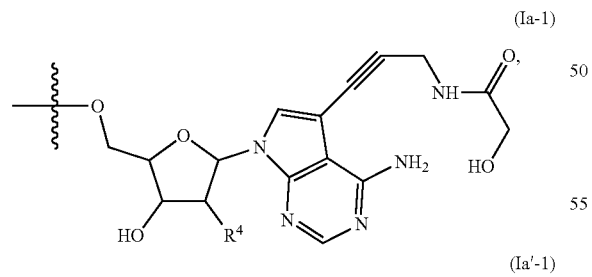
(Ia-1)

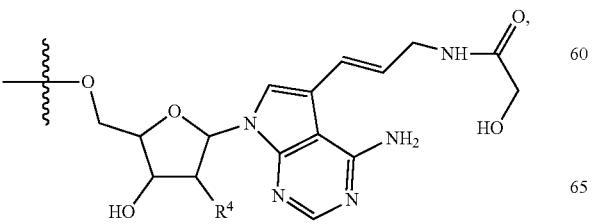
(Ia'-1)

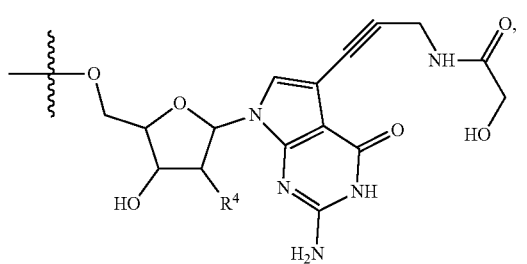
(Ib-1)

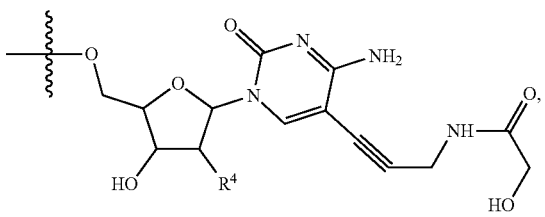
(Ic-1)

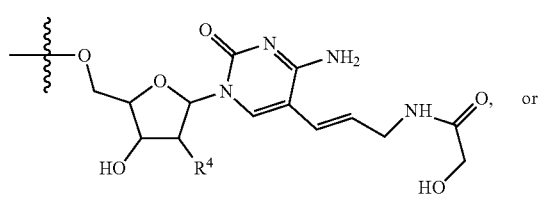
(Ic'-1)

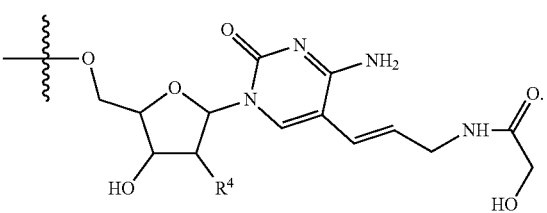
(Id-1)

The squiggle line refers to the attachment of the oxygen to the remaining phosphodiester linkage of the copy polynucleotide strand. For example,

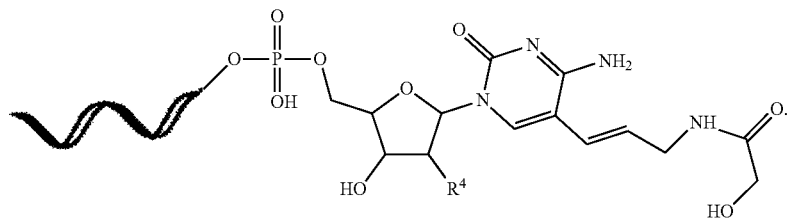

The allyl amido or propargyl amido moiety may further be cleaved by the Pd catalyst. In addition, the remaining linker construct that is attached to the detectable label has the structure:

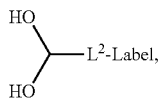

for example,

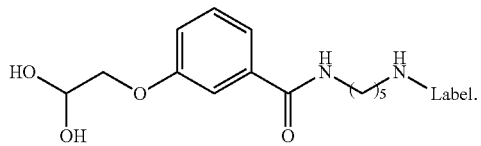

Cleavage Condition of the Cleavable Linker

The cleavable linker described herein may be removed or cleaved under various chemical conditions. Non-limiting cleaving condition includes a palladium catalyst, such as a Pd(II) complex (e.g., Pd(OAc)$_2$, allylPd(II) chloride dimer [(Allyl)PdCl]$_2$ or Na$_2$PdCl$_4$) in the presence of a water soluble phosphine ligand, for example tris(hydroxylpropyl) phosphine (THP or THPP) or tris(hydroxymethyl)phosphine (THMP). In some embodiments, the 3' acetal blocking group may be cleaved under the same or substantially the same cleavage condition as that for the cleavable linker.

Palladium Catalysts

In some embodiments, the 3' acetal blocking group and the cleavable linker described herein may be cleaved by a palladium catalyst. In some such embodiments, the Pd catalyst is water soluble. In some such embodiments, the Pd catalyst is a Pd(0) complex (e.g., Tris(3,3',3''-phosphinidynetris(benzenesulfonato)palladium(0) nonasodium salt nonahydrate). In some instances, the Pd(0) complex may be generated in situ from reduction of a Pd(II) complex by reagents such as alkenes, alcohols, amines, phosphines, or metal hydrides. Suitable palladium sources include Pd(CH$_3$CN)$_2$Cl$_2$, [PdCl(Allyl)]$_2$, [Pd(Allyl)(THP)]Cl, [Pd(Allyl)(THP)$_2$]Cl, Pd(OAc)$_2$, Pd(PPh$_3$)$_4$, Pd(dba)$_2$, Pd(Acac)$_2$, PdCl$_2$(COD), and Pd(TFA)$_2$. In one such embodiment, the Pd(0) complex is generated in situ from Na$_2$PdCl$_4$. In another embodiment, the palladium source is allyl palladium(II) chloride dimer [(Allyl)PdCl]$_2$ or [PdCl (C$_3$H$_5$)]$_2$. In some embodiments, the Pd(0) catalyst is generated in an aqueous solution by mixing a Pd(II) complex with a phosphine. Suitable phosphines include water soluble phosphines, such as tris(hydroxypropyl)phosphine (THP), tris(hydroxymethyl)phosphine (THMP), 1,3,5-triaza-7-phosphaadamantane (PTA), bis(p-sulfonatophenyl)phenylphosphine dihydrate potassium salt, tris(carboxyethyl) phosphine (TCEP), and triphenylphosphine-3,3',3''-trisulfonic acid trisodium salt.

In some embodiments, the palladium catalyst is prepared by mixing [(Allyl)PdCl]$_2$ with THP in situ. The molar ratio of [(Allyl)PdCl]$_2$ and the THP may be about 1:2, 1:3, 1:4, 1:5, 1:6, 1:7, 1:8, 1:9, or 1:10. In one embodiment, the molar ratio of [(Allyl)PdCl]$_2$ to THP is 1:10. In some other embodiment, the palladium catalyst is prepared by mixing a water soluble Pd reagent Na$_2$PdCl$_4$ with THP in situ. The molar ratio of Na$_2$PdCl$_4$ and THP may be about 1:2, 1:3, 1:4, 1:5, 1:6, 1:7, 1:8, 1:9, or 1:10. In one embodiment, the molar ratio of Na$_2$PdCl$_4$ to THP is about 1:3. In another embodiment, the molar ratio of Na$_2$PdCl$_4$ to THP is about 1:3.5. In some further embodiments, one or more reducing agents may be added, such as ascorbic acid or a salt thereof (e.g., sodium ascorbate). In some embodiments, the cleavage mixture may contain additional buffer reagents, such as a primary amine, a secondary amine, a tertiary amine, a natural amino acid, a non-natural amino acid, a carbonate salt, a phosphate salt, or a borate salt, or combinations thereof. In some further embodiments, the buffer reagent comprises ethanolamine (EA), tris(hydroxymethyl)aminomethane (Tris), glycine, sodium carbonate, sodium phosphate, sodium borate, dimethylethanolamine (DMEA), diethylethanolamine (DEEA), N,N,N',N'-tetramethylethylenediamine(TMEDA), N,N,N',N'-tetraethylethylenediamine (TEEDA), or 2-piperidine ethanol, or combinations thereof. In one embodiment, the one or more buffer reagents comprise DEEA. In another embodiment, the one or more buffer reagents contains one or more inorganic salts such as a carbonate salt, a phosphate salt, or a borate salt, or combinations thereof. In one embodiment, the inorganic salt is a sodium salt.

In other embodiments, the cleavage condition for the cleavable linker is different from that of the 3'-OH blocking group. For example, when the In addition, when the 3' blocking group is 3'-O-azidomethyl, the —CH$_2$N$_3$ moiety can be converted to an amino group by phosphine. Alternatively, the azido group in —CH$_2$N$_3$ may be converted to an amino group by contacting such molecules with the thiols, in particular water-soluble thiols such as dithiothreitol (DTT). In one embodiment, the phosphine is THP.

Compatibility with Linearization

In order to maximize the throughput of nucleic acid sequencing reactions it is advantageous to be able to sequence multiple template molecules in parallel. Parallel processing of multiple templates can be achieved with the use of nucleic acid array technology. These arrays typically consist of a high-density matrix of polynucleotides immobilized onto a solid support material.

WO 98/44151 and WO 00/18957 both describe methods of nucleic acid amplification which allow amplification products to be immobilized on a solid support in order to form arrays comprised of clusters or "colonies" formed from a plurality of identical immobilized polynucleotide strands and a plurality of identical immobilized complementary strands. Arrays of this type are referred to herein as "clustered arrays." The nucleic acid molecules present in DNA colonies on the clustered arrays prepared according to these methods can provide templates for sequencing reactions, for example as described in WO 98/44152. The products of solid-phase amplification reactions such as those described in WO 98/44151 and WO 00/18957 are so-called "bridged" structures formed by annealing of pairs of immobilized polynucleotide strands and immobilized complementary strands, both strands being attached to the solid support at the 5' end. In order to provide more suitable templates for nucleic acid sequencing, it is preferred to remove substantially all or at least a portion of one of the immobilized strands in the "bridged" structure in order to generate a template which is at least partially single-stranded. The portion of the template which is single-stranded will thus be available for hybridization to a sequencing primer. The process of removing all or a portion of one immobilized strand in a "bridged" double-stranded nucleic acid structure is referred to as "linearization." There are various ways for linearization, including but not limited to enzymatic cleavage, photo-chemical cleavage, or chemical cleavage. Non-limiting examples of linearization methods are disclosed in PCT Publication No. WO 2007/010251, U.S. Patent Publication No. 2009/0088327, U.S. Patent Publication No. 2009/0118128, and U.S. Publication No. 2019/0352327, which are incorporated by reference in their entireties.

In particular, amplification (e.g., bridge amplification or exclusion amplification) form arrays comprised of clusters or "colonies" formed from a plurality of identical immobilized target polynucleotide strands and a plurality of identical immobilized complementary strands. The target strand and the complementary stand form at least partially double-stranded polynucleotide complex, both strands are immobilized to the solid support at their 5' ends. The double stranded polynucleotides is contacted with an aqueous solution of a palladium catalyst, which cleave one strand at a cleavage site comprising an allyl modified nucleoside (e.g., allyl modified T nucleoside) to remove at least a portion of one of the immobilized strand in order to generate a template which is at least partially single-stranded. The portion of the template which is single-stranded will thus be available for hybridization to a sequencing primer to initiate first round of SBS (Read 1). In some embodiment, the allyl modified nucleoside is in the P5 primer sequence. This method is referred to as first chemical linearization, as compared to a standard enzymatic linearization where such removal or cleavage is facilitated by an enzymatic cleavage reaction using an enzyme USER to cleave the U position on the P5 primer.

In some embodiments, the condition for cleaving the cleavable linker and/or deprotecting or removal of the 3'-OH blocking groups is also compatible with the linearization processes. In some further embodiments, such cleavage condition is compatible with a chemical linearization process which comprises the use of a Pd complex and a phosphine. In some embodiments, the Pd complex is a Pd(II) complex (e.g., $Pd(OAc)_2$, $[(Allyl)PdCl]_2$ or $Na_2PdCl_4$), which generates Pd(0) in situ in the presence of the phosphine (e.g., THP). The chemical linearization process using a Pd catalyst to cleave an allyl modified T nucleoside in the P5 primer sequence is described in detail in U.S. Publication No. 2019/0352327, which is incorporated by reference in its entirety. In further embodiments, the Pd cleavage mix disclosed herein (e.g., [Pd(Allyl)Cl]$_2$) and THP in a buffer solution containing DEEA) may be directly used in the first chemical linearization step. The reagent number reduction allows for further instrument (fluidics and cartridges) simplification.

Unless indicated otherwise, the reference to nucleotides is also intended to be applicable to nucleosides.

Labeled Nucleotides

According to an aspect of the disclosure, the described 3'-OH blocked nucleotide also comprises a detectable label and such nucleotide is called a labeled nucleotide or a fully functionalized nucleotide (ffN). The label (e.g., a fluorescent dye) is conjugated via a cleavable linker by a variety of means including hydrophobic attraction, ionic attraction, and covalent attachment. In some aspect, the dyes are conjugated to the nucleotide by covalent attachment via the cleavable linker. In some instances, such labeled nucleotides are also referred to as "modified nucleotides." One of ordinary skill in the art understands that label may be covalently bounded to the linker by reacting a functional group of the label (e.g., carboxyl) with a functional group of the linker (e.g., amino).

Labeled nucleosides and nucleotides are useful for labeling polynucleotides formed by enzymatic synthesis, such as, by way of non-limiting example, in PCR amplification, isothermal amplification, solid phase amplification, polynucleotide sequencing (e.g., solid phase sequencing), nick translation reactions and the like.

In some embodiments, the dye may be covalently attached to oligonucleotides or nucleotides via the nucleotide base. For example, the labeled nucleotide or oligonucleotide may have the label attached to the C5 position of a pyrimidine base or the C7 position of a 7-deaza purine base through a cleavable linker moiety.

Unless indicated otherwise, the reference to nucleotides is also intended to be applicable to nucleosides. The present application will also be further described with reference to DNA, although the description will also be applicable to RNA, PNA, and other nucleic acids, unless otherwise indicated.

Nucleosides and nucleotides may be labeled at sites on the sugar or nucleobase. As known in the art, a "nucleotide" consists of a nitrogenous base, a sugar, and one or more phosphate groups. In RNA, the sugar is ribose and in DNA is a deoxyribose, i.e., a sugar lacking a hydroxy group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxy group attached to the C-3 or C-5 of the sugar. Nucleotides are usually mono-, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. In particular embodiments, the derivatives should be capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidite linkages and the like.

In particular embodiments the labeled nucleoside or nucleotide may be enzymatically incorporable and enzymatically extendable. Accordingly, a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

The disclosure also encompasses polynucleotides incorporating dye compounds. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, in combination with at least one modified nucleotide (e.g., labeled with a dye compound) as set forth herein. Polynucleotides according to the disclosure may also include non-natural backbone linkages and/or non-nucleotide chemical modifications. Chimeric structures comprised of mixtures of ribonucleotides and deoxyribonucleotides comprising at least one labeled nucleotide are also contemplated.

Non-limiting exemplary labeled nucleotides as described herein include:

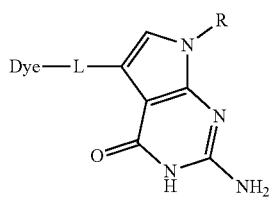

A

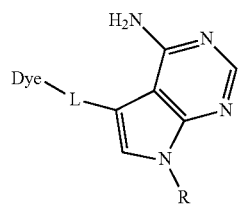

C

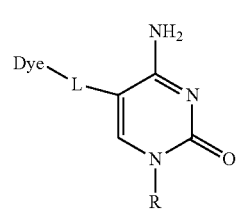

T

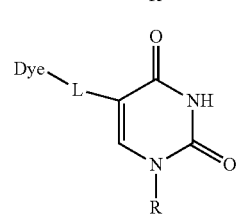

-continued

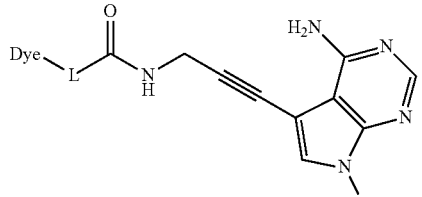

G

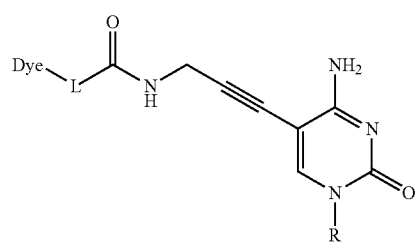

A

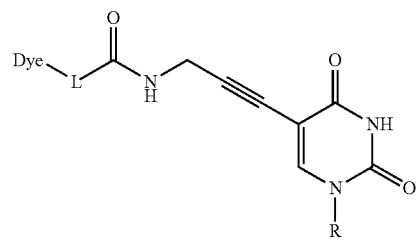

C

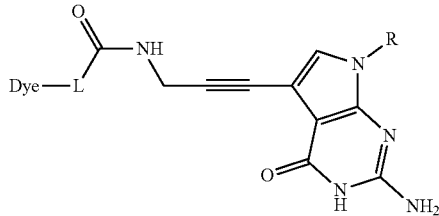

T

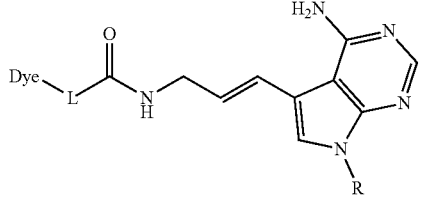

G

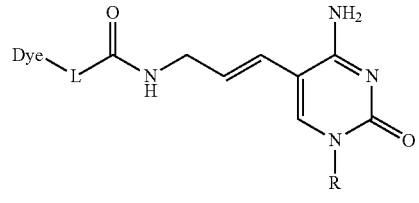

A

C

33
-continued

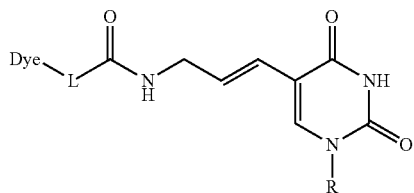

T

34
-continued

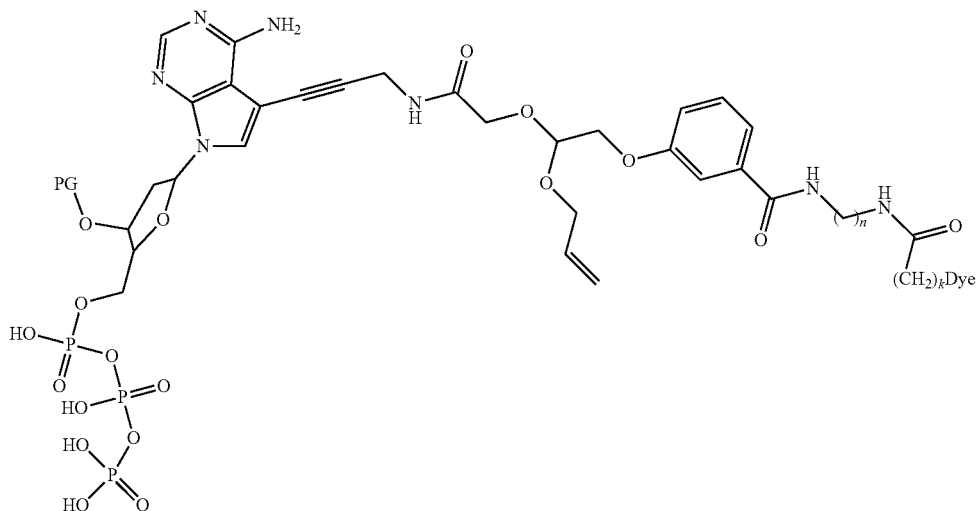

G wherein L represents a cleavable linker (optionally include L² described herein) and R represents a ribose or deoxyribose moiety as described above, or a ribose or deoxyribose moiety with the 5' position substituted with one, two or three phosphates.

In some embodiments, non-limiting exemplary fluorescent dye conjugates are shown below:

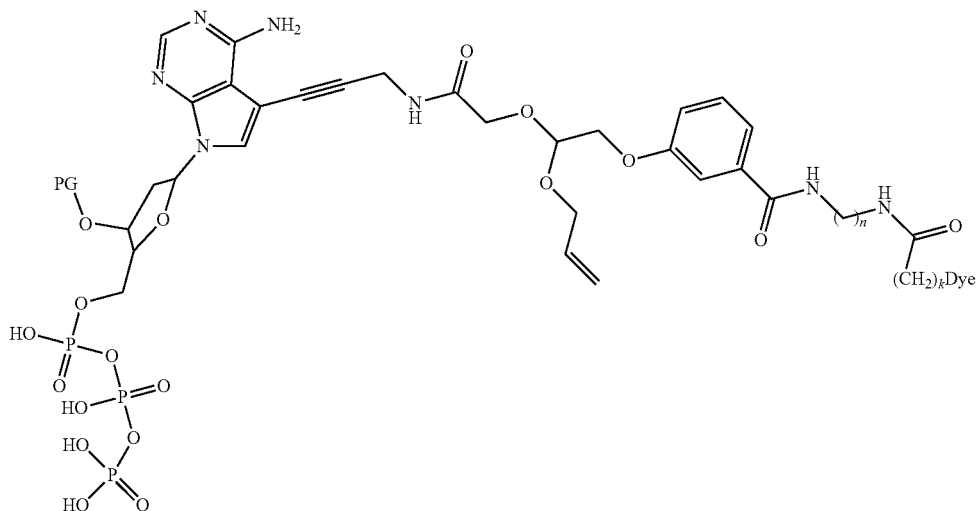

ffA-AOL-Dye

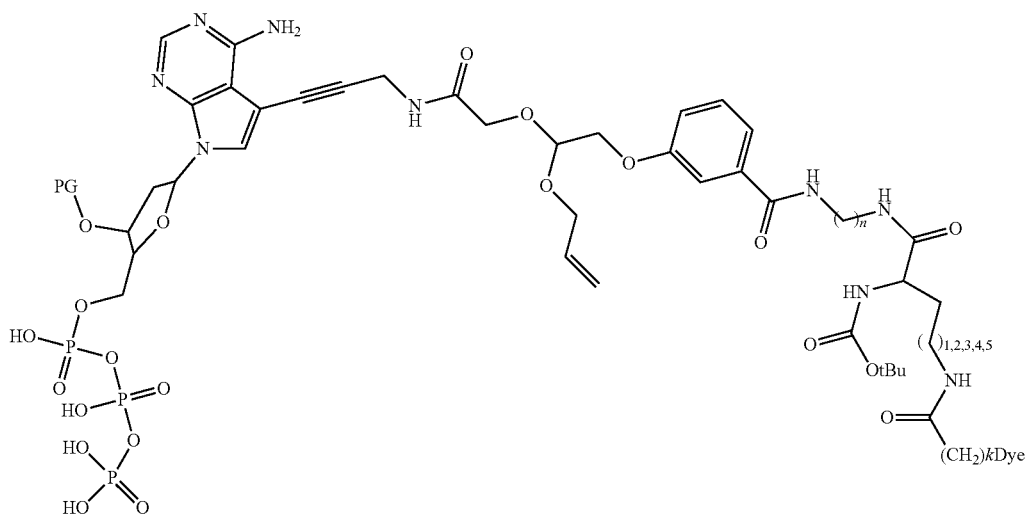

ffA-AOL-BL-Dye

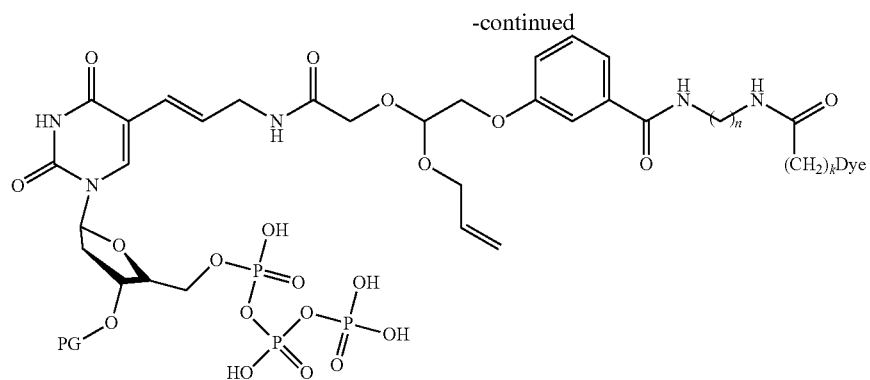

ffT-DB-AOL-Dye

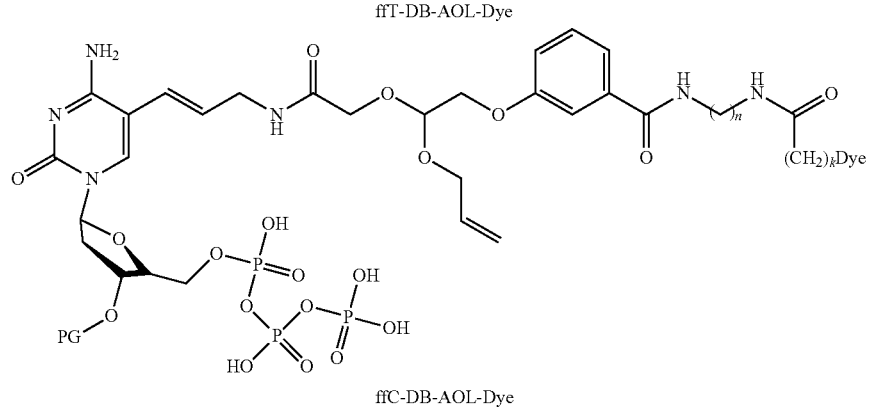

ffC-DB-AOL-Dye

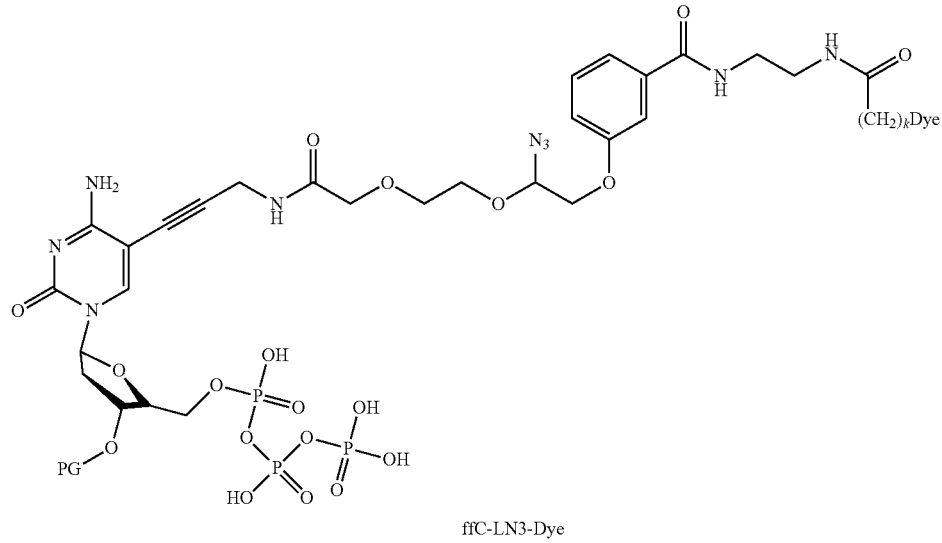

ffC-LN3-Dye wherein PG stands for the 3'-OH blocking groups described herein; n is an integer of 1, 2, 3, 4, 5, 6, 7, 8, 9, or 10; and k is 0, 1, 2, 3, 4, or 5. In one embodiment, —O-PG is AOM. In another embodiment, —O-PG is —O-azidomethyl. In one embodiment, n is 5.

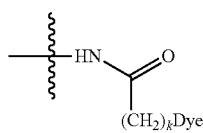

refers to the connection point of the Dye with the cleavable linker as a result of a reaction between an amino group of the linker moiety and the carboxyl group of the Dye.

Methods of Sequencing

Labeled nucleotides or nucleosides according to the present disclosure may be used in any method of analysis such as method that include detection of a fluorescent label attached to a nucleotide or nucleoside, whether on its own or incorporated into or associated with a larger molecular structure or conjugate. In this context the term "incorporated into a polynucleotide" can mean that the 5' phosphate is joined in phosphodiester linkage to the 3'-OH group of a second (modified or unmodified) nucleotide, which may itself form part of a longer polynucleotide chain. The 3' end of a nucleotide set forth herein may or may not be joined in phosphodiester linkage to the 5' phosphate of a further (modified or unmodified) nucleotide. Thus, in one non-limiting embodiment, the disclosure provides a method of detecting a nucleotide incorporated into a polynucleotide which comprises: (a) incorporating at least one nucleotide of the disclosure into a polynucleotide and (b) detecting the nucleotide(s) incorporated into the polynucleotide by detecting the fluorescent signal from the detectable label (e.g., a fluorescent compound) attached to said nucleotide(s). This method can include: a synthetic step (a) in which one or more nucleotides according to the disclosure are incorporated into a polynucleotide and a detection step (b) in which one or more nucleotide(s) incorporated into the polynucleotide are detected by detecting or quantitatively measuring their fluorescence.

Additional aspect of the present disclosure includes a method of preparing a growing polynucleotide complementary to a target single-stranded polynucleotide in a sequencing reaction, comprising incorporating a nucleotide described herein into a growing complementary polynucleotide, wherein the incorporation of the nucleotide prevents the introduction of any subsequent nucleotide into the growing complementary polynucleotide.

Some embodiments of the present disclosure relate to a method for determining the sequence of a target single-stranded polynucleotide, comprising:

(a) incorporating a nucleotide (e.g., dATP, dCTP, dGTP, dTTP or dUTP) comprising a 3'-OH blocking group

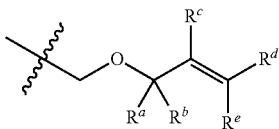

described herein (attached to the 3' oxygen) and a detectable label as described herein into a copy polynucleotide strand complementary to at least a portion of the target polynucleotide strand;

(b) detecting the identity of the nucleotide incorporated into the copy polynucleotide strand; and (c) chemically removing the label and the 3'-OH blocking group from the nucleotide incorporated into the copy polynucleotide strand.

In some embodiments, the sequencing method further comprises (d) washing the chemically removed label and the 3'-OH blocking group away from the copy polynucleotide strand by using a post-cleavable washing solution. In some such embodiments, the 3'-OH blocking group and the detectable label are removed prior to introducing the next complementary nucleotide. In some embodiment, the washing step (d) also remove unincorporated nucleotides. In other embodiments, the method may comprise a separate washing step to wash the unincorporated nucleotides away from the copy polynucleotide strand before step (b).

In some embodiments, steps (a) to (d) is repeated until a sequence of the portion of the target polynucleotide strand is determined. In some such embodiments, steps (a) to (d) is repeated at least 50 times, at least 75 times, at least 100 times, at least 150 times, at least 200 times, at least 250 times, or at least 300 times.

Incorporation Mix

In some embodiments of the method described herein, step (a), also referred to as the incorporation step, includes contacting a mixture containing one or more nucleotides (e.g., dATP, dCTP, dGTP, and dTTP or dUTP) with a copy polynucleotide/target polynucleotide complex in an incorporation solution comprising a polymerase and one or more buffering agents. In some such embodiments, the polymerase is a DNA polymerase, for example, Pol 812, Pol 1901, Pol 1558 or Pol 963. The amino acid sequences of Pol 812, Pol 1901, Pol 1558 or Pol 963 DNA polymerases are described, for example, in U.S. Patent Publication Nos. 2020/0131484 A1 and 2020/0181587 A1, both of which are incorporated by reference herein. In some embodiments, the one or more buffering agents comprise a primary amine, a secondary amine, a tertiary amine, a natural amino acid, or a non-natural amino acid, or combinations thereof. In further embodiments, the buffering agents comprise ethanolamine or glycine, or a combination thereof. In one embodiment, the buffer agent comprises or is glycine. In some embodiments, the use of glycine in the incorporation mix may improve the phasing value, as compared to standard buffering agent such as ethanolamine (EA) at the same condition. For example, the use of glycine provides a reduction or decrease in phasing value of at least 10%, 20%, 30%, 40%, 50%, 60%, 70%, 80%, 90%, 100%, 200%, 300%, 400%, or 500% as compared to as ethanolamine used under the same condition. In some instances, the use of glycine provides a % phasing value of less than about 0.15%, 0.1%, 0.09%, 0.08%, 0.07%, 0.06%, 0.05%, 0.04%, 0.03%, 0.02%, or 0.01% in a SBS sequencing run of at least 50 cycles. In further embodiments, the use of glycine provides a % phasing value of less than about 0.08% in Read 1 of a SBS sequencing run of at least 150 cycles.

Cleavage Mix

In some embodiments of the method described herein, step (c), also referred to as the cleaving step, includes contacting the incorporated nucleotide and the copy polynucleotide strand with a cleavage solution comprising a palladium catalyst described herein. In some such embodiments, the 3'-OH blocking group and the detectable label are removed in a single step of reaction. In one such embodiment, the 3' blocking group is AOM and the cleavable linker comprises AOL moiety, both of which are removed or cleaved in a single step of chemical reaction. In some further embodiments, the cleavage solution (also called cleavage mix) comprises a Pd catalyst described herein.

In some further embodiments, the Pd catalyst is a Pd(0) catalyst. In some such embodiments, the Pd(0) is prepared by mixing a Pd(II) reagent with one or phosphine ligands in situ. In some such embodiments, the palladium catalyst may be prepared by mixing [(Allyl)PdCl]$_2$ with THP in situ. The molar ratio of [(Allyl)PdCl]$_2$ and the THP may be about 1:2, 1:3, 1:4, 1:5, 1:6, 1:7, 1:8, 1:9, or 1:10. In one embodiment, the molar ratio of [(Allyl)PdCl]$_2$ to THP is 1:10 (i.e., the molar ration of Pd:THP is 1:5). In some other embodiment, the palladium catalyst may be prepared by mixing a water soluble Pd(II) reagent Na$_2$PdCl$_4$ with THP in situ. The molar ratio of Na$_2$PdCl$_4$ and THP may be about 1:2, 1:3, 1:4, 1:5, 1:6, 1:7, 1:8, 1:9, or 1:10. In one embodiment, the molar ratio of Na$_2$PdCl$_4$ to THP is about 1:3. In another embodiment, the molar ratio of Na$_2$PdCl$_4$ to THP is about 1:3.5. Other non-limiting examples of a Pd catalyst include Pd(CH$_3$CN)$_2$Cl$_2$.

In some further embodiments, one or more reducing agents may be added, such as ascorbic acid or a salt thereof (e.g., sodium ascorbate). In some embodiments, the cleavage solution may contain one or more buffer reagents, such as a primary amine, a secondary amine, a tertiary amine, a carbonate salt, a phosphate salt, or a borate salt, or combinations thereof. In some further embodiments, the buffer reagents comprise ethanolamine (EA), tris(hydroxymethyl)aminomethane (Tris), glycine, sodium carbonate, sodium phosphate, sodium borate, dimethylethanolamine (DMEA), diethylethanolamine (DEEA), N,N,N',N'-tetramethylethylenediamine(TEMED), N,N,N',N'-tetraethylethylenediamine (TEEDA), or 2-piperidine ethanol, or combinations thereof. In one embodiment, the buffer reagent comprises or is DEEA. In another embodiment, the buffer reagent contains one or more inorganic salts such as a carbonate salt, a phosphate salt, or a borate salt, or combinations thereof. In one embodiment, the inorganic salt is a sodium salt. In further embodiments, the cleavage solution contains an palladium (Pd) catalyst (e.g., [(Allyl)PdCl]$_2$/THP or Na$_2$PdCl$_4$/THP) and one or more buffer reagents described herein (e.g., a tertiary amine such as DEEA) and have pH of about 9.0 to about 10.0 (e.g., 9.6 or 9.8).

In other embodiments, the label and the 3' blocking group are removed in two separate chemical reactions. In some instances, removing the label from the nucleotide incorporated into the copy polynucleotide strand comprises contacting the copy strand including the incorporated nucleotide with a first cleavage solution containing the Pd catalyst described here. In some instances, removing the 3'-OH blocking group from the nucleotide incorporated into the copy polynucleotide strand comprises contacting the copy strand including the incorporated nucleotide with a second cleavage solution. In some such embodiments, the second cleavage solution contains one or more phosphines, such as a trialkylphosphine. None-limiting examples of trialkylphosphines include tris(hydroxypropyl)phosphine (THP), tris-(2-carboxyethyl)phosphine (TCEP), tris(hydroxymethyl)phosphine (THMP), or tris(hydroxyethyl)phosphine (THEP). In one embodiment, the 3'-OH blocking group is 3'-O-azidomethyl and the second cleavage solution contains THP.

In some embodiments, the cleavage solution described herein may also be used in a prior chemical linearization step described herein. In particular, the chemical linearization of clustered polynucleotides in preparation for sequencing is achieved by palladium catalyzed cleavage of one or more first strands of double-stranded polynucleotides immobilized on a solid support, thus generating single-stranded (or at least partially single-stranded) template which will be available for hybridization to a sequencing primer and subsequent sequencing application (e.g., first round of sequencing by synthesis (Read 1)). In some embodiments, each double-stranded polynucleotide comprises a first strand and a second strand. The first strand is generated by extending a first extension primer immobilized to the solid support. In some embodiments, the first strand comprises a cleavage site that is capable being cleaved by a palladium complex (e.g., Pd(0) complex). In a particular embodiment, the cleavage site is located in the first extension primer portion of the first strand. In a further embodiment, the cleavage site comprises a thymine nucleoside or nucleotide analogue having an allyl functionality. In some embodiments of the method described herein, the target single-stranded polynucleotide is formed by chemically cleaving a complementary strand from a double stranded polynucleotide. In further embodiments, both the complementary strand and the target polynucleotide in the double strand are immobilized on the solid support on their 5' end. In some further embodiments, the chemically cleavage of the complementary strand is performed under the same reaction condition as chemically removing the detectable label and the 3'-OH blocking group from the nucleotide incorporated into the copy polynucleotide strand (i.e., step (c) of the method described herein). In one embodiment, the first chemical linearization utilizes the same cleavage mix described herein.

Palladium (Pd) Scavengers

Pd has the capacity to stick on DNA, mostly in its inactive Pd(II) form, which may interfere with the binding between DNA and polymerase, causing increased phasing. A post-cleavage wash composition that includes a Pd scavenger compound may be used following the deblocking step. For example, PCT Publication No. WO 2020/126593 discloses Pd scavengers such as 3,3'-dithiodipropionic acid (DDPA) and lipoic acid (LA) may be included in the scan composition and/or the post-cleavage wash composition. The use of these scavengers in the post-cleave washing solution has the purpose of scavenging Pd(0), converting Pd(0) to the inactive Pd(II) form, thereby improving the prephasing value and sequencing metrics, reducing signal degrade, and extend sequencing read length.

In some embodiments of the methods described herein, step (a) of the method comprises contacting the nucleotide with the copy polynucleotide strand in an incorporation solution comprising a polymerase, at least one palladium scavenger, and one or more buffering agents. In some embodiments, the Pd scavenger in the incorporation solution is a Pd(0) scavenger. In some such embodiments, the Pd scavenger comprises one or more allyl moieties independently selected from the group consisting of —O-allyl, —S-allyl, —NR-allyl, and —N$^+$RR'-allyl, wherein R is H, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted C$_6$-C$_{10}$ aryl, unsubstituted or substituted 5 to 10 membered heteroaryl, unsubstituted or substituted C$_3$-C$_{10}$ carbocyclyl, or unsubstituted or substituted 5 to 10 membered heterocyclyl; and R' is H, unsubstituted C$_1$-C$_6$ alkyl or substituted C$_1$-C$_6$ alkyl.

In some such embodiments, the Pd(0) scavenger in the incorporation solution comprises one or more —O-allyl moieties. In some further embodiments, the Pd(0) scavenger comprises or is

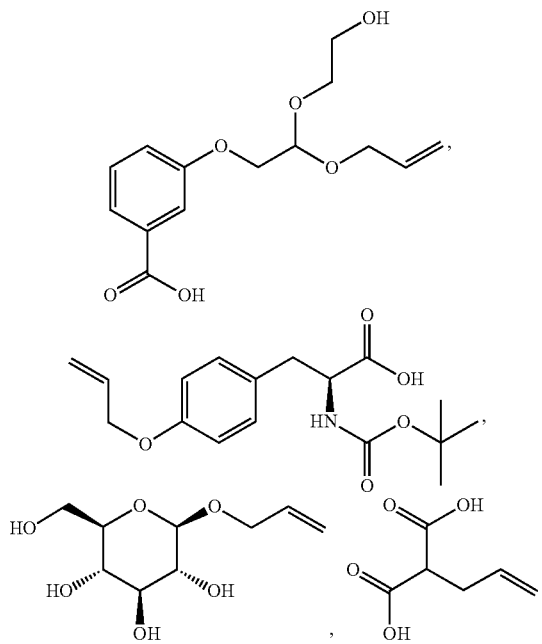

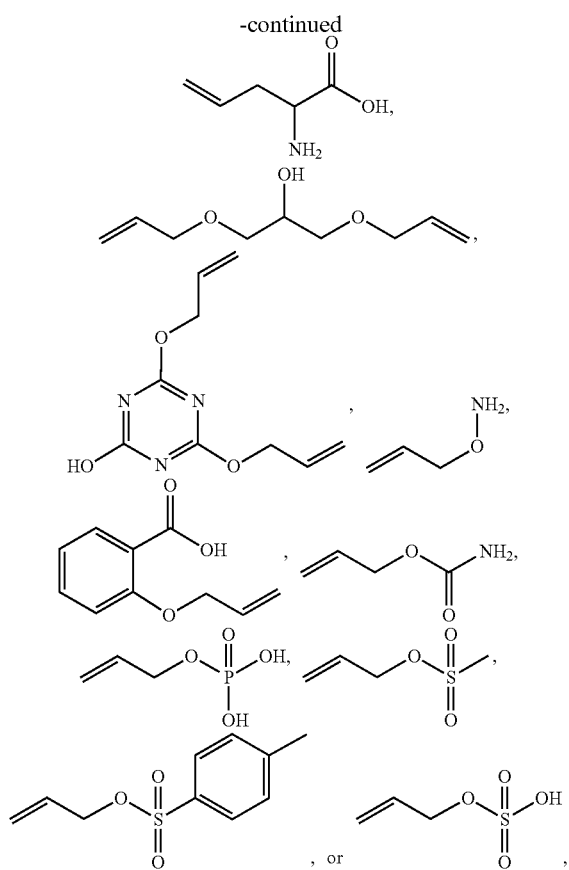

or combinations thereof. Alternative Pd(0) scavengers are disclosed in U.S. Ser. No. 63/190,983, which is incorporated by reference in its entirety.

In some embodiments, the concentration of the Pd(0) scavenger comprising one or more allyl moieties in the incorporation solution is from about 0.1 mM to about 100 mM, from 0.2 mM to about 75 mM, from about 0.5 mM to about 50 mM, from about 1 mM to about 20 mM, or from about 2 mM to about 10 mM. In further embodiments, the concentration of the Pd(0) scavenger is about 0.5 mM, 1 mM, 1.5 mM, 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM, 12.5 mM, 15 mM, 17.5 mM or 20 mM. In further embodiments, the pH of the incorporation solution is about 9-10.

In some embodiments, the molar ratio of the palladium catalyst (in the starting solution) to the palladium scavenger comprising one or more allyl moieties is about 1:100, 1:50, 1:20, 1:10 or 1:5.

In some other embodiments of the methods described herein, the Pd(0) scavenger comprises one or more allyl moieties described herein is in a scanning solution used in step (b) when performing one or more fluorescent measurements to detect the identity of the incorporated nucleotide in the copy polynucleotide. In still other embodiments, the Pd(0) scavenger comprises one or more allyl moieties may be present both in the incorporation solution and in the scanning solution.

In some further embodiments of the method described herein, a post cleavage washing step is used after the label and the 3' blocking group are removed. In some such embodiments, one or more palladium scavengers are also used in the washing step after the cleavage of the label and the 3' blocking group. In some further embodiments, the one or more Pd scavengers in the post-cleavage washing solution comprise Pd(II) scavengers. In some such embodiments, the palladium scavenger comprises an isocyanoacetate (ICNA) salt, cysteine or a salt thereof, or combinations thereof. In one embodiment, the palladium scavenger comprises or is potassium isocyanoacetate or sodium isocyanoacetate. In another embodiment, the palladium scavenger comprises or is cysteine, or a salt thereof (e.g., L-cysteine or L-cysteine HCl salt). Other non-limiting examples of palladium scavenger in the post-cleavage washing solution may include ethyl isocyanoacetate, methyl isocyanoacetate, N-acetyl-L-cysteine, potassium ethylxanthogenate (PEX or KS—C(=S)—OEt), potassium isopropyl xanthate, glutathione, lipoic acid, ethylenediaminetetraacetic acid (EDTA), iminodiacetic acid, nitrilodiacetic acid, trimercapto-S-triazine, dimethyldithiocarbamate, dithiothreitol, mercaptoethanol, allyl alcohol, propargyl alcohol, thiol, tertiary amine and/or tertiary phosphine, or combinations thereof.

In further embodiments, the concentration of the Pd(II) scavenger such as L-cysteine in the post-cleavage washing solution is from about 0.1 mM to about 100 mM, from 0.2 mM to about 75 mM, from about 0.5 mM to about 50 mM, from about 1 mM to about 20 mM, or from about 2 mM to about 10 mM. In further embodiments, the concentration of the Pd(II) scavenger such as L-cysteine is about 1 mM, 2 mM, 3 mM, 4 mM, 5 mM, 6 mM, 6.5 mM, 7 mM, 8 mM, 9 mM, 10 mM, 12.5 mM, 15 mM, 17.5 mM or 20 mM. In one embodiment, the concentration of the Pd scavenger such as L-cysteine or a salt thereof in the post-cleavage washing solution is about 10 mM.

In some other embodiments of the methods described herein, all Pd scavengers (e.g., both Pd(0) and Pd(II) scavengers) are in the incorporation solution and/or the scanning solution, and the method does not include a specific post-cleavage wash step to remove any trace amount of remaining Pd species.

In some embodiments of the methods described herein, the use of the Pd scavengers (e.g., Pd(0) scavenger with one or more allyl moieties) may reduce the prephasing value by at least 10%, 20%, 30%, 40%, 50%, 60%, 70%, 80%, 90%, 100%, 200%, 300%, 400%, 500%, 600%, 700%, 800%, 900%, or 1000%, as compared to the same sequencing run at the same condition without the use of a palladium scavenger. In some such embodiments, the Pd(0) scavenger may reduce the prephasing values of the sequencing run to less than about 0.1%, 0.09%, 0.08%, 0.07%, 0.06%, 0.05%, 0.04%, 0.03%, 0.02% or 0.01% in a SBS sequencing run of at least 50 cycles. In some embodiments, the prephasing value refers to the value measured after 50 cycles, 75 cycles, 100 cycles, 125 cycles, 150 cycles, 200 cycles, 250 cycles, or 300 cycles.

In some further embodiments, the palladium scavengers (e.g., Pd(II) scavenger such as L-cysteine or a salt thereof) may reduce the prephasing value or phasing value by at least 10%, 20%, 30%, 40%, 50%, 60%, 70%, 80%, 90%, 100%, 200%, 300%, 400%, 500%, 600%, 700%, 800%, 900%, or 1000%, as compared to the same sequencing run at the same condition without the use of a palladium scavenger. In some such embodiments, the use of a Pd scavenger provides a % phasing value of less than about 0.2%, 0.15%, 0.1%, 0.09%, 0.08%, 0.07%, 0.06%, 0.05%, 0.04%, 0.03%, 0.02%, or 0.01% in a SBS sequencing run of at least 50 cycles. In some embodiments, the phasing value refers to the value measured after 50 cycles, 75 cycles, 100 cycles, 125 cycles, 150 cycles, 200 cycles, 250 cycles, or 300 cycles. In further embodiments, the use of one or more Pd scavengers provides a % phasing value of less than about 0.05% in Read 1 of a SBS sequencing run of at least 150 cycles.

In some embodiment, the post washing solution described herein may also be used in a separate washing step before the detecting step (i.e., step (b) in the method described herein) to wash away any unincorporated nucleotides from step (a).

In some further embodiments, the nucleotides used in the incorporation step (a) are fully functionalized A, C, T and G nucleotide triphosphate each contains a 3'blocking group described herein (e.g., 3'-AOM) and a cleavable linker (e.g., a cleavable linker containing AOL linker moiety). In some such embodiments, the nucleotides herein provide superior stability in solution during sequencing runs, compared to the same nucleotides protected with a standard 3'-O-azidomethyl blocking group. For example, the 3' acetal blocking groups disclosed herein may confer at least 5%, 10%, 20%, 30%, 40%, 50%, 60%, 70%, 80%, 90%, 100%, 200%, 300%, 400%, 500%, 600%, 700%, 800%, 900%, 1000%, 1500%, 2000%, 2500%, or 3000% improved stability compare to an azidomethyl protected 3'-OH at the same condition for the same period of time, thereby reducing the pre-phasing values and resulting in longer sequencing read lengths. In some embodiments, the stability is measured at ambient temperature or a temperature below ambient temperature (such as 4-10° C.). In other embodiments, the stability is measured at an elevated temperature, such as 40° C., 45° C., 50° C., 55° C., 60° C. or 65° C. In some such embodiments, the stability is measured in solution in a basic pH environment, e.g., at pH 9.0, 9.2, 9.4, 9.6, 9.8. or 10.0. In some further embodiments, the pre-phasing value with the 3' blocked nucleotide described herein is less than about 0.25, 0.24, 0.23, 0.22, 0.21, 0.20, 0.19, 0.18, 0.17, 0.16, 0.15, 0.14, 0.13, 0.12, 0.11, 0.10, 0.09, 0.08, 0.07, 0.06, or 0.05 after over 50, 100 or 150 cycles of SBS. In some further embodiments, the phasing value with the 3' blocked nucleotide is less than about 0.25, 0.24, 0.23, 0.22, 0.21, 0.20, 0.19, 0.18, 0.17, 0.16, 0.15, 0.14, 0.13, 0.12, 0.11, 0.10, 0.09, 0.08, 0.07, 0.06, or 0.05, after over 50, 100 or 150 cycles of SBS. In one embodiment, each ffN contains the 3'-AOM group.

In some embodiments, the 3' blocked nucleotides described herein provide superior deblocking rate in solution during the chemical cleavage step of the sequencing run, compared to the same nucleotides protected with a standard 3'-O-azidomethyl blocking group. For example, the 3' acetal (e.g., AOM) blocking groups disclosed herein may confer at least 5%, 10%, 20%, 30%, 40%, 50%, 60%, 70%, 80%, 90%, 100%, 150%, 200%, 300%, 400%, 500%, 600%, 700%, 800%, 900%, 1000%, 1500%, or 2000% improved deblocking rate compare to an azidomethyl protected 3'-OH using the standard deblocking reagent (such as tris(hydroxypropyl)phosphine), thereby reducing the overall time for a sequencing cycle. In some embodiments, the deblocking time for each nucleotide is reduced by about 5%, 10%, 20%, 30%, 40%, 50%, or 60%. For example, the deblocking time for 3'-AOM and 3'-O-azidomethyl is about 4-5 seconds and about 9-10 seconds respectively under certain chemical reaction condition. In some embodiments, the half life ($t_{1/2}$) of AOM blocking group is at least 1, 2, 3, 4, 5, 6, 7, 8, 9 or 10-fold faster than azidomethyl blocking group. In some such embodiment, $t_{1/2}$ of AOM is about 1 minute while $t_{1/2}$ of azidomethyl is about 11 minutes. In some embodiments, the deblocking rate is measured at ambient temperature or a temperature below ambient temperature (such as 4-10° C.). In other embodiments, the deblocking rate is measured at an elevated temperature, such as 40° C., 45° C., 50° C., 55° C., 60° C. or 65° C. In some such embodiments, the deblocking rate is measured in solution in a basic pH environment, e.g., at pH 9.0, 9.2, 9.4, 9.6, 9.8. or 10.0. In some such embodiments, the molar ratio of the deblocking reagent to substrate (i.e., 3' blocked nucleoside or nucleotide) is about 10:1, about 5:1, about 2:1, about 1:1, about 1:2, about 1:5 or about 1:10. In one embodiment, each ffN contains the 3'-AOM blocking group and AOL linker moiety.

In any embodiments of the methods described herein, the labeled nucleotide is a nucleotide triphosphate having 2' deoxyribose. In any embodiments of the method described herein, the target polynucleotide strand is attached to a solid support, such as a flow cell.

In one embodiment, at least one nucleotide is incorporated into a polynucleotide in the synthetic step by the action of a polymerase enzyme. In some such embodiments, the polymerase may be DNA polymerase Pol 812 or Pol 1901. However, other methods of joining nucleotides to polynucleotides, such as, for example, chemical oligonucleotide synthesis or ligation of labeled oligonucleotides to unlabeled oligonucleotides, can be used. Therefore, the term "incorporating," when used in reference to a nucleotide and polynucleotide, can encompass polynucleotide synthesis by chemical methods as well as enzymatic methods.

In a specific embodiment, a synthetic step is carried out and may optionally comprise incubating a template polynucleotide strand with a reaction mixture comprising labeled 3' blocked nucleotides of the disclosure. A polymerase can also be provided under conditions which permit formation of a phosphodiester linkage between a free 3'-OH group on a polynucleotide strand annealed to the template polynucleotide strand and a 5' phosphate group on the nucleotide. Thus, a synthetic step can include formation of a polynucleotide strand as directed by complementary base-pairing of nucleotides to a template strand.

In all embodiments of the methods, the detection step may be carried out while the polynucleotide strand into which the labeled nucleotides are incorporated is annealed to a template or target strand, or after a denaturation step in which the two strands are separated. Further steps, for example chemical or enzymatic reaction steps or purification steps, may be included between the synthetic step and the detection step. In particular, the target strand incorporating the labeled nucleotide(s) may be isolated or purified and then processed further or used in a subsequent analysis. By way of example, target polynucleotides labeled with nucleotide(s) as described herein in a synthetic step may be subsequently used as labeled probes or primers. In other embodiments, the product of the synthetic step set forth herein may be subject to further reaction steps and, if desired, the product of these subsequent steps purified or isolated.

Suitable conditions for the synthetic step will be well known to those familiar with standard molecular biology techniques. In one embodiment, a synthetic step may be analogous to a standard primer extension reaction using nucleotide precursors, including nucleotides as described herein, to form an extended target strand complementary to the template strand in the presence of a suitable polymerase enzyme. In other embodiments, the synthetic step may itself form part of an amplification reaction producing a labeled double stranded amplification product comprised of annealed complementary strands derived from copying of the target and template polynucleotide strands. Other exemplary synthetic steps include nick translation, strand displacement polymerization, random primed DNA labeling, etc. A particularly useful polymerase enzyme for a synthetic step is one that is capable of catalyzing the incorporation of nucleotides as set forth herein. A variety of naturally occurring or modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the nucleotides according to the disclosure include those described in WO 2005/024010 or WO 06/120433, each of which is incorporated herein by reference. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the disclosure encompasses methods of nucleic acid sequencing, re-sequencing, whole genome sequencing, single nucleotide polymorphism scoring, any other application involving the detection of the labeled nucleotide or nucleoside set forth herein when incorporated into a polynucleotide. Any of a variety of other applications benefiting the use of polynucleotides labeled with the nucleotides comprising fluorescent dyes can use labeled nucleotides or nucleosides with dyes set forth herein.

In a particular embodiment, the disclosure provides use of labeled nucleotides according to the disclosure in a polynucleotide sequencing-by-synthesis (SBS) reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the labeled nucleotides set forth herein for determination of the identity of a single base may be useful, for example, in the scoring of single nucleotide polymorphisms, and such single base extension reactions are within the scope of this disclosure.

In an embodiment of the present disclosure, the sequence of a template polynucleotide is determined by detecting the incorporation of one or more 3' blocked nucleotides described herein into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments, each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template polynucleotide, and the blocking group prevents further incorporation of nucleotides. Any unincorporated nucleotides can be washed away and the fluorescent signal from each incorporated nucleotide can be "read" optically by suitable means, such as a charge-coupled device using laser excitation and suitable emission filters. The 3'-blocking group and fluorescent dye compounds can then be removed (deprotected) simultaneously or sequentially to expose the nascent chain for further nucleotide incorporation. Typically, the identity of the incorporated nucleotide will be determined after each incorporation step, but this is not strictly essential. Similarly, U.S. Pat. No. 5,302,509 (which is incorporated herein by reference) discloses a method to sequence polynucleotides immobilized on a solid support.

The method, as exemplified above, utilizes the incorporation of fluorescently labeled, 3'-blocked nucleotides A, G, C, and T into a growing strand complementary to the immobilized polynucleotide, in the presence of DNA polymerase. The polymerase incorporates a base complementary to the target polynucleotide but is prevented from further addition by the 3'-blocking group. The label of the incorporated nucleotide can then be determined, and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3'-OH group that serves as a primer or initiation point for the addition of further nucleotides in the sequencing reaction. The region of the template to be sequenced will overhang this free 3'-OH group on the complementary strand. The overhanging region of the template to be sequenced may be single stranded but can be double-stranded, provided that a "nick is present" on the strand complementary to the template strand to be sequenced to provide a free 3'-OH group for initiation of the sequencing reaction. In such embodiments, sequencing may proceed by strand displacement. In certain embodiments, a primer bearing the free 3'-OH group may be added as a separate component (e.g., a short oligonucleotide) that hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO 01/57248 and WO 2005/047301, each of which is incorporated herein by reference. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3'-OH group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments, the nucleic acid template to be sequenced may be attached to a solid support via any suitable linkage method known in the art, for example via covalent attachment. In certain embodiments template polynucleotides may be attached directly to a solid support (e.g., a silica-based support). However, in other embodiments of the disclosure the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Embodiments and Alternatives of Sequencing-by-Synthesis

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." *Science* 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina, Inc.), and is also described in WO 91/06678 and WO 07/123,744, each of which is incorporated herein by reference. The availability of fluorescently-labeled terminators in which both the termination can be reversed, and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially, and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed, and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

Some embodiments can utilize detection of four different nucleotides using fewer than four different labels. For example, SBS can be performed utilizing methods and systems described in the incorporated materials of U.S. Pub. No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." *Trends Biotechnol.* 18, 147-151 (2000); Deamer, D. and D. Branton, "Characterization of nucleic acids by nanopore analysis", *Acc. Chem. Res.* 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as $\alpha$-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." *Clin. Chem.* 53, 1996-2001 (2007); Healy, K. "Nanopore-based single-molecule DNA analysis." *Nanomed.* 2, 459-481 (2007); Cockroft, S. L., Chu, J., Amorin, M. & Ghadiri, M. R. "A single-molecule nanopore device detects DNA polymerase activity with single-nucleotide resolution." *J. Am. Chem. Soc.* 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some other embodiments of sequencing method involve the use the 3' blocked nucleotide described herein in nanoball sequencing technique, such as those described in U.S. Pat. No. 9,222,132, the disclosure of which is incorporated by reference. Through the process of rolling circle amplification (RCA), a large number of discrete DNA nanoballs may be generated. The nanoball mixture is then distributed onto a patterned slide surface containing features that allow a single nanoball to associate with each location. In DNA nanoball generation, DNA is fragmented and ligated to the first of four adapter sequences. The template is amplified, circularized and cleaved with a type II endonuclease. A second set of adapters is added, followed by amplification, circularization and cleavage. This process is repeated for the remaining two adapters. The final product is a circular template with four adapters, each separated by a template sequence. Library molecules undergo a rolling circle amplification step, generating a large mass of concatemers called DNA nanoballs, which are then deposited on a flow cell. Goodwin et al., "Coming of age: ten years of next-generation sequencing technologies," Nat Rev Genet. 2016; 17(6): 333-51.

Some embodiments can utilize methods involving the real-time monitoring of DNA polymerase activity. Nucleotide incorporations can be detected through fluorescence resonance energy transfer (FRET) interactions between a fluorophore-bearing polymerase and $\gamma$-phosphate-labeled nucleotides as described, for example, in U.S. Pat. Nos. 7,329,492 and 7,211,414, both of which are incorporated herein by reference, or nucleotide incorporations can be detected with zero-mode waveguides as described, for example, in U.S. Pat. No. 7,315,019, which is incorporated herein by reference, and using fluorescent nucleotide analogs and engineered polymerases as described, for example, in U.S. Pat. No. 7,405,281 and U.S. Pub. No. 2008/0108082, both of which are incorporated herein by reference. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." *Science* 299, 682-686 (2003); Lundquist, P. M. et al. "Parallel confocal detection of single molecules in real time." *Opt. Lett.* 33, 1026-1028 (2008); Korlach, J. et al. "Selective aluminum passivation for targeted immobilization of single DNA polymerase molecules in zero-mode waveguide nano structures." *Proc. Natl. Acad. Sci. USA* 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Pub. Nos. 2009/0026082; 2009/0127589; 2010/0137143; and 2010/0282617, all of which are incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An advantage of the methods set forth herein is that they provide for rapid and efficient detection of a plurality of target nucleic acid in parallel. Accordingly, the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Pub. No. 2010/0111768 and U.S. patent application Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. patent application Ser. No. 13/273,666, which is incorporated herein by reference.

Arrays in which polynucleotides have been directly attached to silica-based supports are those for example disclosed in WO 00/06770 (incorporated herein by reference), wherein polynucleotides are immobilized on a glass support by reaction between a pendant epoxide group on the glass with an internal amino group on the polynucleotide. In addition, polynucleotides can be attached to a solid support by reaction of a sulfur-based nucleophile with the solid support, for example, as described in WO 2005/047301 (incorporated herein by reference). A still further example of solid-supported template polynucleotides is where the template polynucleotides are attached to hydrogel supported upon silica-based or other solid supports, for example, as described in WO 00/31148, WO 01/01143, WO 02/12566, WO 03/014392, U.S. Pat. No. 6,465,178 and WO 00/53812, each of which is incorporated herein by reference.

A particular surface to which template polynucleotides may be immobilized is a polyacrylamide hydrogel. Polyacrylamide hydrogels are described in the references cited above and in WO 2005/065814, which is incorporated herein by reference. Specific hydrogels that may be used include those described in WO 2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles, for example, as described in U.S. Pat. No. 6,172,218 (which is incorporated herein by reference). Attachment to beads or microparticles can be useful for sequencing applications. Bead libraries can be prepared where each bead contains different DNA sequences. Exemplary libraries and methods for their creation are described in *Nature*, 437, 376-380 (2005); *Science*, 309, 5741, 1728-1732 (2005), each of which is incorporated herein by reference. Sequencing of arrays of such beads using nucleotides set forth herein is within the scope of the disclosure.

Templates that are to be sequenced may form part of an "array" on a solid support, in which case the array may take any convenient form. Thus, the method of the disclosure is applicable to all types of high-density arrays, including single-molecule arrays, clustered arrays, and bead arrays. Labeled nucleotides of the present disclosure may be used for sequencing templates on essentially any type of array, including but not limited to those formed by immobilization of nucleic acid molecules on a solid support.

However, labeled nucleotides of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g., the site is homogenous for a particular single- or double-stranded nucleic acid species) or even multiple copies of a small number of different polynucleotide molecules (e.g., multiple copies of two different nucleic acid species). Clustered arrays of nucleic acid molecules may be produced using techniques generally known in the art. By way of example, WO 98/44151 and WO 00/18957, each of which is incorporated herein, describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using the nucleotides labeled with dye compounds of the disclosure.

The labeled nucleotides of the present disclosure are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilized onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to published applications WO 00/06770 and WO 01/57248, each of which is incorporated herein by reference. Although one use of the nucleotides of the disclosure is in sequencing-by-synthesis reactions, the utility of the nucleotides is not limited to such methods. In fact, the nucleotides may be used advantageously in any sequencing methodology which requires detection of fluorescent labels attached to nucleotides incorporated into a polynucleotide.

In particular, the labeled nucleotides of the disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So-called Sanger sequencing methods, and related protocols (Sanger-type), utilize randomized chain termination with labeled dideoxynucleotides.

Thus, the present disclosure also encompasses labeled nucleotides which are dideoxynucleotides lacking hydroxyl groups at both of the 3' and 2' positions, such dideoxynucleotides being suitable for use in Sanger type sequencing methods and the like.

Labeled nucleotides of the present disclosure incorporating 3' blocking groups, it will be recognized, may also be of utility in Sanger methods and related protocols since the same effect achieved by using dideoxy nucleotides may be achieved by using nucleotides having 3'-OH blocking groups: both prevent incorporation of subsequent nucleotides. Where nucleotides according to the present disclosure, and having a 3' blocking group are to be used in Sanger-type sequencing methods it will be appreciated that the dye compounds or detectable labels attached to the nucleotides need not be connected via cleavable linkers, since in each instance where a labeled nucleotide of the disclosure is incorporated; no nucleotides need to be subsequently incorporated and thus the label need not be removed from the nucleotide.

In any embodiments of the SBS methods described herein, the nucleotide used in the sequencing application is a 3' blocked nucleotide described herein, for example, the nucleotide of Formula (I) and (Ia)-(Id). In any embodiments, the 3' blocked nucleotide is a nucleotide triphosphate.

In certain sequencing methods, the incorporated nucleotide is unlabeled. One or more fluorescent labels may be introduced after incorporation by using labeled affinity reagents containing one or more fluorescent dyes. For example, one, two, three or each of the four different types of nucleotides (e.g., dATP, dCTP, dGTP and dTTP or dUTP) in the incorporation buffer of step (a) may be unlabeled. Each of the four types of nucleotides (e.g., dNTPs) has a 3'-OH blocking group described herein (e.g, 3'-AOM) to ensure that only a single base can be added by a polymerase to the 3' end of the copy polynucleotide. After incorporation of an unlabeled nucleotide, an affinity reagent is then introduced that specifically binds to the incorporated dNTP to provide a labeled extension product comprising the incorporated dNTP. Uses of unlabeled nucleotides and affinity reagents in sequencing by synthesis have been disclosed in U.S. Publication No. 2013/0079232. A modified sequencing method of the present disclosure using unlabeled nucleotides may include the following steps:

(a'-1) incorporating an unlabeled nucleotide (e.g., dATP, dCTP, dGTP, dTTP or dUTP) comprising a 3'-OH blocking group

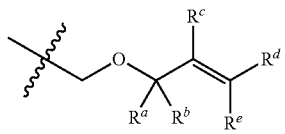

described herein (attached to the 3' oxygen) into a copy polynucleotide strand complementary to at least a portion of the target polynucleotide strand to produce an extended copy polynucleotide;

(a'-2) contacting the extended copy polynucleotide with a set of affinity reagents under conditions wherein one affinity reagent binds specifically to the incorporated unlabeled nucleotide to provide a labeled extended copy polynucleotide;

(b') detecting the identity of the nucleotide incorporated into the copy polynucleotide strand by performing one or more fluorescent measurements of the labeled extended copy polynucleotide; and (c') chemically removing the detectable label from the extended copy polynucleotide and the 3'-OH blocking group from the nucleotide incorporated into the copy polynucleotide strand.

The affinity reagents may include small molecules or protein tags that may bind to a hapten moiety of the nucleotide (such as streptavidin-biotin, anti-DIG and DIG, anti-DNP and DNP), antibody (including but not limited to binding fragments of antibodies, single chain antibodies, bispecific antibodies, and the like), aptamers, knottins, affimers, or any other known agent that binds an incorporated nucleotide with a suitable specificity and affinity. In further embodiments, one affinity reagent may be labeled with multiple copies of the same fluorescent dyes. In some embodiments, the Pd catalyst also removes the labeled affinity reagent. For example, the hapten moiety of the unlabeled nucleotide may be attached to the nucleobase through a cleavable linker

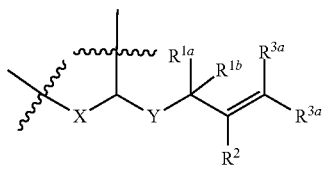

as described herein (e.g., the AOL linker), which may be cleaved by the Pd catalyst. In some embodiments, the method further comprises a post-cleavage washing step (d) described herein. In some embodiments, the method further comprises repeating steps (a'-1) through (c') or (a'-1) through (d) until a sequence of at least a portion of the target polynucleotide strand is determined. In some embodiments, the cycle is repeated at least 50 times, at least 100 times, at least 150 times, at least 200 times, at least 250 times, or at least 300 times.

Kits

The present disclosure also provides kits including one or more 3' blocked nucleosides and/or nucleotides described herein, for example, the 3' blocked nucleotide of Formula (I) and (Ia)-(Id). Such kits will generally include at least one 3' blocked nucleotide or nucleoside comprising a detectable label (e.g., a fluorescent dye) with at least one further component. The further component(s) may be one or more of the components identified in a method set forth herein or in the Examples section below. Some non-limiting examples of components that can be combined into a kit of the present disclosure are set forth below. In some further embodiment, the kit may comprise four types of labeled nucleotides of fully functionalized nucleotides described herein (A, C, T and G), where each type of nucleotide comprises the 3'-AOM blocking group and the AOL linker moiety described herein. In further embodiments, G is unlabeled and does not comprises the AOL linker. In still further embodiments, one or more the remaining three nucleotides (i.e., A, C and T) comprises $L^1$ being the allylamine or allylamide linker moiety. In one embodiment, the kit comprises unlabeled ffG, labeled ffA(s), labeled ffC, and labeled ffT-DB described herein. In another embodiment, the kit comprises unlabeled ffG, labeled ffA(s), labeled ffC-DB, and labeled ffT-DB described herein.

In a particular embodiment, a kit can include at least one labeled 3' blocked nucleotide or nucleoside together with labeled or unlabeled nucleotides or nucleosides. For example, nucleotides labeled with dyes may be supplied in combination with unlabeled or native nucleotides, and/or with fluorescently labeled nucleotides or any combination thereof. Combinations of nucleotides may be provided as separate individual components (e.g., one nucleotide type per vessel or tube) or as nucleotide mixtures (e.g., two or more nucleotides mixed in the same vessel or tube).

Where kits comprise a plurality, particularly two, or three, or more particularly four, 3' blocked nucleotides labeled with a dye compound, the different nucleotides may be labeled with different dye compounds, or one may be dark, with no dye compounds. Where the different nucleotides are labeled with different dye compounds, it is a feature of the kits that the dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary-based DNA sequencing platform) when two or more such dyes are present in one sample. When two nucleotides labeled with fluorescent dye compounds are supplied in kit form, it is a feature of some embodiments that the spectrally distinguishable fluorescent dyes can be excited at the same wavelength, such as, for example by the same laser. When four 3' blocked nucleotides (A, C, T, and G) labeled with fluorescent dye compounds are supplied in kit form, it is a feature of some embodiments that two of the spectrally distinguishable fluorescent dyes can both be excited at one wavelength and the other two spectrally distinguishable dyes can both be excited at another wavelength. Particular excitation wavelengths are 488 nm and 532 nm.

In one embodiment, a kit includes a first 3' blocked nucleotide labeled with a first dye and a second nucleotide labeled with a second dye wherein the dyes have a difference in absorbance maximum of at least 10 nm, particularly 20 nm to 50 nm. More particularly, the two dye compounds have Stokes shifts of between 15-40 nm where "Stokes shift" is the distance between the peak absorption and peak emission wavelengths.

In an alternative embodiment, the kits of the disclosure may contain 3' blocked nucleotides where the same base is labeled with two or more different dyes. A first nucleotide (e.g., 3' blocked T nucleotide triphosphate or 3' blocked G nucleotide triphosphate) may be labeled with a first dye. A second nucleotide (e.g., 3' blocked C nucleotide triphosphate) may be labeled with a second spectrally distinct dye from the first dye, for example a "green" dye absorbing at less than 600 nm, and a "blue" dye absorbs at less than 500 nm, for example 400 nm to 500, in particular 450 nm to 460 nm). A third nucleotide (e.g., 3' blocked A nucleotide triphosphate) may be labeled as a mixture of the first and the second dyes, or a mixture of the first, the second and a third dyes, and the fourth nucleotide (e.g., 3' blocked G nucleotide triphosphate or 3' blocked T nucleotide triphosphate) may be 'dark' and contain no label. In one example, the nucleotides 1-4 may be labeled 'blue', 'green', 'blue/green', and dark. To simplify the instrumentation further, four nucleotides can be labeled with two dyes excited with a single laser, and thus the labeling of nucleotides 1-4 may be 'blue 1', 'blue 2', 'blue 1/blue 2', and dark.

In particular embodiments, the kits may contain four labeled 3' blocked nucleotides (e.g., A, C, T, G), where each type of nucleotide comprises the same 3' blocking group and a fluorescent label, and wherein each fluorescent label has a distinct fluorescence maximum and each of the fluorescent labels is distinguishable from the other three labels. The kits may be such that two or more of the fluorescent labels have a similar absorbance maximum but different Stokes shift. In some other embodiments, one type of the nucleotide is unlabeled.

Although kits are exemplified herein in regard to configurations having different nucleotides that are labeled with different dye compounds, it will be understood that kits can include 2, 3, 4 or more different nucleotides that have the same dye compound. In some embodiments, the kit also includes an enzyme and a buffer appropriate for the action of the enzyme. In some such embodiments, the enzyme is a polymerase, a terminal deoxynucleotidyl transferase, or a reverse transcriptase. In particular embodiments, the enzyme is a DNA polymerase, such as DNA polymerase 812 (Pol 812) or DNA polymerase 1901 (Pol 1901). In some further embodiment, the kit may comprise an incorporation mix described herein. In further embodiments, the kit containing the incorporation mix described herein also comprises at least one Pd scavenger (e.g., the Pd(0) scavenger described herein that comprises one or more allyl moieties). In the Pd(0) scavenger comprises one or more allyl moieties each independently selected from the group consisting of —O-allyl, —S-allyl, —NR-allyl, and —N⁺RR'-allyl, wherein R is H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_6$-$C_{10}$ aryl, unsubstituted or substituted 5 to 10 membered heteroaryl, unsubstituted or substituted $C_3$-$C_{10}$ carbocyclyl, or unsubstituted or substituted 5 to 10 membered heterocyclyl; and R' is H, unsubstituted $C_1$-$C_6$ alkyl or substituted $C_1$-$C_6$ alkyl. In some such embodiments, the Pd(0) scavenger in the incorporation solution comprises one or more —O-allyl moieties. In some further embodiments, the Pd(0) scavenger comprises or is

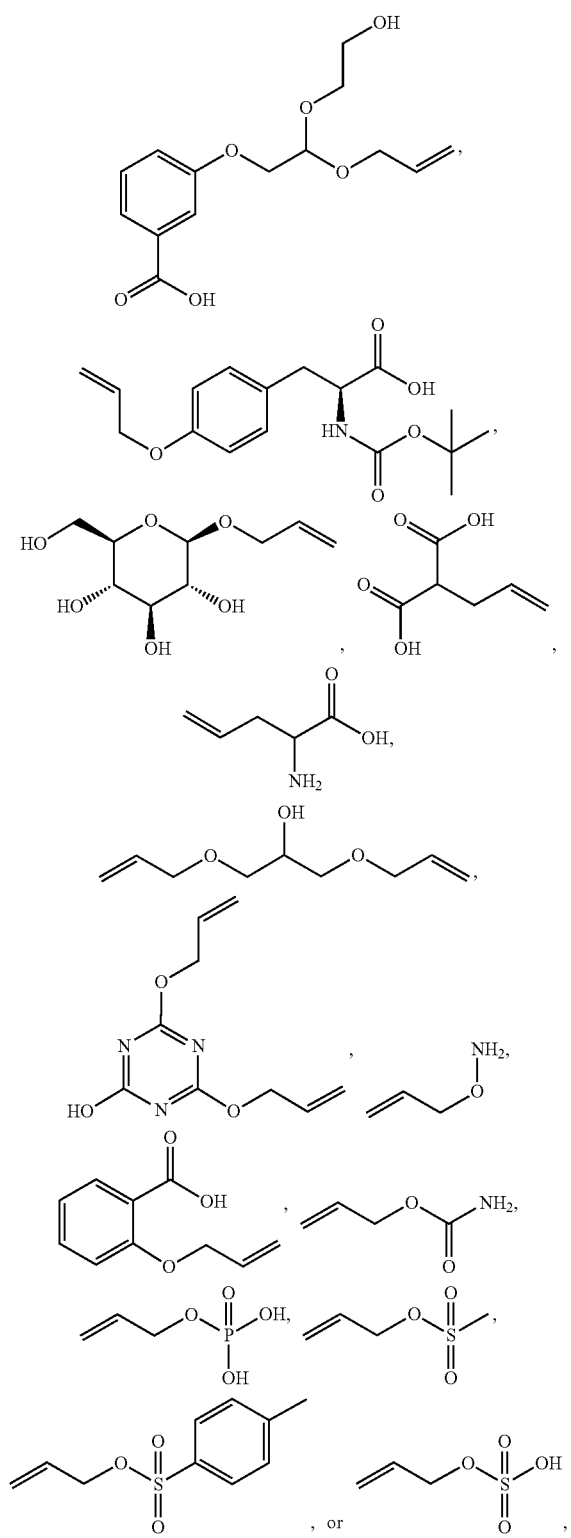

or combinations thereof. Alternative Pd(0) scavengers are disclosed in U.S. Ser. No. 63/190,983, which is incorporated by reference in its entirety. In one embodiment, the Pd(0) scavenger in the incorporation mix comprises or is

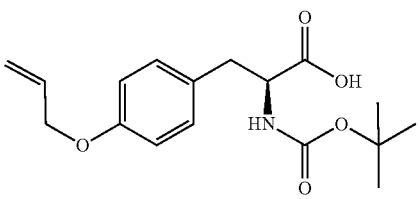

In another embodiment, the Pd(0) scavenger in the incorporation mix comprises or is

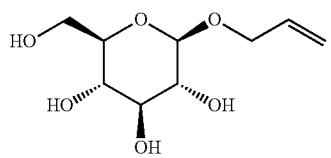

Other components to be included in such kits may include buffers and the like. The nucleotides of the present disclosure, and other any nucleotide components including mixtures of different nucleotides, may be provided in the kit in a concentrated form to be diluted prior to use. In such embodiments a suitable dilution buffer may also be included. For example, the incorporation mix kit may comprise one or more buffering agents selected from a primary amine, a secondary amine, a tertiary amine, a natural amino acid, or a non-natural amino acid, or combinations thereof. In further embodiments, the buffering agents in the incorporation mix comprise ethanolamine or glycine, or a combination thereof.

Again, one or more of the components identified in a method set forth herein can be included in a kit of the present disclosure. In some further embodiments, the kit may comprise a palladium catalyst described herein. In some embodiments, the Pd catalyst is generated by mixing a Pd(II) complex (i.e., a Pd pre-catalyst) with one or more water soluble phosphines described herein. In some such embodiments, the kit containing the Pd catalyst is the cleavage mix kit. In further embodiments, the cleavage mix kit may contain Pd(Allyl)Cl]$_2$ or Na$_2$PdCl$_4$ and a water soluble phosphine THP to generate the active Pd(0) species. The molar ratio of Pd(II) complex (e.g., Pd(Allyl)Cl]$_2$ or Na$_2$PdCl$_4$) to the water soluble phosphine (e.g., THP) may be about 1:2, 1:3, 1:4, 1:5, 1:6, 1:7, 1:8, 1:9, or 1:10. In further embodiments, the cleavage mix kit may also contain one or more buffer reagents selected from the group consisting of a primary amine, a secondary amine, a tertiary amine, a carbonate salt, a phosphate salt, and a borate salt, and combinations thereof. Non-limiting example of the buffer reagents in the cleavage mix kit are selected from the group consisting of ethanolamine (EA), tris(hydroxymethyl) aminomethane (Tris), glycine, a carbonate salt, a phosphate salt, a borate salt, dimethylethanolamine (DMEA), diethylethanolamine (DEEA), N,N,N',N'-tetramethylethylenediamine (TEMED), and N,N,N',N'-tetraethylethylenediamine (TEEDA), 2-piperidine ethanol, and combinations thereof. In one embodiment, the cleavage mix kit contains DEEA. In other embodiment, the cleavage mix kit contains 2-piperidine ethanol.

In some further embodiments, the kit may comprise one or more palladium scavengers (e.g., a Pd(II) scavenger described herein). In some such embodiments, the kit is the post-cleavage washing buffer kit. Non-limiting examples of the Pd scavengers in the post-cleavage washing buffer kit include an isocyanoacetate (ICNA) salt, ethyl isocyanoacetate, methyl isocyanoacetate, cysteine or a salt thereof, L-cysteine or a salt thereof, N-acetyl-L-cysteine, potassium ethylxanthogenate, potassium isopropyl xanthate, glutathione, lipoic acid, ethylenediaminetetraacetic acid (EDTA), iminodiacetic acid, nitrilodiacetic acid, trimercapto-S-triazine, dimethyldithiocarbamate, dithiothreitol, mercaptoethanol, allyl alcohol, propargyl alcohol, thiol, tertiary amine and/or tertiary phosphine, or combinations thereof. In one embodiment, the post-cleavage washing buffer kit comprises L-cysteine or a salt thereof.

In any embodiments of the kits described herein, the Pd scavengers (e.g. the Pd(0) or Pd(II) scavengers described herein) are in separate containers/compartments from the Pd catalyst.

EXAMPLES

Additional embodiments are disclosed in further detail in the following examples, which are not in any way intended to limit the scope of the claims.

Example 1. Synthesis of Fully Functionalized Nucleotides with 3'AOM and AOL Linker Moiety mmol). The mixture was stirred at 0° C. for 2 hours, then allyl alcohol (13 mL, 191.1 mmol) was added and the reaction was refluxed overnight. The reaction was quenched with a 98:2 mixture of MeOH/$H_2O$, and the resulting solution was additionally stirred for 3 hours at RT. The mixture was diluted with $CH_2Cl_2$ (100 mL) and water (200 mL), and the aqueous layer was acidified with 2N HCl to pH 2-3. The aqueous layer was separated, and the organic layer was additionally extracted with acidic water. The organic layer was dried over $MgSO_4$, filtered and the volatiles were evaporated under reduced pressure. The crude product was purified by flash chromatography on silica gel to give AOL LN2 as a colorless oil (2.56 g, 86%).

Synthesis of Intermediate AOL LN3:

To a solution of AOL LN2 (2.17 g, 7.0 mmol) in ethanol (17.5 mL) was added 4M aqueous NaOH (17.5 mL, 70 mmol) and the mixture was stirred for 3 hours at RT. After this time, all the volatiles were removed under reduced pressure and the residue was dissolved in 75 mL water. The solution was acidified with 2 N HCl to pH 2-3 and then extracted with dichloromethane (DCM). The combined organic fractions were dried over $MgSO_4$, filtered and the volatiles were evaporated under reduced pressure. AOL LN3, was obtained without further purification as colorless

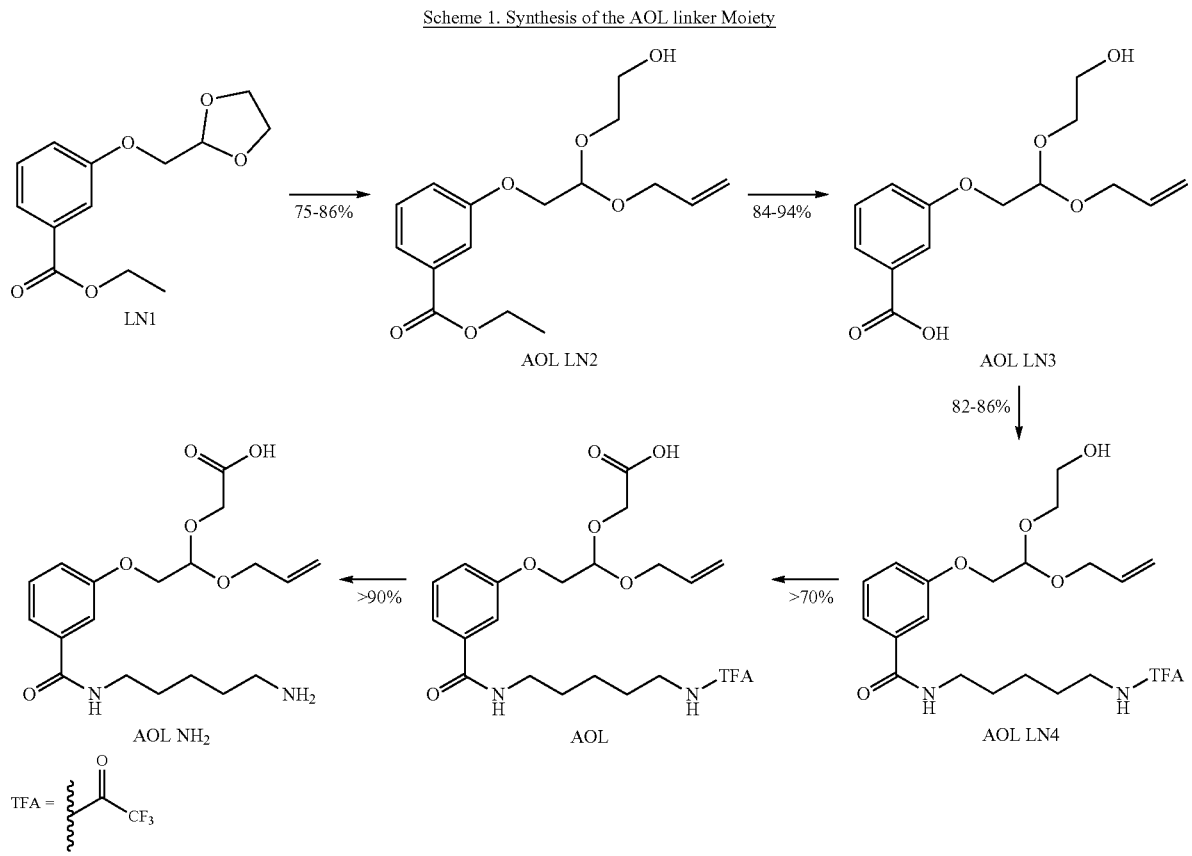

Scheme 1. Synthesis of the AOL linker Moiety

Synthesis of Intermediate AOL LN2:

Acetal compound LN1 (2.43 g, 9.6 mmol) was dissolved in anhydrous $CH_2Cl_2$ (100 mL) under $N_2$ and the solution was cooled to 0° C. with an ice bath. 2,4.6-Trimethylpyridine (7.6 mL, 57.5 mmol) was added, followed by dropwise trimethylsilyl trifluoromethanesulfonate (7.0 mL, 38.7 oil that solidify upon storage at −20° C. (1.65 g, 84%). LC-MS (ES): (negative ion) m/z 281 (M−H$^+$); (positive ion) m/z 305 (M+Na$^+$).

Synthesis of Intermediate AOL LN4:

A solution of AOL LN3 (1.62 g, 5.74 mmol) in anhydrous DMF (20 mL) was stirred under vacuum for 5 min, before being cooled to 0° C. with an ice bath. N,N-Diisopropyl-ethylamine (1.2 mL, 6.89 mmol) was added dropwise under $N_2$, followed by PyBOP (3.30 g, 6.34 mmol). The reaction was stirred at 0° C. for 30 min, then a solution of N-(5-aminopentyl)-2,2,2-trifluoroacetamide hydrochloride salt (1.62 g, 6.90 mmol) in anhydrous DMF (3.0 mL) was added, immediately followed by additional N,N-diisopropylethylamine (1.4 mL, 8.04 mmol). The reaction was removed from the ice bath and stirred at RT for 4 hours. The volatiles were removed under reduced pressure and the residue was dissolved in EtOAc (150 mL). The solution was extracted with 20 mM aq. $KHSO_4$, water and sat. aq. $NaHCO_3$. The organic layer was dried over $MgSO_4$, filtered and the volatiles were evaporated under reduced pressure. The crude product was purified by flash chromatography on silica gel to give AOL LN4 as a colorless oil (2.16 g, 82%). LC-MS (ES): (negative ion) m/z 461 (M–$H^+$), 497 (M–$Cl^-$).

Synthesis of AOL Linker Moiety

To a solution of AOL LN4 (350 mg, 0.76 mmol) in $CH_3CN$ (13 mL) was added TEMPO (48 mg, 0.31 mmol), followed by a solution of $NaH_2PO_4.2H_2O$ (762 mg, 4.88 mmol) and $NaClO_2$ (275 mg, 3.04 mmol) in water (6.5 mL). NaClO aq. (14% available chlorine, 0.83 mL, 1.94 mmol) was added and the solution turned immediately dark brown. The reaction was stirred at RT for 6 hours, and then quenched with 100 mM $Na_2S_2O_3$ aq. until the mixture turned colorless. Acetonitrile was removed under reduced pressure and the residue was diluted with water and basified with triethylamine. The aqueous phase was extracted with EtOAc (10 mL) and then concentrated under reduced pressure. The crude product was purified by reverse phase flash chromatography on C18 to give AOL as a colorless oil (triethylammonium salt, 310 mg, 71%). LC-MS (ES): (negative ion) m/z 475 (M–$H^+$); (positive ion) m/z 499 (M+$Na^+$), 578 (M+$Et_3NH^+$).

Synthesis of AOL-$NH_2$ Linker Moiety

To a solution of AOL (446 mg, 0.94 mmol) in methanol (10 mL) was added $NH_3$ aq. (35%, 40 mL) and the mixture was stirred for 5.5 hours at RT. After this time, all the volatiles were removed under reduced pressure and the crude product was purified by reverse phase flash chromatography on C18 to give AOL $NH_2$ as a white solid (quantitative). $^1$H NMR (400 MHz, DMSO-$d_6$): δ (ppm) 8.86 (t, J=5.5 Hz, 1H, CONH), 8.28 (s, 3H, $NH_3^+$), 7.85 (s, 1H, Ar—H), 7.41 (d, J=7.6 Hz, 1H, Ar—H), 7.31 (t, J=7.9 Hz, 1H, Ar—H), 7.03 (ddd, J=8.1, 2.5, 1.1 Hz, 1H, Ar—H), 5.87 (ddt, J=17.2, 10.5, 5.3 Hz, 1H, OCH$_2$CHCH$_2$), 5.24 (dq, J=17.2, 1.7 Hz, 1H, OCH$_2$CHCH$_2$, H$_a$), 5.09 (dq, J=10.5, 1.5 Hz, 1H, OCH$_2$CHCH$_2$, H$_b$), 5.02 (dd, J=6.7, 2.4 Hz, 1H, OCHO), 4.41 (dd, J=12.2, 2.5 Hz, 1H, OCH$_2$, H$_a$), 4.18-3.99 (m, 3H, OCH$_2$CHCH$_2$ and OCH$_2$, H$_b$), 3.94-3.81 (m, 2H, OCH$_2$COOH), 3.49-3.39 (m, 1H, CH$_2$, H$_a$), 3.21-3.10 (m, 1H, CH$_2$, H$_b$), 2.86-2.70 (m, 2H, CH$_2$), 1.81-1.39 (m, 6H, CH$_2$). $^{13}$C NMR (101 MHz, DMSO-$d_6$): δ (ppm) 172.9, 166.1, 158.0, 136.2, 135.2, 129.3, 120.4, 119.3, 116.0, 111.3, 99.0, 68.8, 67.7, 66.8, 38.7, 38.4, 27.8, 26.3, 23.0. LC-MS (ESI): (negative ion) 379 (M–H); (positive ion) m/z 381 (M+$H^+$).

General Procedure for Dye-AOL Linker Coupling:

The dye carboxylate (0.15 mmol) was dissolved in 6 mL of anhydrous N,N'-dimethylformamide (DMF). N,N-diisopropylethylamine (136 µL, 0.78 mmol) was added, followed by N,N,N',N'-tetramethyl-O—(N-succinimidyl)uronium tetrafluoroborate as 0.5 M solution in anhydrous DMF (TSTU, 300 µL, 0.15 mmol). The reaction was stirred under nitrogen at RT for 1 hour. A solution of AOL $NH_2$ (0.10 mmol) in water (400 µL) was added to the activated dye solution and the reaction was stirred at RT for 3 hours. The crude product was purified by preparative scale RP-HPLC.

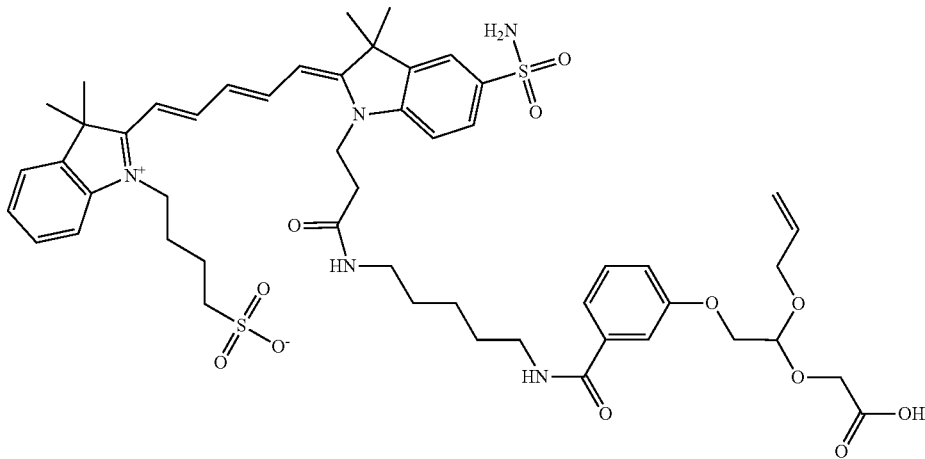

AOL-SO7181

Characterization of AOL-SO7181: 54% yield (54 mol). LC-MS (ES): (negative ion) m/z 1002 (M–$H^+$); (positive ion) m/z 1004 (M+$H^+$).

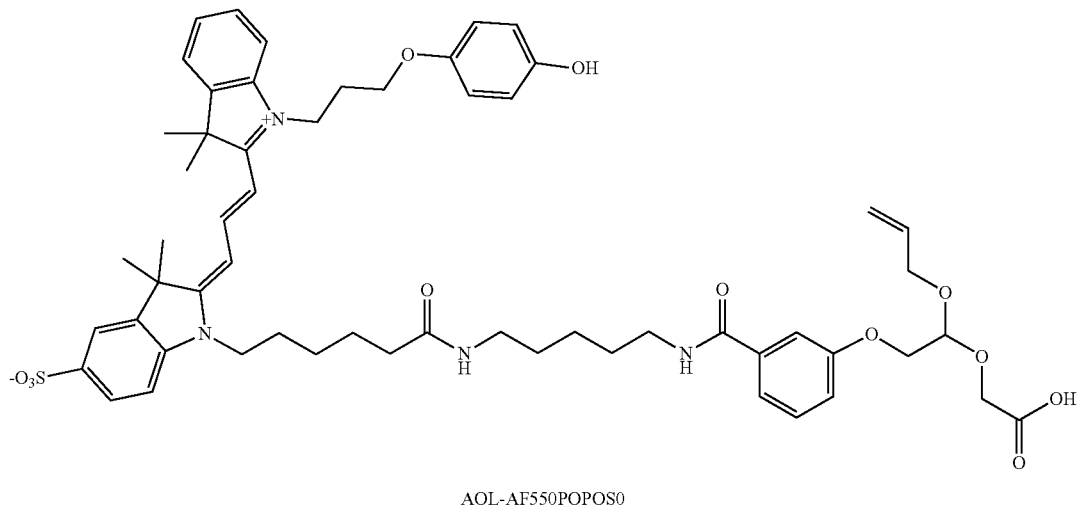
AOL-AF550POPOS0
Characterization of AOL-AF550POPOS0: 88% yield (88 mol). LC-MS (ES): (negative ion) m/z 1034 (M−H$^+$), 516 (M−2H$^+$); (positive ion) m/z 1036 (M+H$^+$), 1137 (M+Et$_3$NH$^+$).
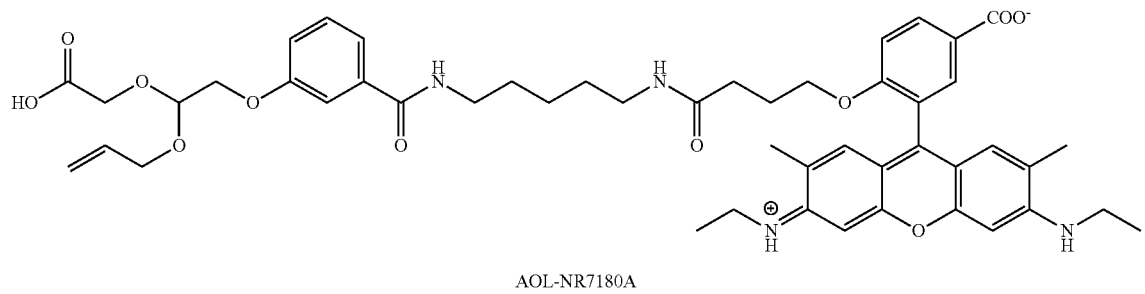
AOL-NR7180A
Characterization of AOL-NR7180A: 24% Yield (23.9 μmol). LC-MS (ES): (positive ion) m/z=880 (M+H)$^+$.
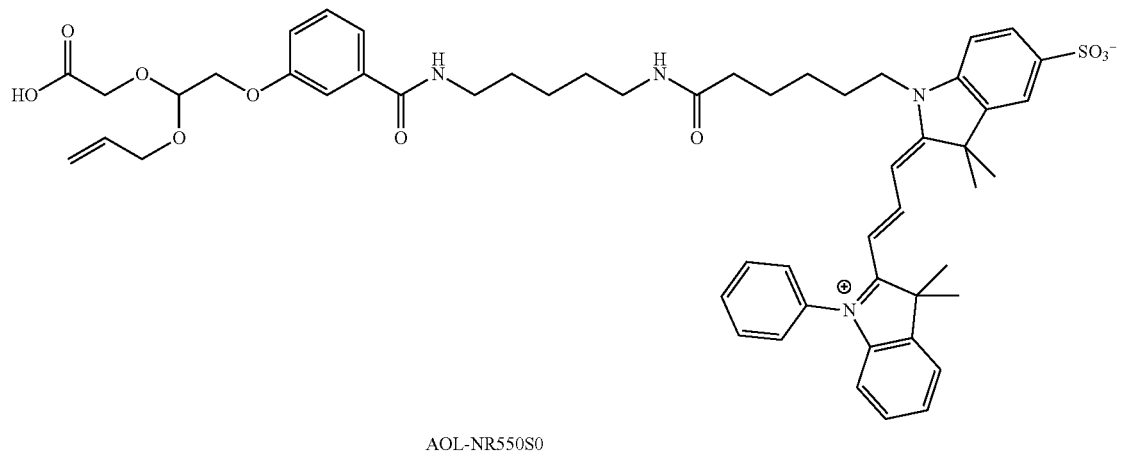
AOL-NR550S0
Characterization of AOL-NR550S0: 22% Yield (21.9 μmol). LC-MS (ES): (positive ion) m/z=963 (M+H)$^+$. (negative ion) m/z=961 (M−H$^+$).

Scheme 2. Synthesis of a 5'-triphosphate-3'-AOM-A(DB) nucleotide

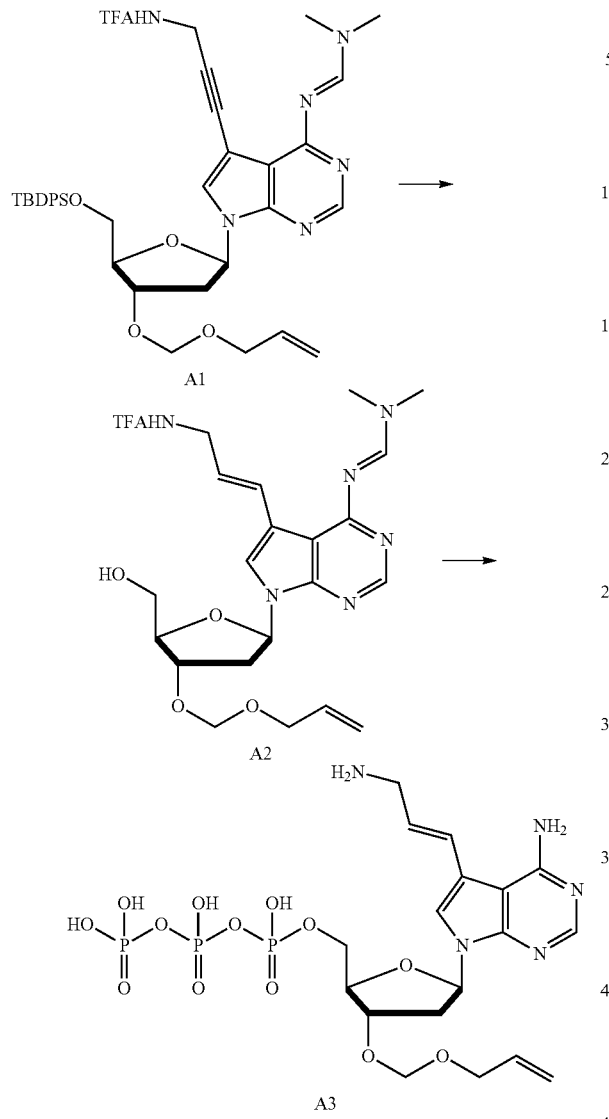

Synthesis of Intermediate A2:

Compound A1 (319 mg, 0.419 mmol) was dissolved in 0.8 mL of anhydrous DCM under $N_2$ atmosphere, then pentamethylcyclopentadienyltris (acetonitrile)ruthenium(II) hexafluorophosphate ([RuCp*(MeCN)$_3$]PF$_6$, 42 mg, 0.08 mmol) was added, followed by triethoxysilane (231 μL, 1.25 mmol). The reaction was stirred at RT under $N_2$ for 1 hour. Then the solution was diluted with DCM and filtered on a plug of silica gel, which was washed with ethyl acetate. The solution was evaporated under reduced pressure, left to dry under vacuum for 10 minutes, then the residue was dissolved in 2 mL of anhydrous THF. Copper iodide (15 mg, 0.08 mmol) and a 1 M solution of TBAF in THF (920 μL, 0.919 mmol) were added. The reaction was stirred for 2.5 hours at RT then, diluted with EtOAc and extracted with sat. NH$_4$Cl. The aqueous phase was extracted with EtOAc. The pooled organic phases were dried over MgSO$_4$, filtered and evaporated to dryness. The residue was purified by flash chromatography on silica. Yield: 125 mg (0.237 mmol). LC-MS (ES and CI): (positive ion) m/z 527 (M+H$^+$).

Synthesis of Intermediate A3:

Nucleoside A2 (155 mg, 0.294 mmol) was dried under reduced pressure over P$_2$O$_5$ for 18 hrs. Anhydrous triethyl phosphate (1 mL) and some freshly activated 4 Å molecular sieves were added to it under nitrogen, then the reaction flask was cooled to 0° C. in an ice-bath. Freshly distilled POCl$_3$ (33 μL, 0.353 mmol) was added dropwise followed by Proton Sponge® (113 mg, 0.53 mmol). After the addition, the reaction was further stirred at 0° C. for 15 minutes. Then, a 0.5 M solution of pyrophosphate as bis-tri-n-butylammonium salt (2.94 mL, 1.47 mmol) in anhydrous DMF was quickly added, followed immediately by tri-n-butyl amine (294 μL, 1.32 mmol). The reaction was kept in the ice-water bath for another 10 minutes, then quenched by pouring it into 1 M aqueous triethylammonium bicarbonate (TEAB, 10 mL) and stirred at RT for 4 hours. All the solvents were evaporated under reduced pressure. A 35% aqueous solution of ammonia (10 mL) was added to the above residue and the mixture was stirred at RT for at least 5 hours. The solvents were then evaporated under reduced pressure. The crude product was purified firstly by ion-exchange chromatography on DEAE-Sephadex A25 (50 g). The column was eluted with aqueous triethylammonium bicarbonate (TEAB). The fractions containing the triphosphate were pooled and the solvent was evaporated to dryness under reduced pressure. The crude material was further purified by preparative scale HPLC. Compound A3 was obtained as triethylammonium salt. Yield: 134 μmol (46%). LC-MS (ESI): (negative ion) m/z 614 (M−H$^+$).

Furthermore, 5'-triphosphate-3'-AOM-A nucleotide of structure

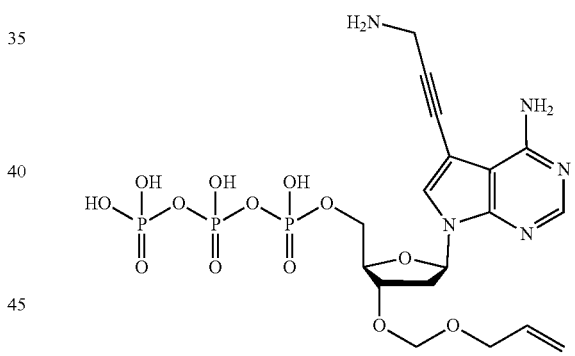

and the corresponding ffA were also prepared. The detailed synthesis is described in U.S. application Ser. No. 16/724,088.

General Synthesis of Nucleotide Triphosphate-AOL Linker:

The compound AOL (0.120 mmol) was coevaporated with 2×2 mL of anhydrous N,N'-dimethylformamide (DMF), then dissolved in 3 mL of anhydrous N,N'-dimethylacetamide (DMA). N,N-diisopropylethylamine (70 μL, 0.4 mmol) was added, followed by N,N,N',N'-tetramethyl-O—(N-succinimidyl)uronium tetrafluoroborate (TSTU, 36 mg, 0.120 mmol). The reaction was stirred under nitrogen at RT for 1 hour. In the meantime, an aqueous solution of the nucleotide triphosphate (0.08 mmol) was evaporated to dryness under reduced pressure and resuspended in 300 μL of 0.1 M triethylammonium bicarbonate (TEAB) solution in water. The activated linker solution was added to the triphosphate and the reaction was stirred at RT for 18 hours and monitored by RP-HPLC. The solution was concentrated then 10 mL of concentrated aqueous NH$_4$OH were added.

The reaction was stirred at RT for 24 hours, then it was evaporated under reduced pressure. The crude product was purified firstly by ion-exchange chromatography on DEAE-Sephadex A25 (50 g) eluting with aqueous triethylammonium bicarbonate (TEAB). The fractions containing the triphosphate were pooled and the solvent was evaporated to dryness under reduced pressure. The crude material was further purified by preparative scale HPLC.

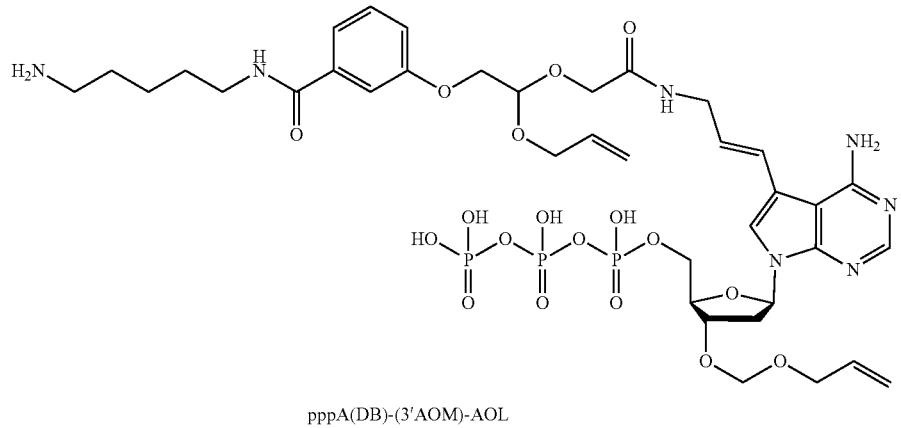

pppA(DB)-(3'AOM)-AOL

Characterization of pppA(DB)-(3'AOM)-AOL: Yield: 60 µmol, (75%). LC-MS (ES): (negative ion) m/z 976 (M−H$^+$), 488 (M−2H$^+$).

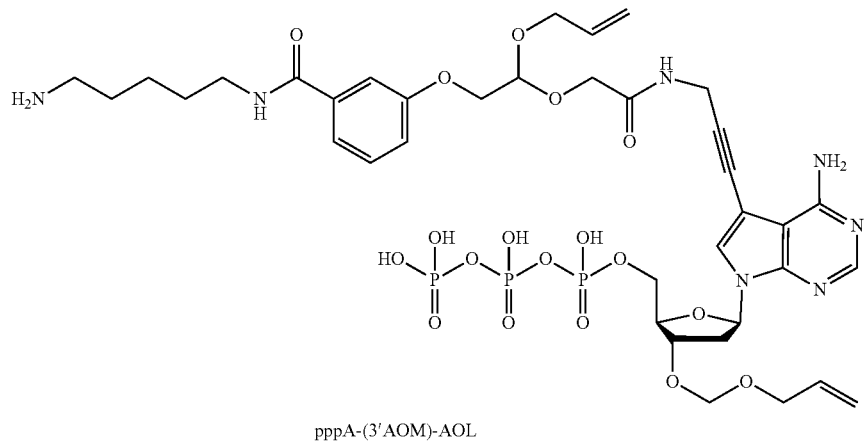

pppA-(3'AOM)-AOL

Characterization of pppA(DB)-(3'AOM)-AOL: Yield: 68 µmol, (72%). $^1$H NMR (400 MHz, D$_2$O): δ (ppm) 7.94 (d, J=1.7 Hz, 1H, H-2), 7.32 (d, J=1.6 Hz, 1H, H-8), 7.10-6.96 (m, 2H, Ar), 6.95-6.87 (m, 2H, Ar), 6.41-6.31 (m, 1H, 1'-CH), 6.01-5.81 (m, 2H, CH allyl), 5.29 (ddq, J=17.2, 6.1, 1.4 Hz, 2H, CHH allyl), 5.20 (ddt, J=10.5, 3.8, 1.1 Hz, 2H, CHH allyl), 5.02 (td, J=4.4, 2.4 Hz, 1H, O—CH$_2$—O linker), 4.92-4.81 (m, 2H, 3'-O—CH$_2$—O), 4.53 (dd, J=4.9, 2.4 Hz, 1H, 3'-CH), 4.39 (dd, J=16.1, 4.0 Hz, 1H, O—CHH linker), 4.32-4.19 (m, 2H, O—CHH linker, 4'-CH), 4.17-4.01 (m, 8H, 5'-CH$_2$, CH$_2$O linker, CH$_2$—O allyl), 3.25-3.11 (m, 2H, CH$_2$—NHCO), 3.04 (q, J=7.3 Hz, 18H, Et$_3$N), 2.92-2.82 (m, 2H, CH$_2$—N linker), 2.55-2.41 (m, 2H, 2'-CH$_2$), 1.59 (p, J=7.6 Hz, 2H, CH$_2$—CH$_2$—N linker), 1.47 (p, J=7.1 Hz, 2H, CH$_2$—CH$_2$—NHCO), 1.31 (tt, J=8.3, 4.4 Hz, 2H, CH$_2$—CH$_2$—CH$_2$—N linker), 1.15 (t, J=7.3 Hz, 26H). $^{31}$P NMR (162 MHz, D$_2$O): δ (ppm) −6.18 (d, J=20.6 Hz, $^\gamma$P), −11.32 (d, J=19.3 Hz, $^\alpha$P), −22.20 (t, J=19.9 Hz, $^\beta$P).

Scheme 3. Synthesis of a 5'-triphosphate-3'-AOM-A(DB) nucleotide

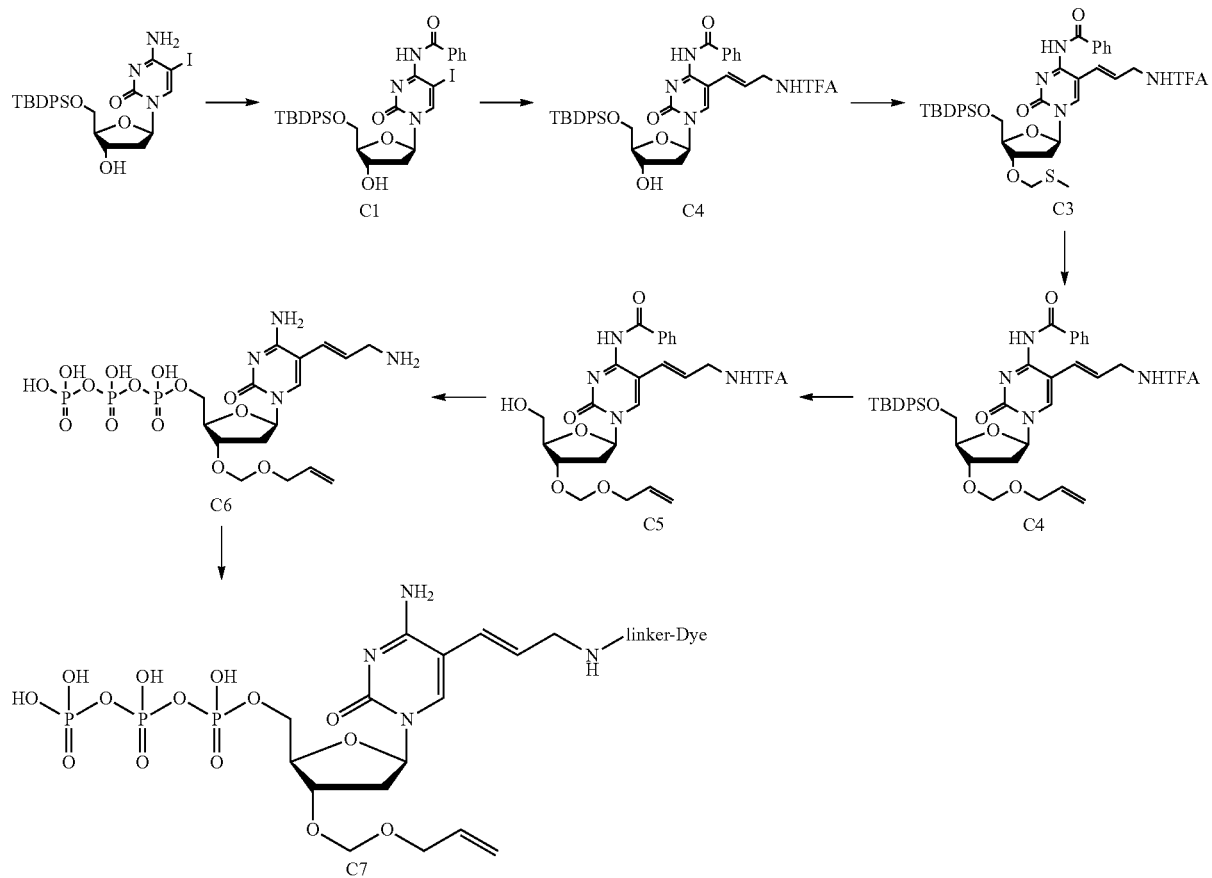

Synthesis of Intermediate C1

5-iodo-5'-O-(tert-butyldiphenylsilyl)-2'-deoxycytidine (3 g, 5.07 mmol) was dissolved in 30 mL of anhydrous pyridine, then chlorotrimethylsilane (1.29 mL, 10.1 mmol) was added dropwise. The reaction was stirred at RT for 1 hour, then placed in an ice bath and benzoyl chloride (648 µL, 5.6 mmol) was added slowly dropwise. The reaction was removed from the ice bath, then stirred 1 hour at RT. Upon completion, the solution was placed in an ice bath and quenched with 50 mL of cold water, then 50 mL of methanol and 20 mL of pyridine were added, and the suspension was stirred at RT overnight. The solvents were evaporated under reduced pressure and the residue was dissolved in 200 mL of EtOAc and extracted with 2×200 mL of sat. NaHCO$_3$ and 100 mL of brine. The organic phase was dried over MgSO$_4$, filtered and evaporated to dryness. The crude was purified by flash chromatography on silica gel to afford C1. Yield: 2.535 g (3.64 mmol, 73%). LC-MS (ESI): (positive ion) m/z 696 (M+H$^+$), 797 (M+Et$_3$NH$^+$).

Synthesis of Intermediate C2

N-Benzoyl-5-iodo-5'-O-(tert-butyldiphenylsilyl)-2'-deoxycytidine (C1) (695 mg, 1 mmol) and palladium(II) acetate (190 mg, 0.85 mmol) were dissolved in dry degassed DMF (10 mL), then N-allyltrifluoroacetamide (7.65 mL, 5 mmol) was added. The solution was placed under vacuum and purged with nitrogen for 3 times, then degassed triethylamine (278 µL, 2 mmol) was added. The solution was heated to approximately 80° C., protected from light for 1 hour. The resulting black mixture was cooled down to RT then diluted with 50 mL of EtOAc, then extracted with 100 mL of water. The aqueous phase was then extracted with EtOAc. The organic phases were pooled, dried over MgSO$_4$, filtered and evaporated to dryness. The crude was purified by flash chromatography on silica gel to afford C2. Yield: 305 mg (0.42 mmol, 42%). LC-MS (ES and CI): (positive ion) m/z 721 (M+H$^+$), 797 (M+Et$_3$NH$^+$).

Synthesis of Intermediate C3

N-Benzoyl-5-[3-(2,2,2-trifluoroacetamido)-allyl]-5'-O-(tert-butyldiphenylsilyl)2'-deoxycytidine (C2) (350 mg, 0.486 mmol) was dissolved in 1.1 mL of anhydrous DMSO (14.5 mmol), then glacial acetic acid (1.7 mL, 29.1 mmol) and acetic anhydride (1.7 mL, 17 mmol) were added. The reaction was heated to 60° C. for 6 hours then quenched with 50 mL of aq. saturated NaHCO$_3$. After the solution stopped bubbling, it was extracted with EtOAc. The organic phases were pooled and washed with aq. saturated NaHCO$_3$, water and brine. The organic phase was dried over MgSO$_4$, filtered and evaporated to dryness. The crude was purified by flash chromatography on silica gel to afford C3. Yield: 226 mg (0.289 mmol, 60%). LC-MS (ESI): (positive ion) m/z 781 (M+H$^+$), 882 (M+Et$_3$NH$^+$).

Synthesis of Intermediate C4

N-Benzoyl-5-[3-(2,2,2-trifluoroacetamido)-allyl]-5'-O-(tert-butyldiphenylsilyl)-3'-O-methylthiomethyl-2'-deoxycytidine (C3) (210 mg, 0.27 mmol) was dissolved in 5 mL of anhydrous DCM under N$_2$ atmosphere, cyclohexene (136 µL, 1.35 mmol) was added and the solution was cooled to approximately −10° C. A 1 M solution of freshly distilled sulfuryl chloride in anhydrous DCM (320 μL, 0.32 mmol) was added dropwise and the reaction was stirred for 20 minutes. After all the starting material had been consumed, an extra portion of cyclohexene was added (136 μL, 1.35 mmol) and the reaction was evaporated to dryness under reduced pressure. The residue was quickly purged with nitrogen, then the residue was dissolved in 2.5 mL of ice-cold anhydrous DCM and ice-cold allyl alcohol (2.5 mL) was added under stirring at 0° C. The reaction was stirred at 0° C. for 3 hours, then quenched with saturated aq. $NaHCO_3$, then diluted further with saturated aq. $NaHCO_3$. The mixture was extracted with EtOAc. The pooled organic phases were dried over $MgSO_4$, filtered and evaporated to dryness. The residue was purified by flash chromatography on silica gel to afford C4. Yield: 58% (124 mg, 0.157 mmol). LC-MS (ESI): (positive ion) m/z 791 (M+H$^+$).

Synthesis of Intermediate C5

N-Benzoyl-5-[3-(2,2,2-trifluoro acetamido)-allyl]-5'-O-(tert-butyldiphenylsilyl)-3'-O-allyloxymethyl-2'-deoxycytidine (C4) (120 mg, 0.162 mmol) was dissolved in dry THF (5 mL) under $N_2$ atmosphere, then placed at 0° C. Glacial acetic acid (29 μL, 0.486 mmol) was added, immediately followed by a solution of 1.0 M TBAF in THF (486 μL, 0.486 mmol). The solution was stirred at 0° C. for 3 hours. The solution was diluted with EtOAc, then extracted with 0.025N HCl and with brine. The organic phase was dried over $MgSO_4$, filtered and evaporated to dryness. The residue was purified by flash chromatography on silica gel to afford C5. Yield: 50 mg (0.090 mmol, 55%). LC-MS (ESI): (positive ion) m/z 553 (M+H$^+$); (negative ion) m/z 551 (M−H$^+$), 587 (M+Cl$^-$).

Synthesis of Intermediate C6

N-Benzoyl-3'-O-allyloxymethyl-5-[3-(2,2,2-trifluoroacetamido)-allyl]-2'-deoxycytidine (C5) (50 mg, 0.0.09 mmol) was dried under reduced pressure over $P_2O_5$ for 18 hrs. Anhydrous triethyl phosphate (1 mL) and some freshly activated 4 Å molecular sieves were added to it under nitrogen, then the reaction flask was cooled to 0° C. in an ice-bath. Freshly distilled $POCl_3$ (10 μL, 0.108 mmol) was added dropwise followed by Proton Sponge® (29 mg, 0.135 mmol). After the addition, the reaction was further stirred at 0° C. for 15 minutes. Then, a 0.5 M solution of pyrophosphate as bis-tri-n-butylammonium salt (1 mL, 0.45 mmol) in anhydrous DMF was quickly added, followed immediately by tri-n-butyl amine (100 μL, 0.4 mmol). The reaction was kept in the ice-water bath for another 10 minutes, then quenched by pouring it into 1 M aqueous triethylammonium bicarbonate (TEAB, 5 mL) and stirred at RT for 4 hours. All the solvents were evaporated under reduced pressure. A 35% aqueous solution of ammonia (5 mL) was added to the above residue and the mixture was stirred at RT for 18 hours. The solvents were then evaporated under reduced pressure, the residue resuspended in 10 mL of 0.1 M TEAB and filtered. The filtrate was purified firstly by ion-exchange chromatography on DEAE-Sephadex A25 (50 g). The column was eluted with aqueous triethylammonium bicarbonate. The fractions containing the triphosphate were pooled and the solvent was evaporated to dryness under reduced pressure. The crude material was further purified by preparative scale HPLC. Compound $C_6$ was obtained as triethylammonium salt. Yield: 40.6 μmol (45%), based on $ε_{290}$=5041 $M^{-1}$ $cm^{-1}$. $^1$H NMR (400 MHz, $D_2O$): δ (ppm) 8.23 (s, 1H, H-6), 6.53 (dd, J=15.5, 0.9 Hz, 1H, Ar—CH=), 6.42-6.24 (m, 2H, Ar—CH=CH—, 1'-CH), 5.98 (ddt, J=17.3, 10.4, 5.9 Hz, 1H, O—$CH_2$—CH=), 5.37 (dq, J=17.3, 1.6 Hz, 1H, CHH=), 5.29 (ddt, J=10.4, 1.6, 1.1 Hz, 1H, CHH=), 4.89 (s, 2H, O—$CH_2$—O), 4.60 (dt, J=6.2, 3.1 Hz, 1H, 3'-CH), 4.39 (t, J=2.7 Hz, 1H, 4'-CH), 4.35 (dq, J=12.0, 3.8 Hz, 1H, 5'-CHH), 4.28-4.21 (m, 1H, 5'-CHH), 4.20 (ddt, J=6.0, 2.7, 1.4 Hz, 1H, =CH—$CH_2$—O), 3.73 (dt, J=7.2, 1.4 Hz, 2H, $CH_2$—$NH_2$), 3.18 (q, J=7.3 Hz, 20H, $Et_3N$), 2.59 (ddd, J=14.1, 6.1, 3.3 Hz, 1H, 2'-CHH), 2.37 (ddd, J=14.2, 7.2, 6.1 Hz, 1H, 2'-CHH), 1.27 (t, J=7.3 Hz, 31H, $Et_3N$). $^{31}$P NMR (162 MHz, $D_2O$): δ (ppm) −6.06 (d, J=20.7 Hz, $^γ$P), −11.24 (d, J=19.1 Hz, $^α$P), −21.95 (t, J=19.7 Hz, $^β$P). LC-MS (ESI): (negative ion) m/z 591 (M−H$^+$).

Furthermore, 5'-triphosphate-3'-AOM-C nucleotide, the 5'-triphosphate-3'-AOM-T (DB) nucleotide of the structure:

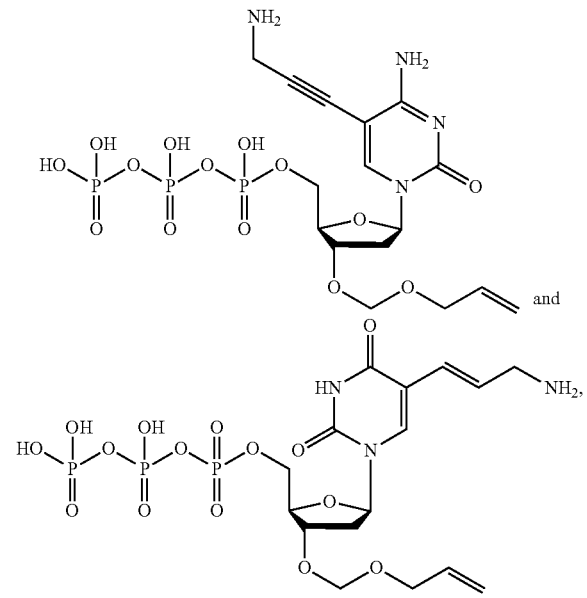

and the corresponding ffC and ffT (DB) were also prepared. Finally, 5'-triphosphate-3'-AOM-G (also referred to as ffG-(3'-AOM))

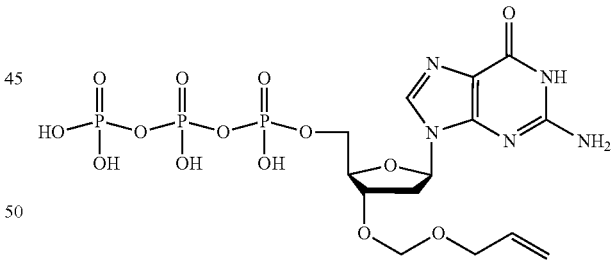

was also prepared. The detailed syntheses are described in U.S. Publication No. 2020/0216891.

General Synthesis of Fully Functionalized Nucleotides with AOL Linker Moiety

The Dye-COOH (0.02 mmol) or Dye-AOL (0.02 mmol) was coevaporated with 2×2 mL of anhydrous N,N'-dimethylformamide (DMF), then dissolved in 2 mL of anhydrous N,N'-dimethylacetamide (DMA). N,N-diisopropylethylamine (17 μL, 0.1 mmol) was added, followed by N,N,N',N'-tetramethyl-O—(N-succinimidyl)uronium tetrafluoroborate (TSTU, 6 mg, 0.02 mmol). The reaction was stirred under nitrogen at RT for 1 hour. In the meantime, an aqueous solution of the nucleotide triphosphate (0.01 mmol) was evaporated to dryness under reduced pressure and resuspended in 200 μL of 0.1 M triethylammonium bicarbonate (TEAB) solution in water. The activated Dye solution was added to the nucleotide triphosphate and the reaction was stirred at RT for 18 hours and monitored by RP-HPLC. The crude product was purified firstly by ion-exchange chromatography on DEAE-Sephadex A25 (25 g) eluting with a linear gradient of aqueous triethylammonium bicarbonate (TEAB, from 0.1 M to 1 M). The fractions containing the triphosphate were pooled and the solvent was evaporated to dryness under reduced pressure. The crude material was further purified by preparative scale HPLC.

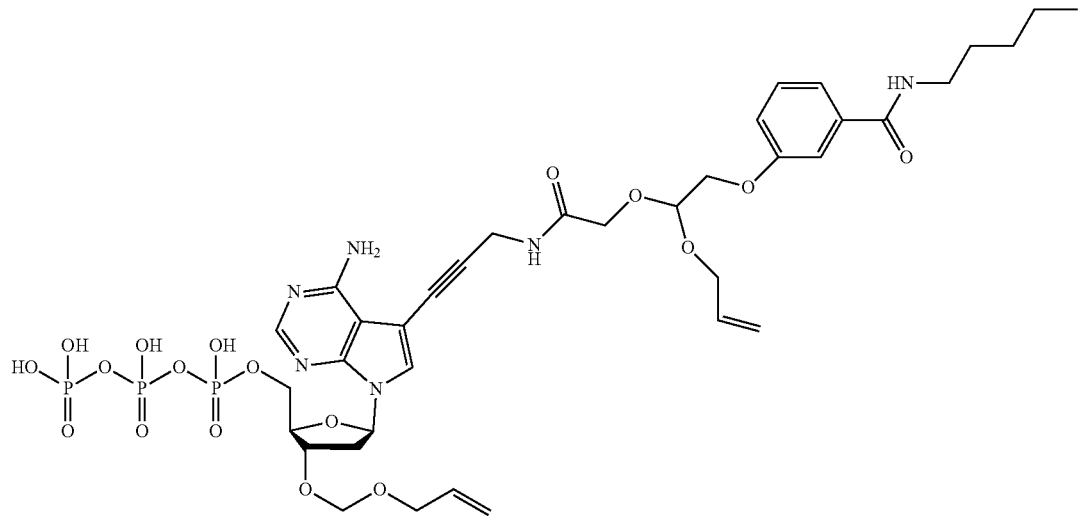

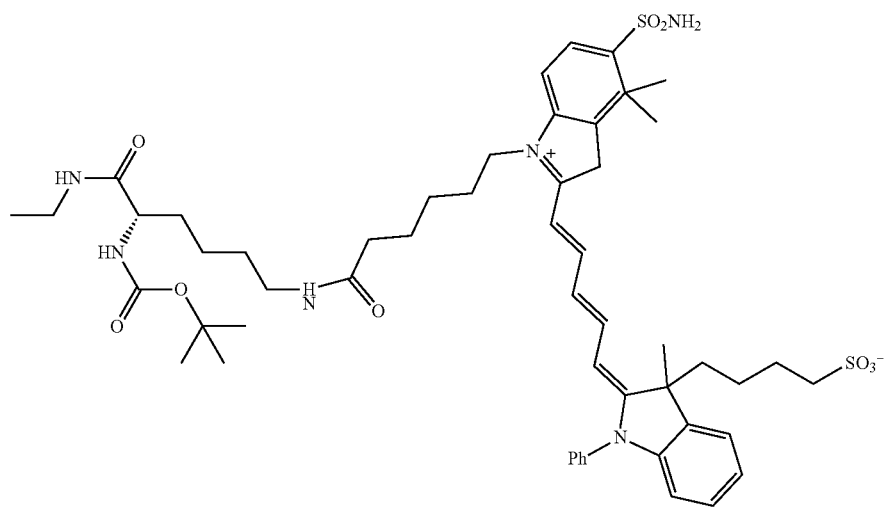

ffA-(3'AOM)-AOL-BL-NR650C5

60

Characterization of ffA-(3'AOM)-AOL-BL-NR650C5: 66% yield, (6.6 μmol). LC-MS (ES): (negative ion) m/z 1931 (M−H⁺), 965 (M−2H⁺).

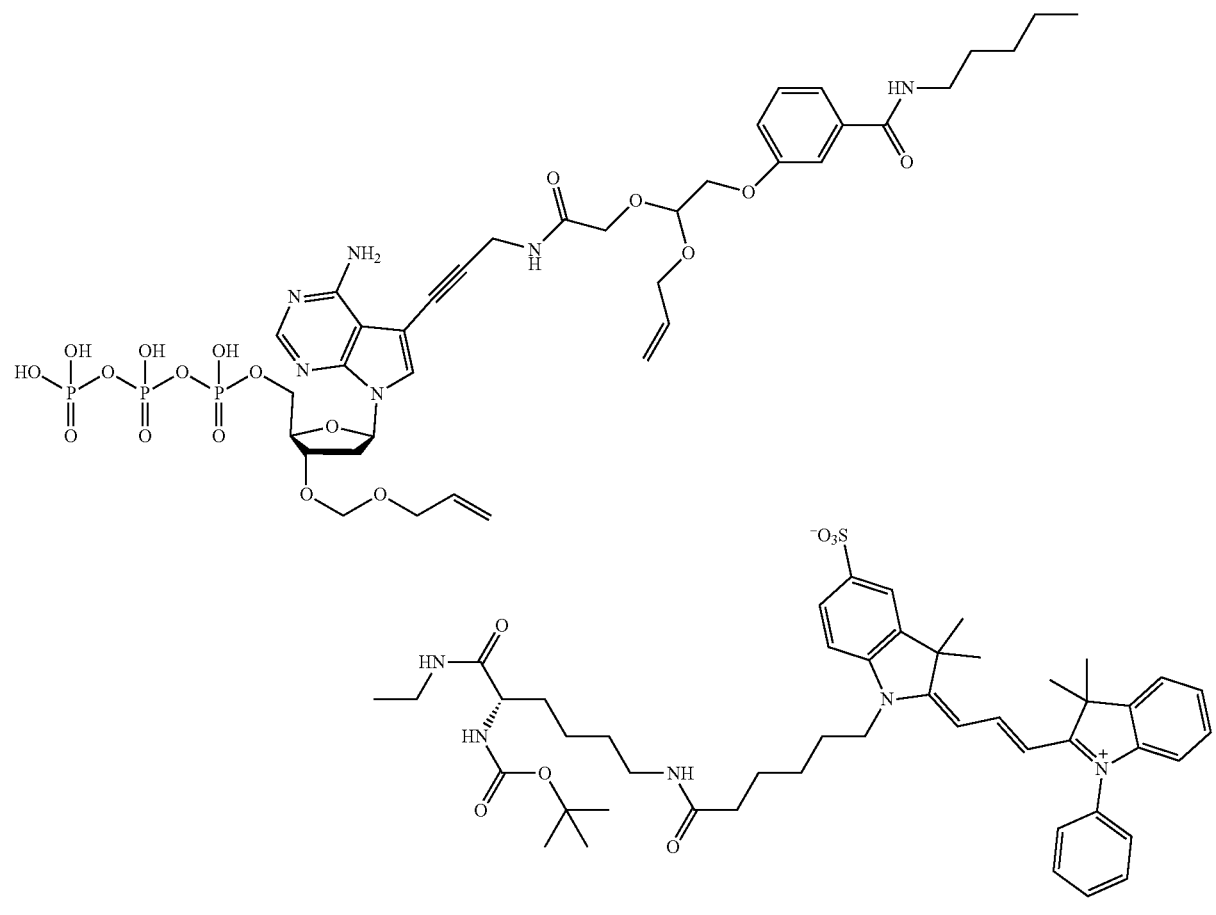
ffA-(3'AOM)-AOL-BL-NR550s0
Characterization of ffA-(3'AOM)-AOL-BL-NR550s0: 65% yield (6.5 μmol). LC-MS (ES): (negative ion) m/z 1784 (M−H⁺), 891 (M−2H⁺).
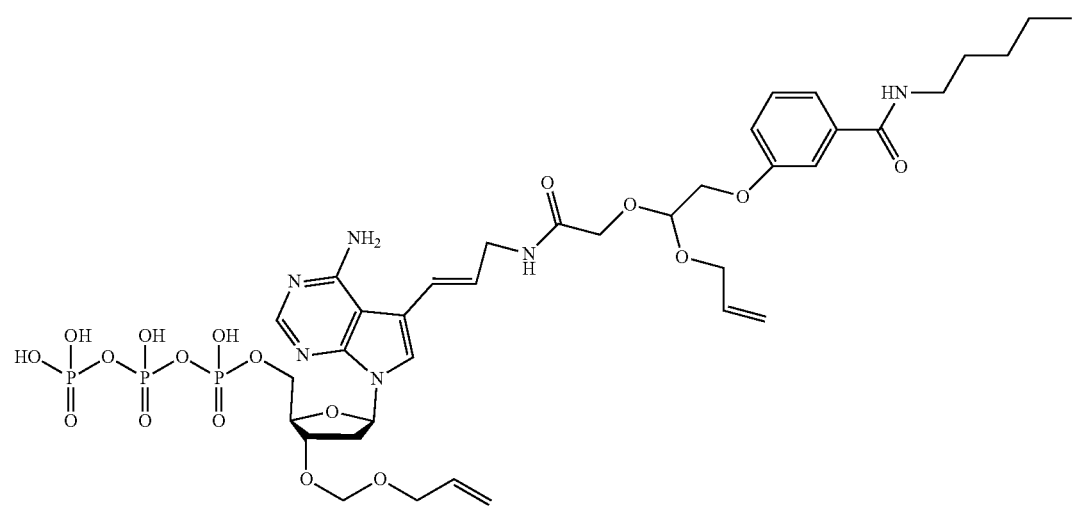

-continued
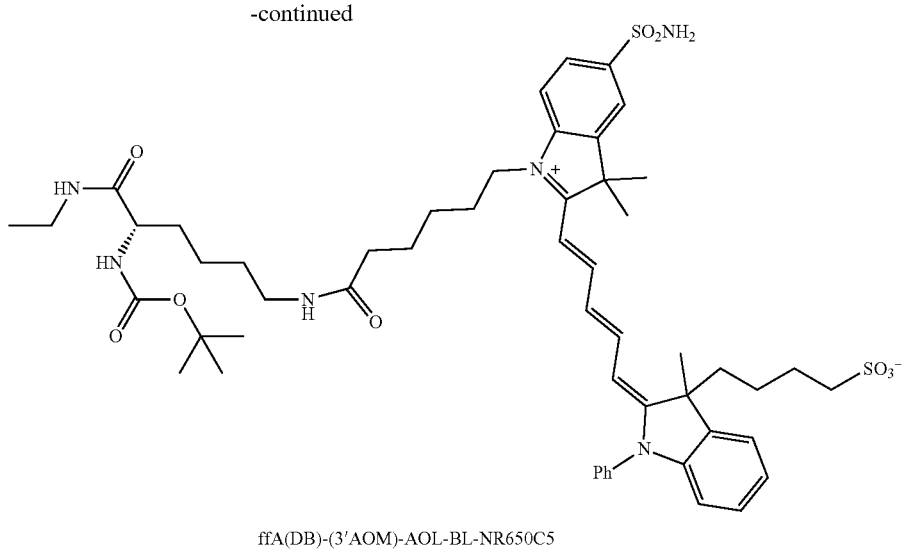
ffA(DB)-(3'AOM)-AOL-BL-NR650C5
Characterization of ffA(DB)-(3'AOM)-AOL-BL-NR650C5: 31% yield (3.1 mol). LC-MS (ES): (negative ion) m/z 1933 (M−H$^+$), 965 (M−2H$^+$), 644 (M−3H$^+$).
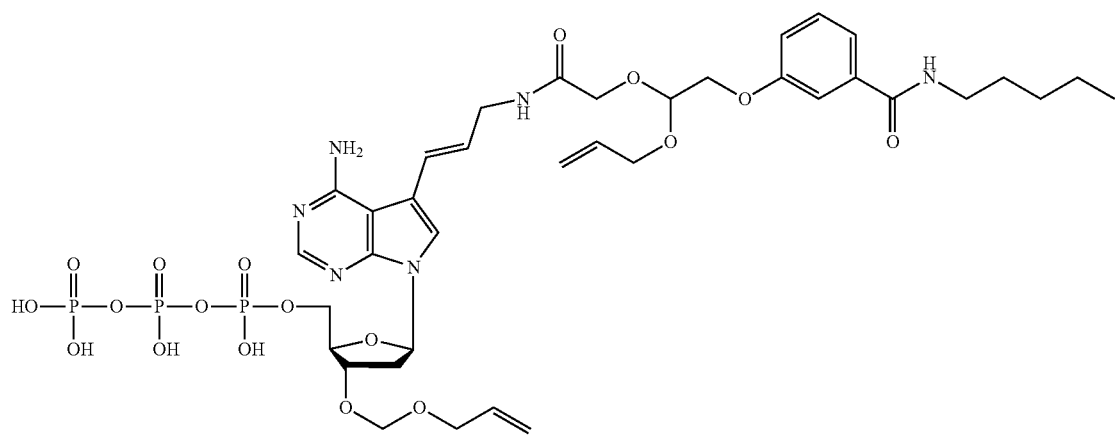
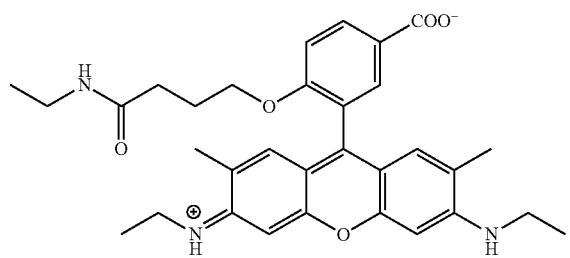
ffA(DB)-(3'AOM)-AOL-NR7180A
Characterization of ffA(DB)-(3'AOM)-AOL-NR7181A: 21% yield (2.12 mol). LC-MS (ES): (negative ion) m/z=1475 (M−H$^+$).

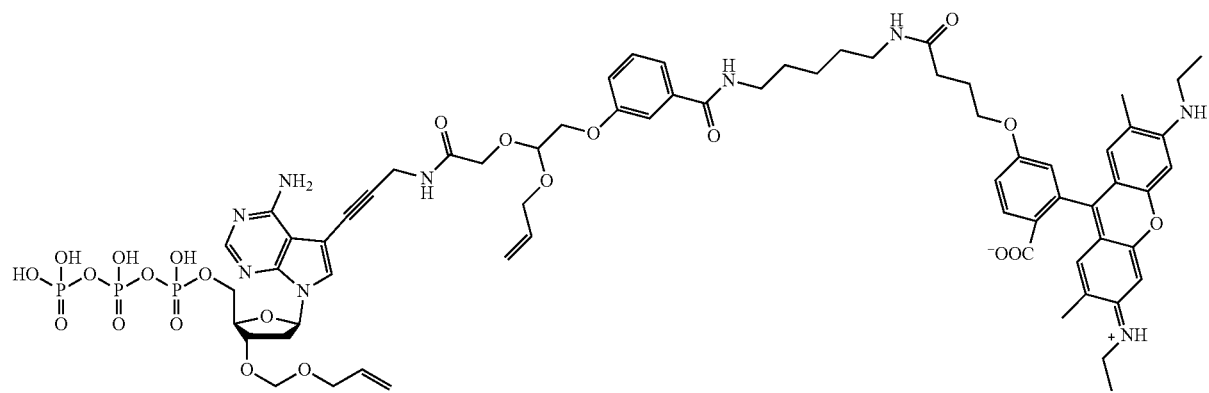
ffA-(3'AOM)-AOL-NR7180A
Characterization of ffA-(3'-AOM)-AOL-NR7180A: 41% yield (4.1 mol). LC-MS (ES): (negative ion) m/z 1472 (M−H$^+$), 736 (M−2H$^+$).
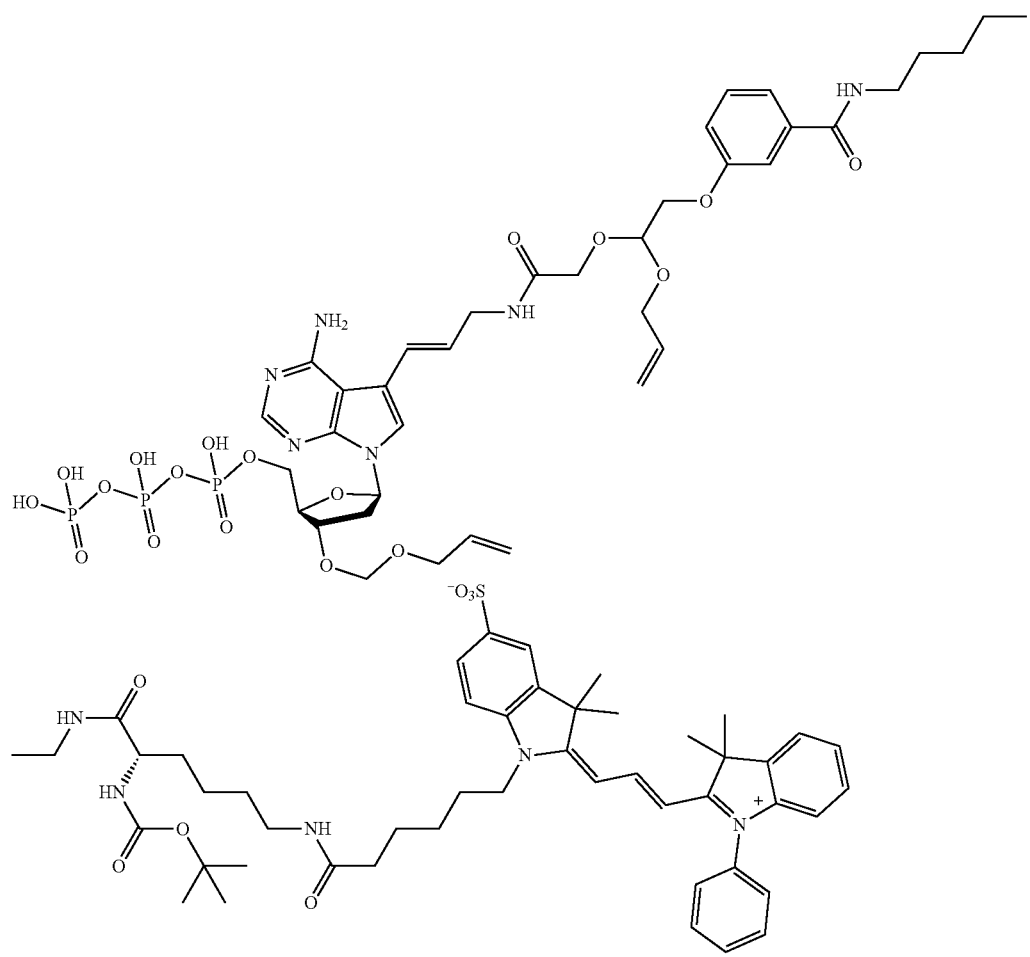
ffA(DB)-(3'AOM)-AOL-BL-NR550s0
Characterization of ffA(DB)-(3'-AOM)-AOL-BL-NR550S0: 21% yield (2.1 μmol). LC-MS (ES): (negative ion) m/z 1786 (M−H$^+$), 892 (M−2H$^+$), 594 (M−3H$^+$).

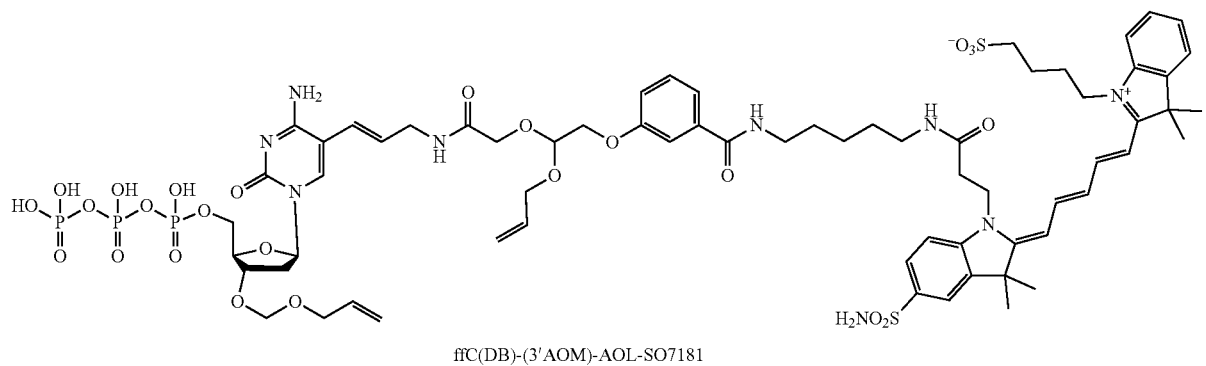
ffC(DB)-(3'AOM)-AOL-SO7181
Characterization of ffC(DB)-(3'AOM)-AOL-SO7181: 48% yield, (4.87 mol). LC-MS (ES): (negative ion) m/z 1577 (M−H$^+$), 788 (M−2H$^+$), 525 (M−3H$^+$).
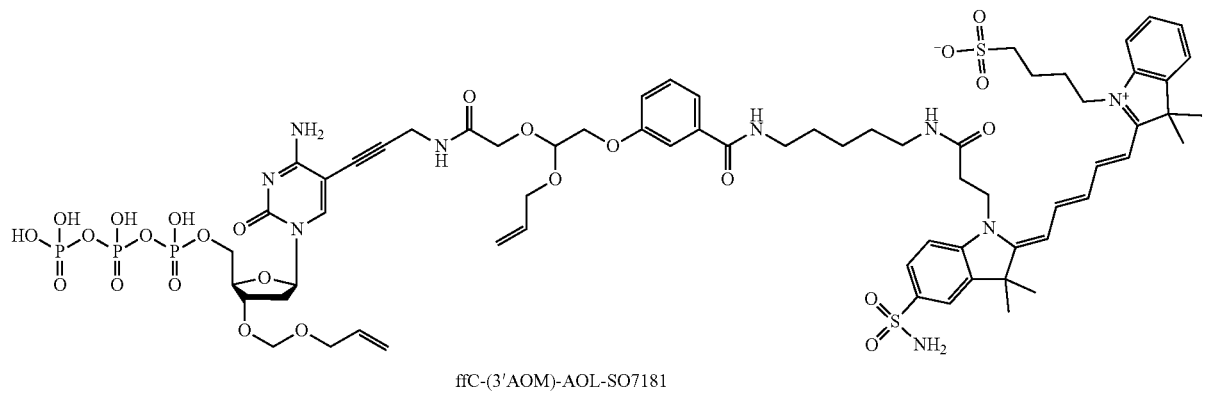
ffC-(3'AOM)-AOL-SO7181
Characterization of ffC-(3'-AOM)-AOL-S07181: 56% yield (5.6 mol). LC-MS (ES): (negative ion) m/z 1575 (M−H$^+$), 787 (M−2H$^+$).
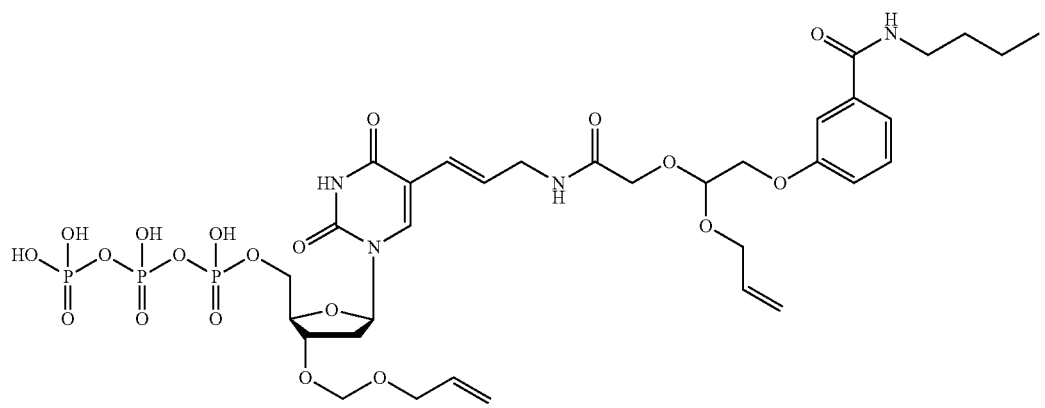

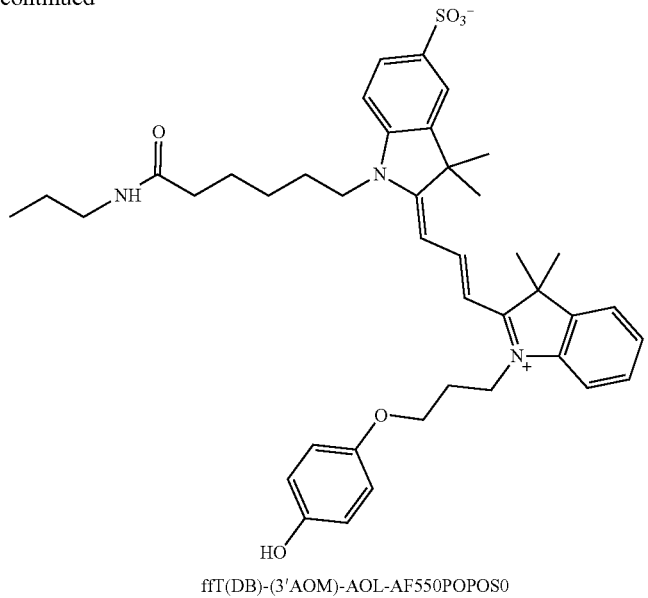

ffT(DB)-(3'AOM)-AOL-AF550POPOS0

Characterization of ffT(DB)-3'AOM-AOL-AF550POPOS0: 46% yield (4.6 mol). LC-MS (ES): (negative ion) m/z 1609 (M–H⁺), 804 (M–2H⁺), 536 (M–3H⁺).

at set time points, quenching them with a 1:1 solution of EDTA/H₂O₂ (0.1:0.1 M) and analyzing them by HPLC for the formation of 3'-OH nucleotide and the disappearance of

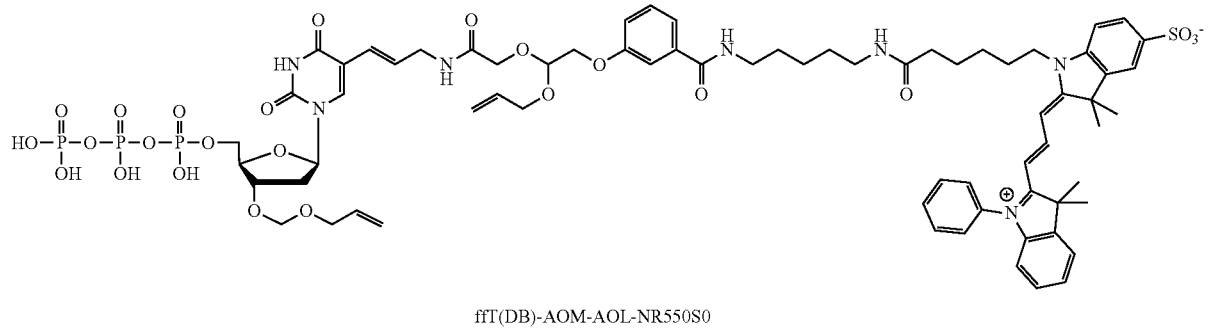

ffT(DB)-AOM-AOL-NR550S0

Characterization of ffT(DB)-(3'AOM)-AOL-NR550s0: 38% yield (3.8 µmol). LC-MS (ES): (negative ion) m/z=1535 (M–H⁺).

Example 2. Solution Cleavage Efficiency of Different Palladium Reagent Formulations FIG. 1 illustrates a comparison of the solution cleavage efficiency of three different formulations of palladium reagents: 1) 10 mM [(Allyl)PdCl]₂, 100 mM THP, 100 mM ethanolamine buffer, 10 mM sodium ascorbate 2) 20 mM Na₂PdCl₄, 60 mM THP, 100 mM N,N'-diethylethanolamine, 10 mM sodium ascorbate, 1M NaCl, 0.1% Tween 20 3) 20 mM Na₂PdCl₄, 70 mM THP, 100 mM N,N'-diethylethanolamine, 10 mM sodium ascorbate, 1M NaCl, 0.1% Tween 20. The cleavage efficiency was determined by measuring the relative rate of cleavage of a 3'-AOM-nucleotide substrate. Briefly, to a 0.1 mM solution of 3'-AOM-nucleotide substrate in 100 mM buffer was added a stock solution of a palladium reagent to a final concentration of 1 mM in Pd species. The solution was incubated at RT and the reaction kinetic was monitored by taking aliquots from the reaction at set time points, quenching them with a 1:1 solution of EDTA/H₂O₂ (0.1:0.1 M) and analyzing them by HPLC for the formation of 3'-OH nucleotide and the disappearance of the 3'-AOM nucleotide substrate. As shown in FIG. 1, the cleavage efficiency of Na₂PdCl₄ is comparable to that of [(Allyl)PdCl]₂ when only 3 or 3.5 equivalents of THP were used, as compared to 10 equivalents of THP for [(Allyl)PdCl]₂.

Figure 2:
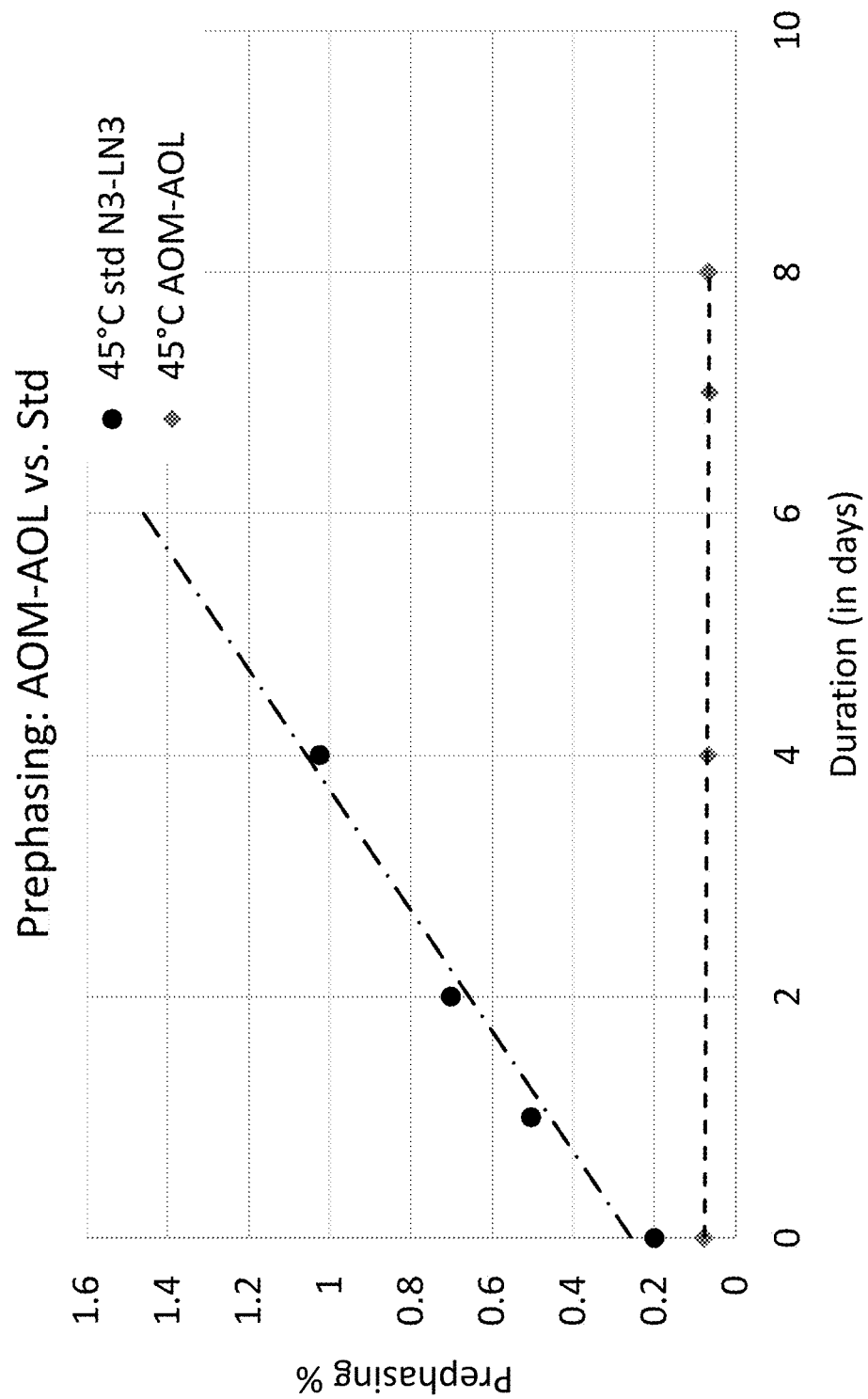
FIG. 2 is a line chart showing the percent prephasing values as a function of time of standard fully functionalized nucleotides (ffNs) with LN3 linker moiety and 3'-O-azidomethyl blocking group as compared to ffNs with AOL linker moiety and 3'-AOM blocking group.

Example 3: AOM-AOL ffN Stability Studies in Solution and Performance in Sequencing FIG. 2 illustrates the prephasing performance of fully functionalized nucleotides (ffNs) with 3'-AOM blocking group and AOL linker moiety (including labeled ffT-DB, labeled ffAs and labeled ffC, and unlabeled ffG) compared to standard MiniSeq® ffNs which have been stressed. The two sets of ffNs were incubated at 45° C. for several days in standard incorporation mix formulations only excluding the DNA polymerase. For each time point, fresh polymerase was added to complete the incorporation mix directly prior to loading on MiniSeq®. Sequencing conditions described previously were used. Prephasing % is a direct indicator of the percentage of 3' OH-ffNs present in the mix therefore directly correlates to the stability of the 3' block group.

Prephasing values for both sets of ffNs were recorded and plotted (FIG. 2). Compared to standard, AOM-AOL-ffNs did not show any increase in prephasing. and appeared to be substantially more stable than standard ffNs with 3'-O-azidomethyl blocking group and LN3 linker moiety.

Example 4. Use of Palladium Scavenger in Sequencing Reaction

Figure 3:
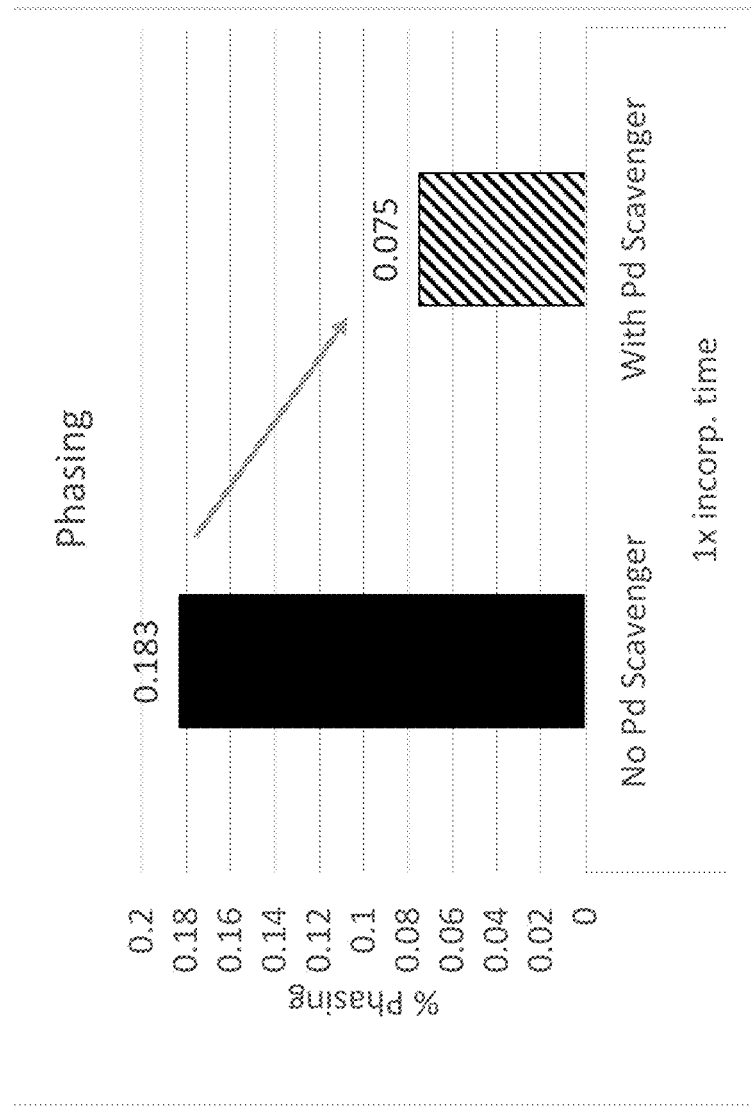
FIG. 3 illustrates a comparison of phasing value on Illumina's MiniSeq® instrument using fully functionalized nucleotides (ffNs) with 3'-AOM blocking group with and without using a palladium scavenger in the post cleavage washing step.

FIG. 3 illustrates a comparison of phasing value on Illumina's MiniSeq® instrument using fully functionalized nucleotides (ffNs) with 3'-AOM blocking group and standard LN3 linker moiety (including labeled ffT-DB, labeled ffAs and labeled ffC, and unlabeled ffG) with and without using potassium isocyanoacetate in the post cleavage washing step. The sequencing experiment was performed on an Illumina's MiniSeq® using a cartridge where the standard incorporation mix reagent was replaced by a freshly prepared incorporation mix containing ffNs with 3'-AOM blocking group and a standard LN3 linker moiety and where a freshly prepared solution of palladium cleavage reagent (10 mM [(Allyl)PdCl]$_2$, 100 mM THP, 100 mM ethanolamine buffer, 10 mM sodium ascorbate, 1M NaCl, 0.1% Tween 20) was added to an empty well. Potassium isocyanoacetate was added to the standard Miniseq® post-cleavage wash solution to a final concentration of 10 mM. The sequencing experiment was performed using a 2×151 cycles recipe which included, in addition to the standard sequencing-by-synthesis (SBS) protocols, a 5 seconds incubation with the solution of palladium cleavage reagent. As shown in FIG. 3, it was observed that when 10 mM potassium isocyanoacetate was used in the post-cleavage washing solution, the % phasing has been reduced from 0.183 to 0.075.

Figure 4:
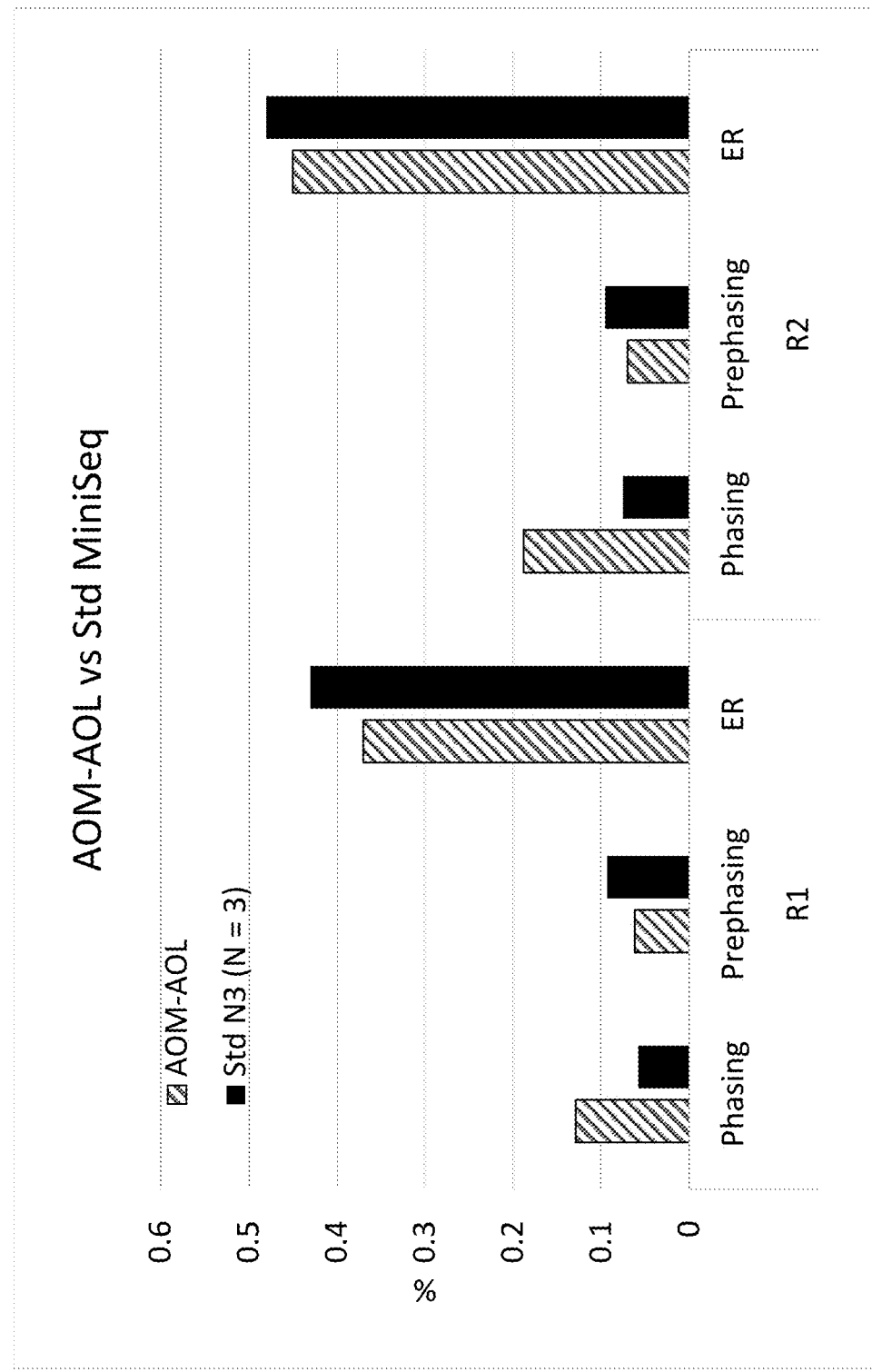
FIG. 4 illustrates the primary sequencing metrics including phasing, prephasing and error rate on Illumina's MiniSeq® instrument using fully functionalized nucleotides (ffNs) with 3'-AOM blocking group and AOL linker moiety when a palladium scavenger was used, as compared to the same sequencing metrics using standard ffNs with 3'-O-azidomethyl blocking group.

FIG. 4 illustrates the primary sequencing metrics including phasing, pre-phasing and error rate on Illumina's MiniSeq® instrument using fully functionalized nucleotides (ffNs) with 3'-AOM blocking group and AOL linker moiety (including labeled ffT-DB, labeled ffAs and labeled ffC, and unlabeled ffG) when a palladium scavenger was used, as compared to the same sequencing metrics using standard ffNs with 3'-O-azidomethyl blocking group and LN3 linker moiety. The sequencing experiment was performed on an Illumina's MiniSeq® by running a 2×151 cycle recipe using a standard cartridge where the incorporation mix reagent and the standard cleavage reagent were replaced by a freshly prepared incorporation mix containing fully functionalized nucleotides (ffNs) with 3'-AOM blocking group and AOL linker moiety and by a freshly prepared solution of palladium cleavage reagent (10 mM [(Allyl)PdCl]$_2$, 100 mM THP, 100 mM N,N'-diethylethanolamine buffer, 10 mM sodium ascorbate, 1M NaCl, 0.1% Tween 20), respectively. Potassium isocyanoacetate (ICNA) was added to the standard MiniSeq® post-cleave wash solution to a final concentration of 10 mM. The control sequencing experiments with the standard ffNs with 3'-O-azidomethyl blocking group were performed using standard MiniSeq® kits and recipes. Results showed an improvement in pre-phasing and more importantly error rates demonstrating the full efficiency of this AOM-AOL SBS chemistry with a single cleavage step.

Example 5. Use of Glycine in Sequencing Reaction

Figure 5:
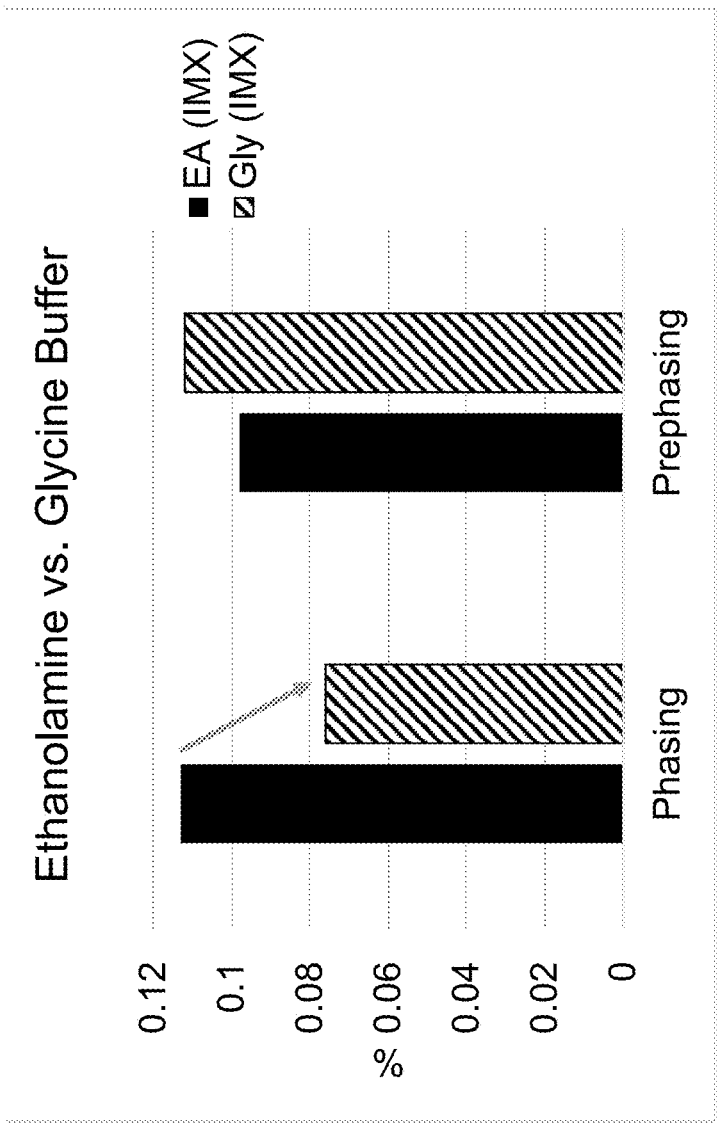
FIG. 5 illustrates a comparison of the primary sequencing metrics including phasing and pre-phasing on Illumina's MiniSeq® instrument using fully functionalized nucleotides (ffNs) with 3'-AOM blocking group and AOL linker moiety when glycine or ethanolamine is used in the incorporation mix respectively.

FIG. 5 illustrates a comparison of the primary sequencing metrics including phasing and pre-phasing on Illumina's MiniSeq® instrument using fully functionalized nucleotides (ffNs) with 3'-AOM blocking group and AOL linker moiety when glycine or ethanolamine is used in the incorporation mix respectively. In this example, the full set of ffNs include 3'-AOM-ffAs-AOL (labeled), 3'-AOM-ffG-AOL (unlabeled), 3'-AOM-ffT (DB)-AOL (labeled) and 3'-AOM-ffC (DB)-AOL (labeled). As shown in FIG. 5, it was observed that when glycine was used in the incorporation buffer, phasing value has decreased substantially when compared to a standard incorporation buffer containing ethanolamine. Although there was a slight increase in the prephasing value when glycine was used, it was not considered to be a meaningful increase. The sequencing experiment was performed on a standard MiniSeq® instrument using a cartridge where the standard incorporation mix reagent and the standard cleavage reagent were replaced by a freshly prepared incorporation mix containing fully functionalized nucleotides (ffNs) with 3'-AOM blocking group and AOL linker moiety in either 50 mM ethanolamine or 50 mM glycine buffer and by a freshly prepared solution of palladium cleavage reagent (10 mM [(Allyl)PdCl]$_2$, 100 mM THP, 100 mM N,N'-diethylethanolamine buffer, 10 mM sodium ascorbate, 1M NaCl, 0.1% Tween 20) respectively. Potassium isocyanoacetate (ICNA) was added to the standard MiniSeq post-cleave wash solution to a final concentration of 10 mM. A standard 2×151 cycles MiniSeq recipe was employed.

Figure 6:
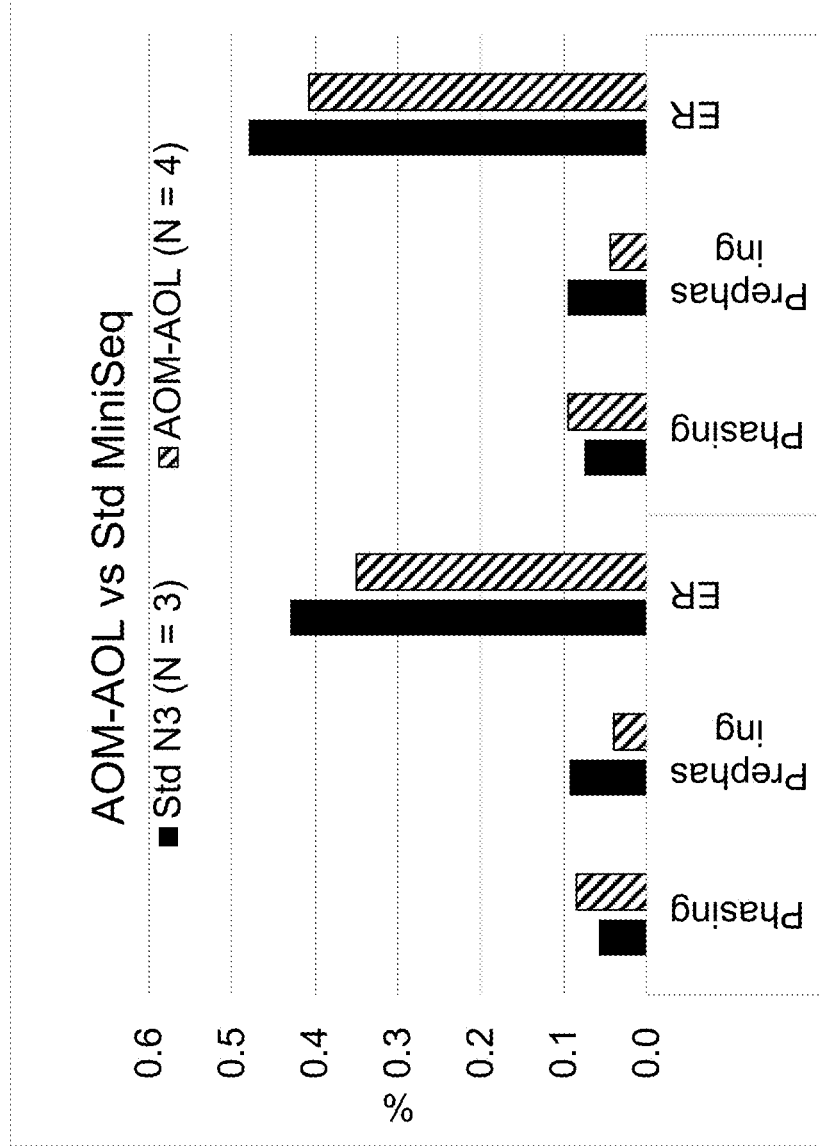
FIG. 6 illustrates the primary sequencing metrics including phasing, prephasing and error rate on Illumina's MiniSeq® instrument using fully functionalized nucleotides (ffNs) with 3'-AOM blocking group and AOL linker moiety when glycine was used in the incorporation mix, as compared to the same sequencing metrics using standard ffNs with 3'-O-azidomethyl blocking group.

FIG. 6 illustrates the primary sequencing metrics including phasing, pre-phasing and error rate on Illumina's MiniSeq® instrument using fully functionalized nucleotides (ffN) with 3'-AOM and AOL linker moiety as compared to the same sequencing metrics using standard ffNs and 3'-O-azidomethyl blocking group and LN3 linker moiety. In this example, the full set of ffNs include 3'-AOM-ffA-AOL (labeled), 3'-AOM-ffG-AOL (unlabeled), 3'-AOM-ffT (DB)-AOL (labeled) and 3'-AOM-ffC (DB)-AOL (labeled). The sequencing experiment was performed using a 2×151 cycle recipe on a standard MiniSeq® instrument loaded with a cartridge where the standard incorporation mix reagent and the standard cleavage reagent were replaced by a freshly prepared incorporation mix containing fully functionalized nucleotides (ffNs) with 3'-AOM blocking group in 50 mM glycine buffer and by a freshly prepared solution of palladium cleavage reagent (10 mM [(Allyl)PdCl]$_2$, 100 mM THP, 100 mM N,N'-diethylethanolamine buffer, 10 mM sodium ascorbate, 1M NaCl, 0.1% Tween 20) respectively. Potassium isocyanoacetate was added to the standard MiniSeq® post-cleave wash solution to a final concentration of 10 mM. Results showed further improvements in error rates compared to those achieved by the standard ffNs. It is believed that the improvement of phasing for the AOM-AOL series compared to FIG. 5 metrics is due to the use of the glycine buffer and the use of 3'-AOM-ffC (DB)-AOL.

Example 6. Sequencing by Synthesis on iSeq™

Figure 7A:
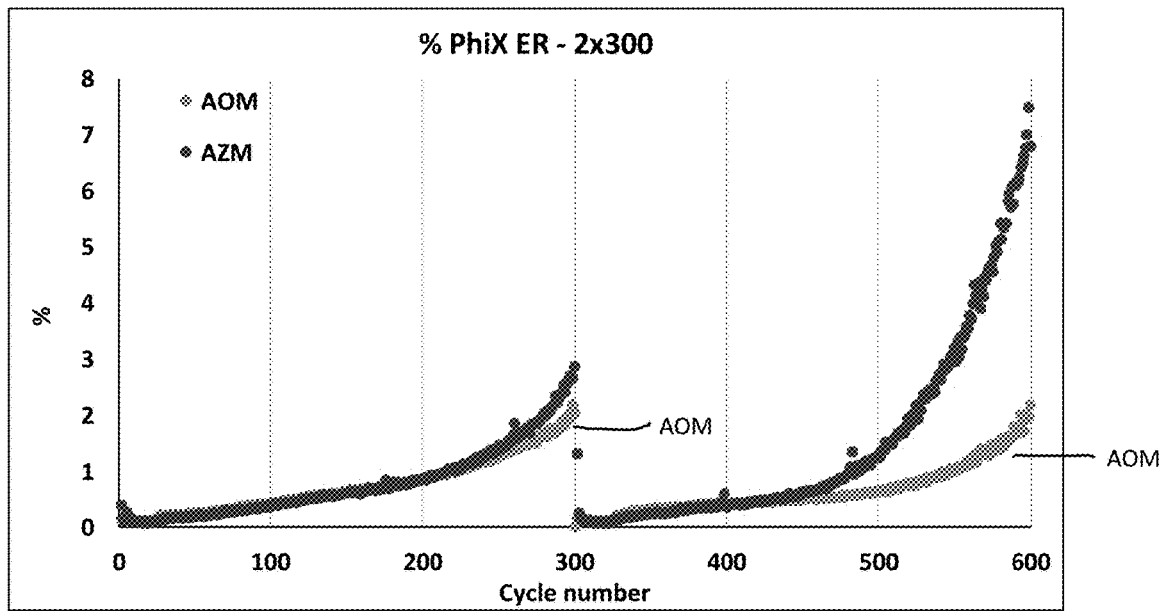
FIG. 7A and FIG. 7B illustrate error rate and Q30 sequencing metrics respectively of a 2×300 sequencing runs on Illumina's iSeq™ instrument using fully functionalized nucleotides (ffNs) with 3'-AOM blocking group and AOL linker moiety, as compared to the same sequencing metrics using standard ffNs with 3'-O-azidomethyl blocking group.
Figure 7B:
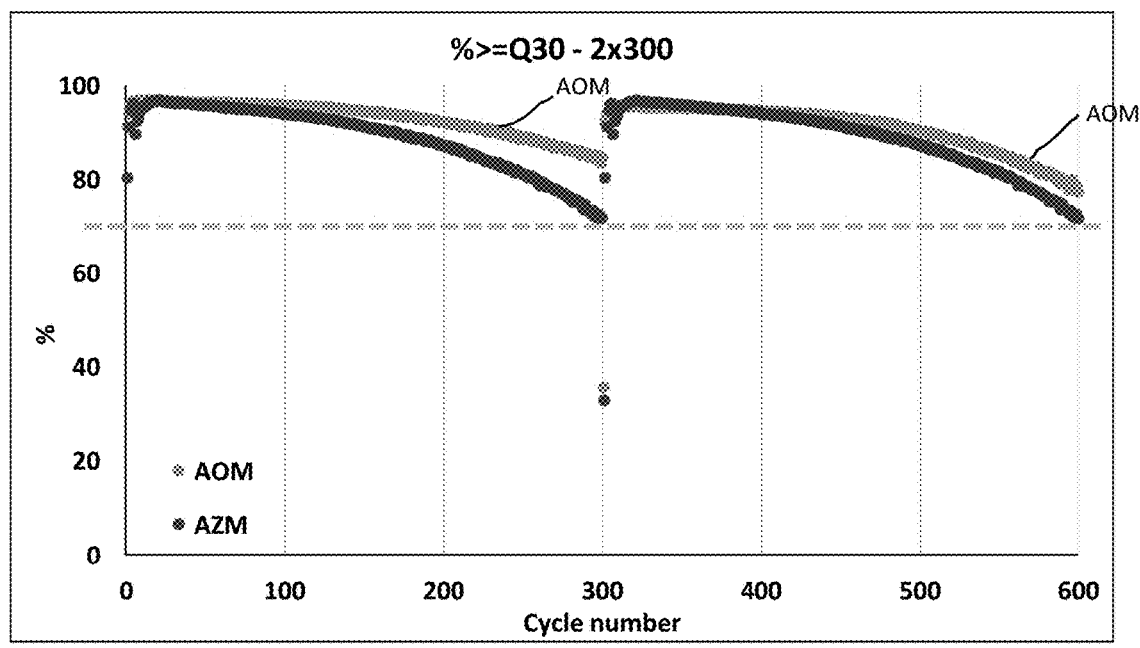

FIG. 7A and FIG. 7B illustrates a comparison of the primary sequencing metrics including error rate and Q30 score for sequencing by synthesis 2×300 cycles performed on Illumina's iSeq™ instrument using fully functionalized nucleotides (ffNs) with 3'-AOM blocking group and AOL linker moiety. In this example, the full set of AOM ffNs include 3'-AOM-ffA(DB)-AO-Dye 1, 3'-AOM-ffG (unlabeled), 3'-AOM-ffT(DB)-AOL-NR550S0, and 3'-AOM-ffC (DB)-AOL-Dye 2. The full set of azidomethyl (AZM) ffNs include the same ffNs having 3'-azidomethyl blocking group, propargylamido and LN3 linker. Dye 1 is a chromenoquinoline dye disclosed in U.S. Ser. No. 63/127,061, having the structure moiety

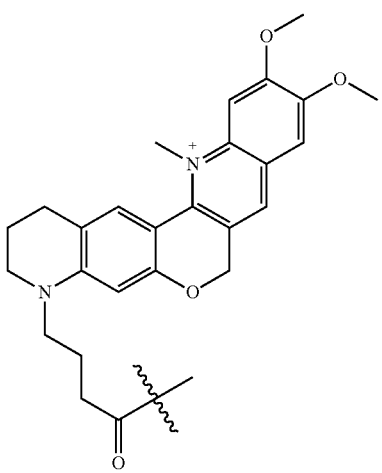

when conjugated with the ffA. Dye 2 is coumarin dye disclosed in U.S. Publication No. 2018/0094140, having the structure moiety

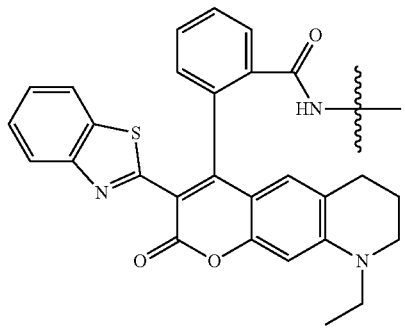 [SMILES: *NC(=O)c1ccccc1-c1c(-c2nc3ccccc3s2)c(=O)oc2cc3c(cc12)CCCN3CC]

when conjugated with the ffC. NR550S0 is a known green dye.

The sequencing experiment was performed on a standard iSeq™ instrument using a cartridge where the standard incorporation mix reagent and the standard cleavage reagent were replaced by a freshly prepared incorporation mix containing fully functionalized nucleotides (ffNs) with 3'-AOM blocking group and AOL linker moiety in either 50 mM ethanolamine or 50 mM glycine buffer using 300% concentration of Polymerase 1901 (Pol 1901) (360 ug/mL) and by a freshly prepared solution of palladium cleavage reagent (10 mM [(Allyl)PdCl]$_2$, 100 mM THP, 100 mM N,N'-diethylethanolamine buffer, 10 mM sodium ascorbate, 1M NaCl, 0.1% Tween 20) respectively. L-cysteine was added to the standard iSeq™ post-cleave wash solution to a final concentration of 10 mM. A 2×301 cycles iSeq™ recipe was employed in 2 excitations/1 emission protocol. In particular, the iSeq™ instrument was set up to take the first image with a green excitation light (~520 nm) and the second image with a blue excitation light (~450 nm). The standard sequencing recipe was used to perform the SBS cycle (incorporation, followed by imaging, followed by cleavage) for 2×301 cycles. The sequencing metrics are summarized in the table below.

It was observed that the AOM ffN set delivered great performance, providing superior error rate and Q30 for both Read 1 and Read 2. The phasing values using the AOM ffN set were comparable to those generated by the AZM ffN set. However, the AOM ffN set produced substantial lower prephasing values.

Figure 8A:
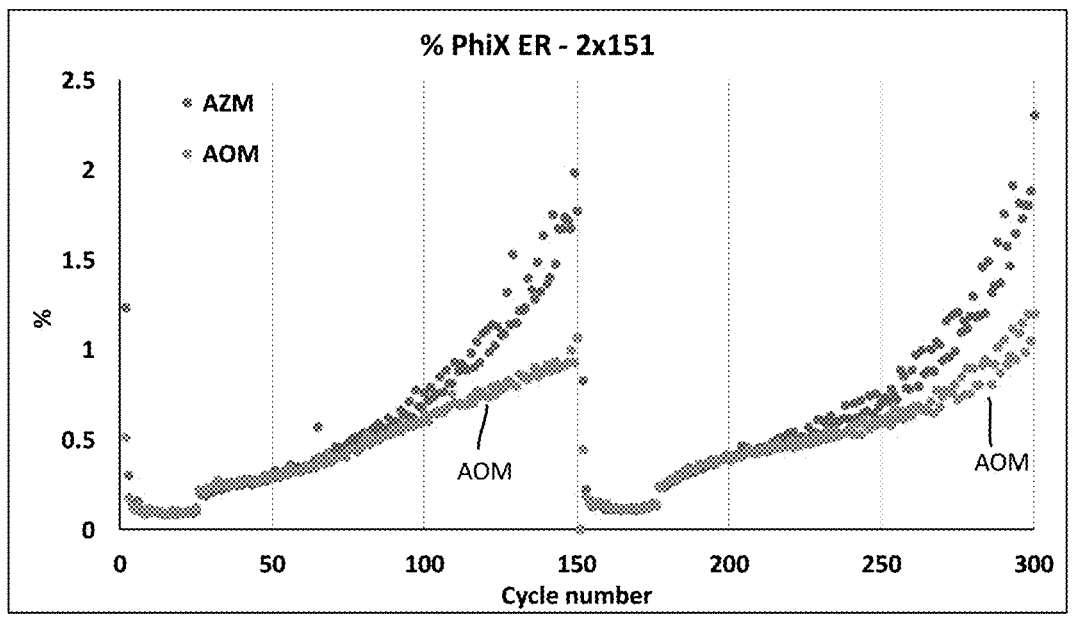
FIG. 8A and FIG. 8B illustrate error rate and Q30 sequencing metrics respectively of a 2×150 sequencing runs on Illumina's iSeq™ instrument using fully functionalized nucleotides (ffNs) with 3'-AOM blocking group and AOL linker moiety, as compared to the same sequencing metrics using standard ffNs with 3'-O-azidomethyl blocking group.
Figure 8B:
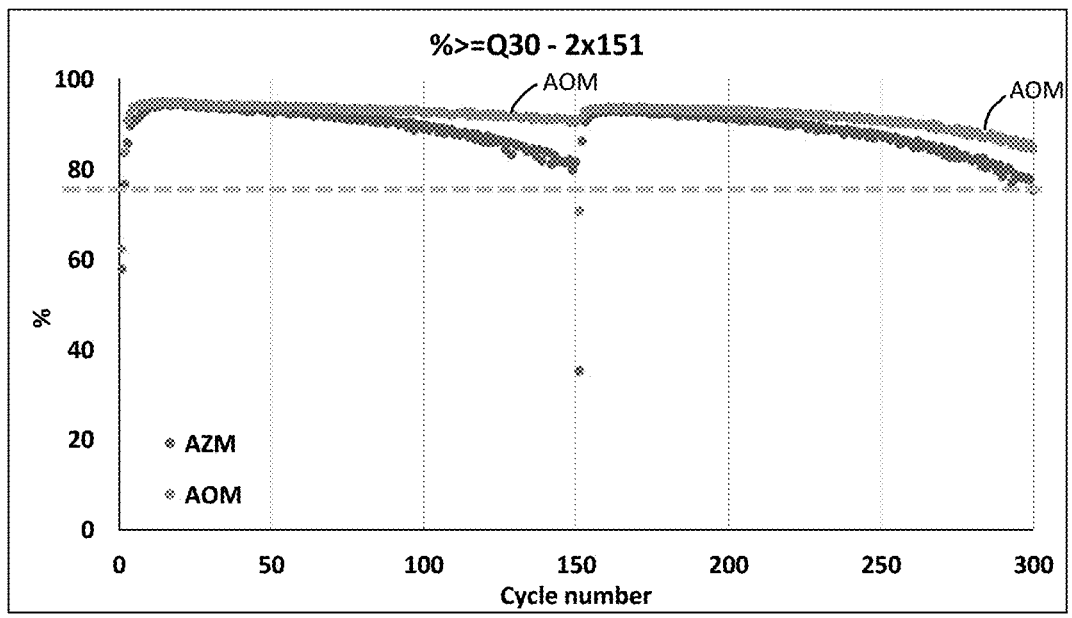

FIG. 8A and FIG. 8B illustrates a comparison of the primary sequencing metrics including error rate and Q30 score for sequencing by synthesis 2×150 cycles performed on Illumina's iSeq™ instrument using fully functionalized nucleotides (ffNs) with 3'-AOM blocking group and AOL linker moiety. In this example, the full set of AOM ffNs include 3'-AOM-ffA(DB)-AO-Dye 1, 3'-AOM-ffG (unlabeled), 3'-AOM-ffT(DB)-AOL-NR550S0, and 3'-AOM-ffC (DB)-AOL-Dye 2. The full set of AZM ffNs include the same ffNs having 3'-azidomethyl blocking group and propargylamido and LN3 linker. The sequencing experiment was performed on a standard iSeq™ instrument using a cartridge where the standard incorporation mix reagent and the standard cleavage reagent were replaced by a freshly prepared incorporation mix containing fully functionalized nucleotides (ffNs) with 3'-AOM blocking group and AOL linker moiety in either 50 mM ethanolamine or 50 mM glycine buffer using 300% concentration of Pol 1901 (360 ug/mL) and by a freshly prepared solution of palladium cleavage reagent (10 mM [(Allyl)PdCl]$_2$, 100 mM THP, 100 mM N,N'-diethylethanolamine buffer, 10 mM sodium ascorbate, 1M NaCl, 0.1% Tween 20) respectively. L-cysteine was added to the standard iSeq™ post-cleave wash solution to a final concentration of 10 mM. A 2×301 cycles iSeq™ recipe was employed in 2 excitations/1 emission protocol. In particular, the iSeq™ instrument was set up to take the first image with a green excitation light (~520 nm) and the second image with a blue excitation light (~450 nm). The standard sequencing recipe was used to perform the SBS cycle (incorporation, followed by imaging, followed by cleavage) for 2×301 cycles.

The incorporation mix contact time for the AZM ffNs were about 24.1 second, while the incorporation mix contact time for the AOM ffNs were about 29.1 seconds. However, the longer incorporation of the AOM ffNs were compensated by the faster deblocking time. The cleavage mix contact time was about 5.8 second in contrast to about 10.2 second for AZM ffN set. As such, the total incubation time for AZM and AOM ffNs set were about 34.4 and 34.9 respectively. The sequencing metrics are summarized in the table below.

|  | Read | Cycle time | PF (%) | Phasing | Prephasing | Error Rate (%) | Q30 (%) |
|---|---|---|---|---|---|---|---|
| AZM | 1 | 150.9 | 65.5 | 0.111 | 0.129 | 0.81 | 91.5 |
|  | 2 | 151.1 | 65.5 | 0.11 | 0.141 | 1.01 | 85.6 |
| AOM | 1 | 138.5 | 79.5 | 0.128 | 0.064 | 0.74 | 93.1 |
|  | 2 | 138.4 | 79.5 | 0.142 | 0.053 | 0.65 | 90.9 |

|  | Read | Cycle time | Total incubation time | PF (%) | Phasing | Prephasing | Error Rate (%) | Q30 (%) |
|---|---|---|---|---|---|---|---|---|
| AZM | 1 | 60.3 | 34.3 | 65.96 | 0.171 | 0.228 | 0.66 | 89.7 |
|  | 2 | 60.2 | 34.4 | 65.96 | 0.175 | 0.214 | 0.68 | 88.0 |
| AOM | 1 | 60.8 | 34.9 | 68.54 | 0.156 | 0.059 | 0.53 | 92.8 |
|  | 2 | 60.7 | 34.9 | 68.54 | 0.197 | 0.07 | 0.53 | 91.2 |

Again, it was observed that the AOM ffN set delivered great performance, providing superior error rate and Q30 for both Read 1 and Read 2. In addition, the AOM ffN set produced lower prephasing values.

Example 7. Sequencing by Synthesis on NovaSeq™ with Blue Laser Power Titration

It has been observed that long exposure to blue light in SBS sequencing causes high level of signal delay and phasing as a result of increased light dosage and power density. This example compares the performance of AOM ffNs and AZM ffNs in a blue laser titration sequencing experiment.

In this experiment, 1×151 runs SBS using a AOM ffN set on a modified blue/green excitation NovaSeq™ was compared to the standard ffN set with 3' azidomethyl blocking group and LN3 linker. The flowcell used were 490 nm pitch BEER2 flowcell. The power configuration for the blue laser power were: 600 mW, 800 mW, 1000 mW, 1400 mW, 1800 mW, and 2400 mW. The green laser power was constant at 1000 mM. The following standard AZM ffNs were used: Green ffT (LN3-AF550POPOS0), Dark G, Red ffC (LN3-SO7181), Blue ffC (sPA-blue dye A), Blue ffA (LN3-BL-blue dye A), Green ffA (LN3-BL-NR550S0). For the AOM ffN set, the following ffNs were used: Green ffT (ffT(DB)-AOL-AF550POPOS0), Dark G, Red ffC (ffC(DB)-AOL-SO7181), Blue ffC (ffC(DB)-AOL-blue dye A), Blue ffA (ffA(DB)-AOL-BL-blue dye A), Green ffA (ffA(DB)-AOL-BL-NR550S0). The structure of the blue dye labeled AOM ffC and ffA are illustrated below:

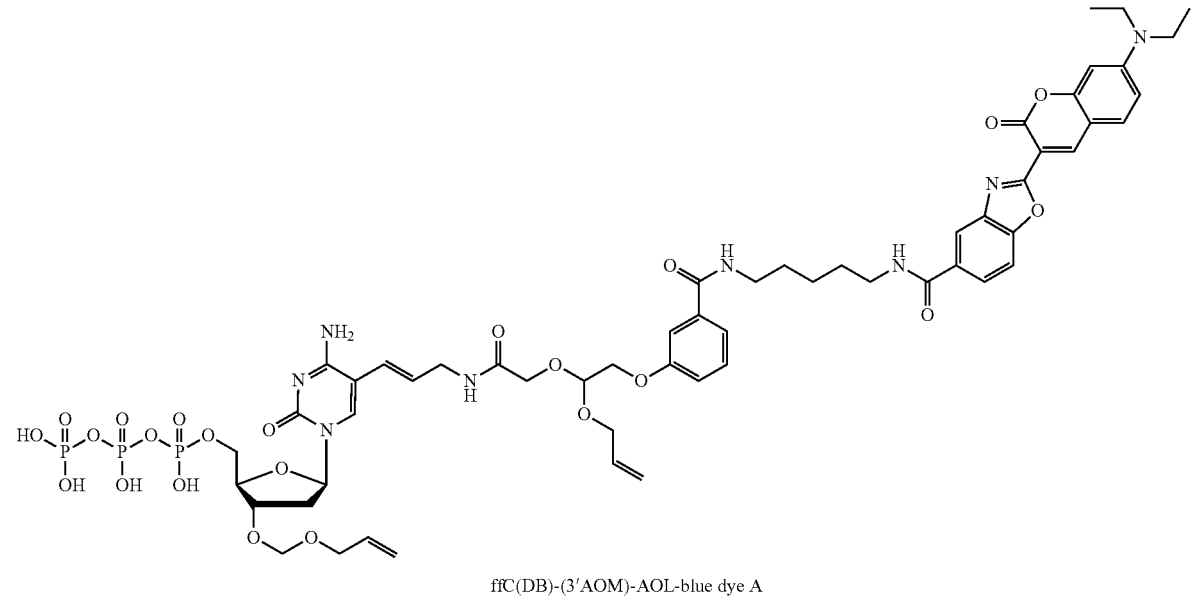

ffC(DB)-(3'AOM)-AOL-blue dye A

-continued

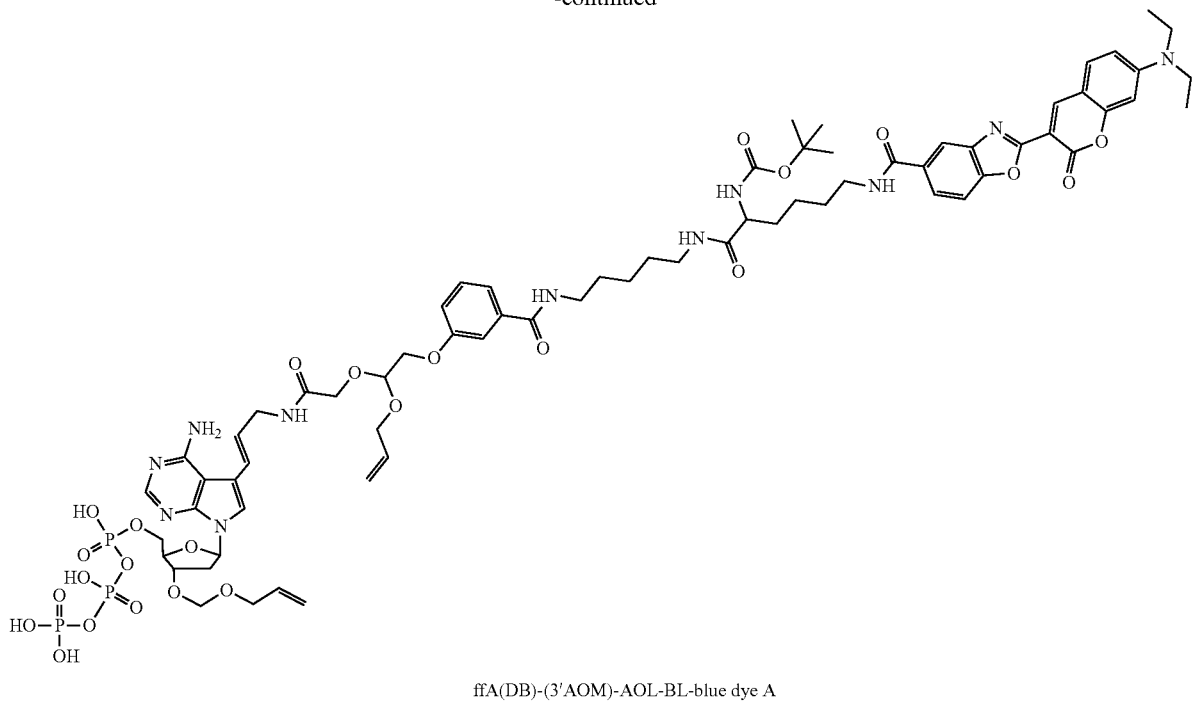

ffA(DB)-(3'AOM)-AOL-BL-blue dye A

Figure 9A:
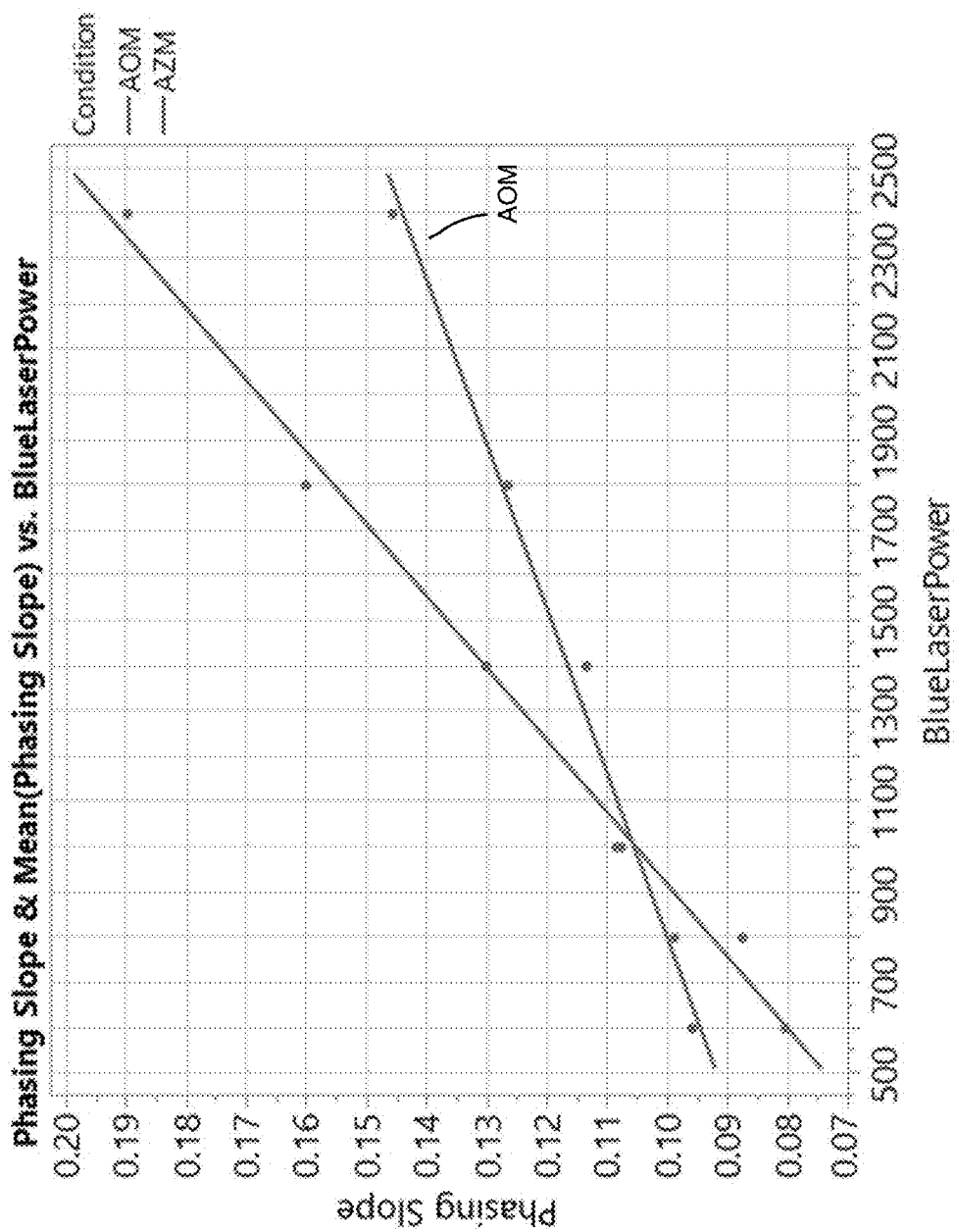
FIGS. 9A-9E illustrate the primary sequencing metrics (phasing, percent signal decay, error rate) as a function of blue laser powers when the green laser power was constant. The sequencing experiments were performed on Illumina's NovaSeq™ instrument using fully functionalized nucleotides (ffNs) with 3'-AOM blocking group and AOL linker moiety when a palladium scavenger L-cysteine was used, as compared to the same sequencing metrics using standard protocols and ffNs with 3'-O-azidomethyl blocking group.
Figure 9B:
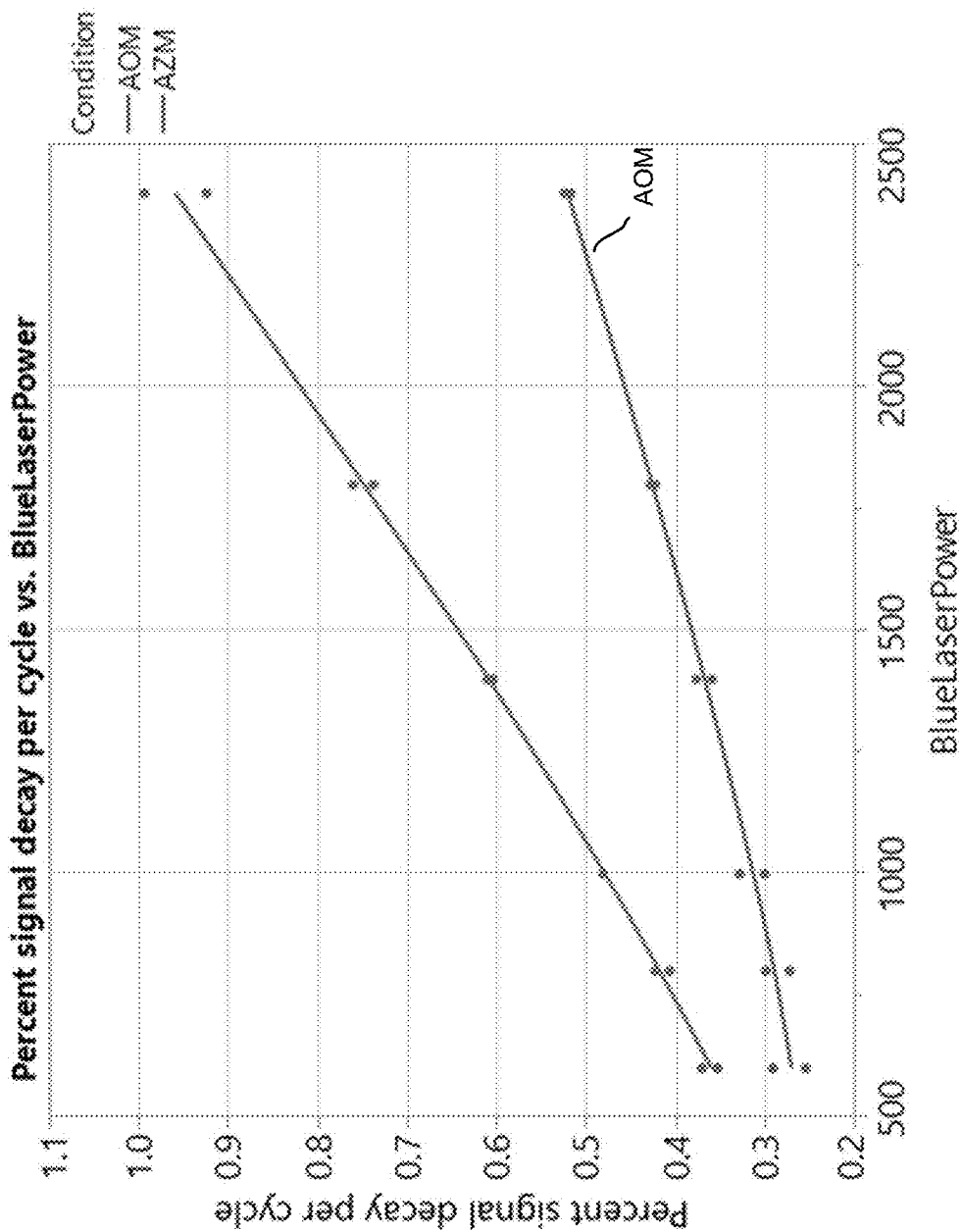
Figure 9C:
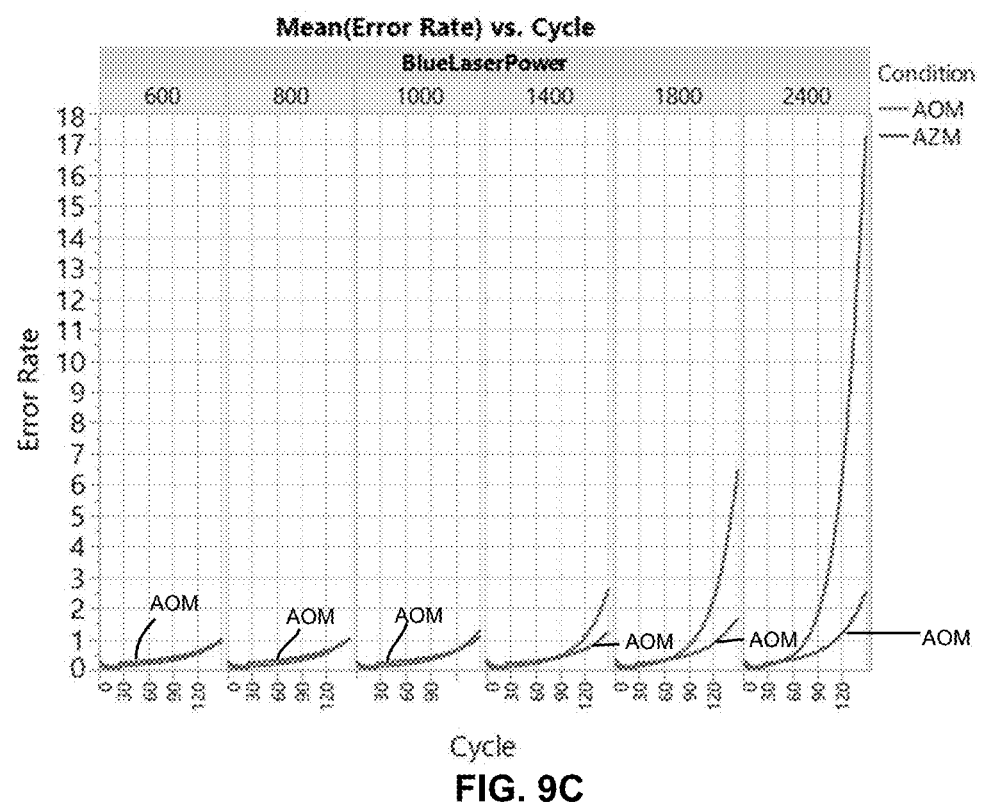
Figure 9D:
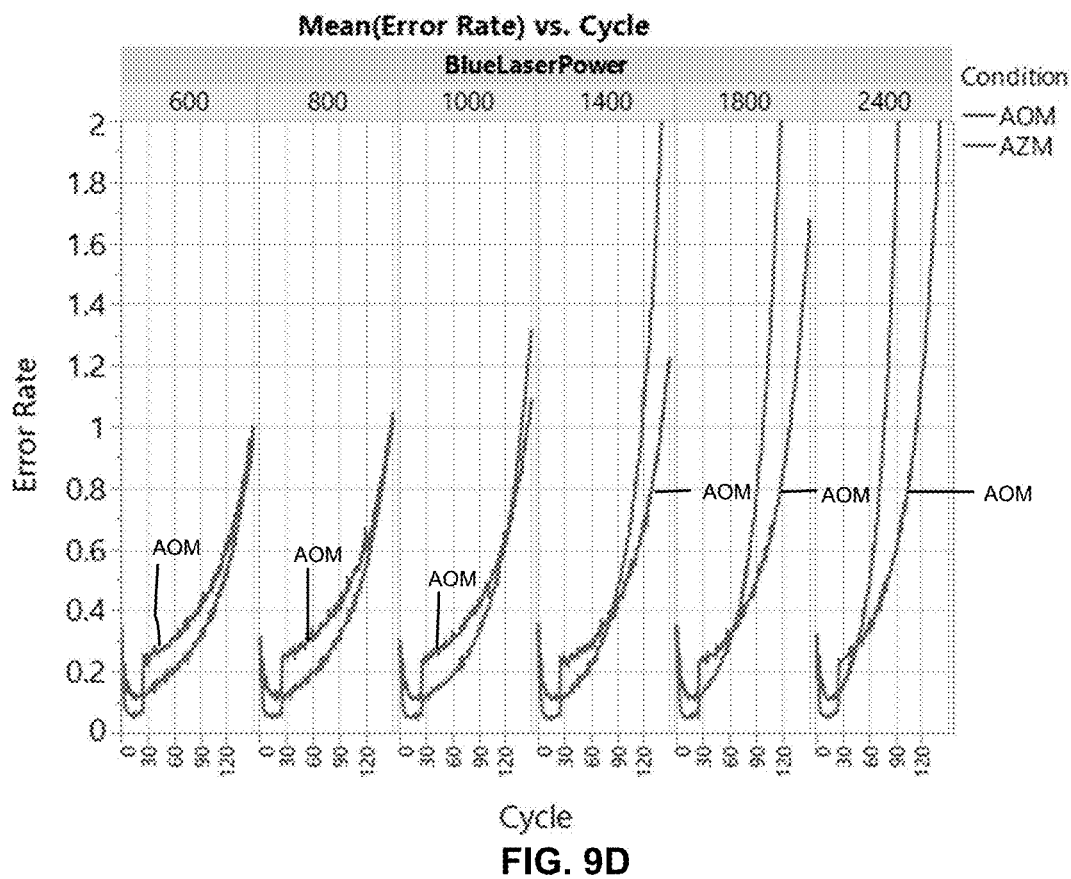
Figure 9E:
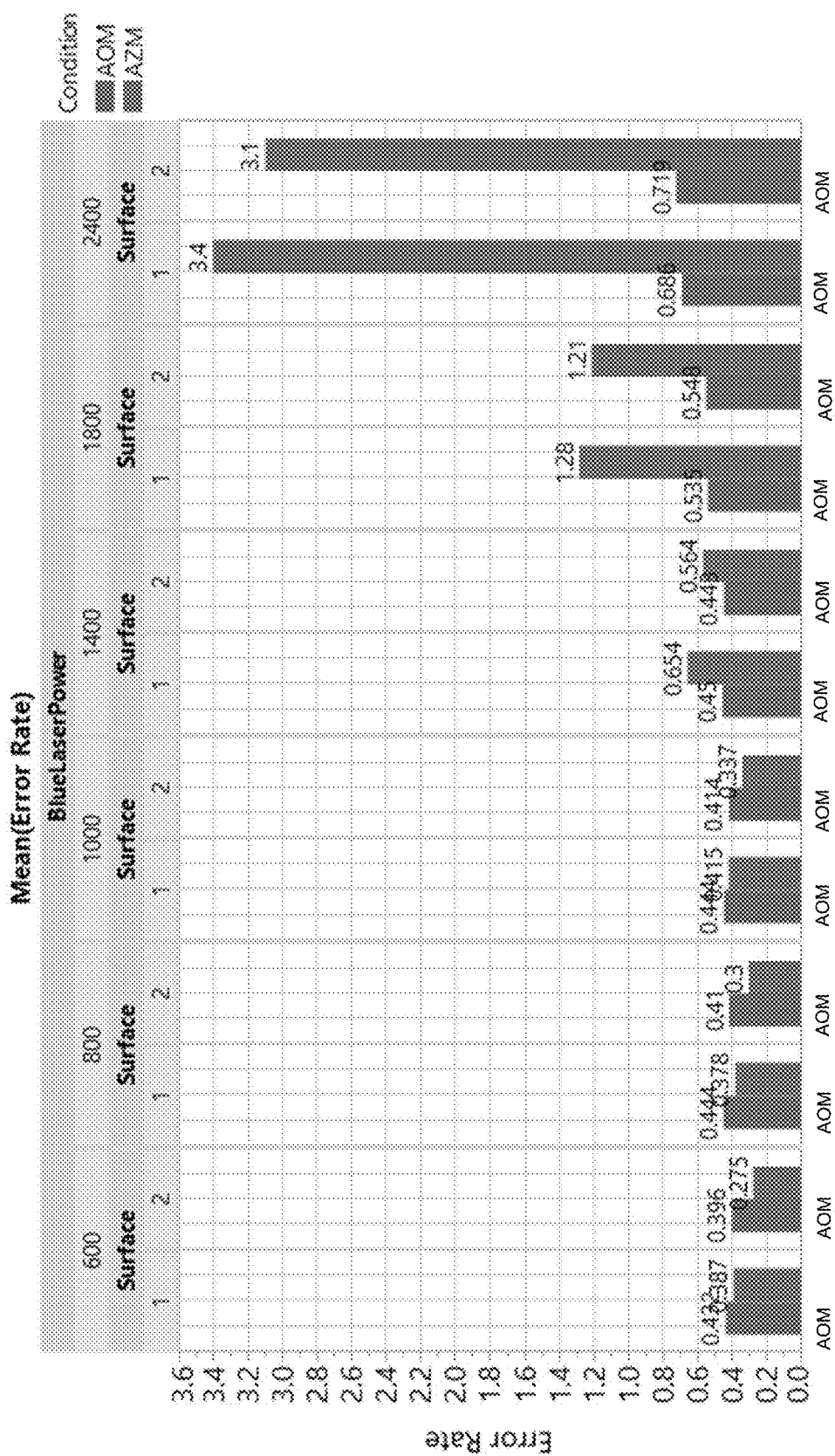

For AOM ffN set SBS runs, the following modifications were made. First, 10 mM L-cysteine was added to the post-cleavage washing solution. The cleave mix include the following components: $Na_2PdCl_4$ in DEEA buffer. Two 10 seconds wait steps were added to post cleavage wash step. In addition, 60 seconds static incorporation wait time was used (in contrast to 38 s for AZM ffNs). FIG. 9A shows that both ffN sets had similar phasing values at lower blue laser powers, but the AOM ffN set was less sensitive to the increased blue laser power titration (indicated by a gentle phasing slope as compared to that of the AZM phasing slope). In addition, it was also observed that the AOM ffNs had much lower prephasing. As illustrated in FIG. 9B, the AOM ffN set had significantly less signal decay at higher blue laser powers. FIGS. 9C and 9D illustrate the mean error rate as a function of cycle number. FIG. 9D is a magnified view of FIG. 9C. The results show that although the AZM ffNs had lower error rate at early cycles at lower blue laser power, the AOM ffN set performed much better at later cycles with higher blue laser powers. FIG. 9E summaries the average error rate at 151 cycle. Again, the AOM ffN set outperformed the AZM ffN set at high laser powers (e.g., at 1400 mW, 1800 mW and 2400 mW).

Example 8. First Chemical Linearization Using Pd Cleavage Mix

Figure 10:
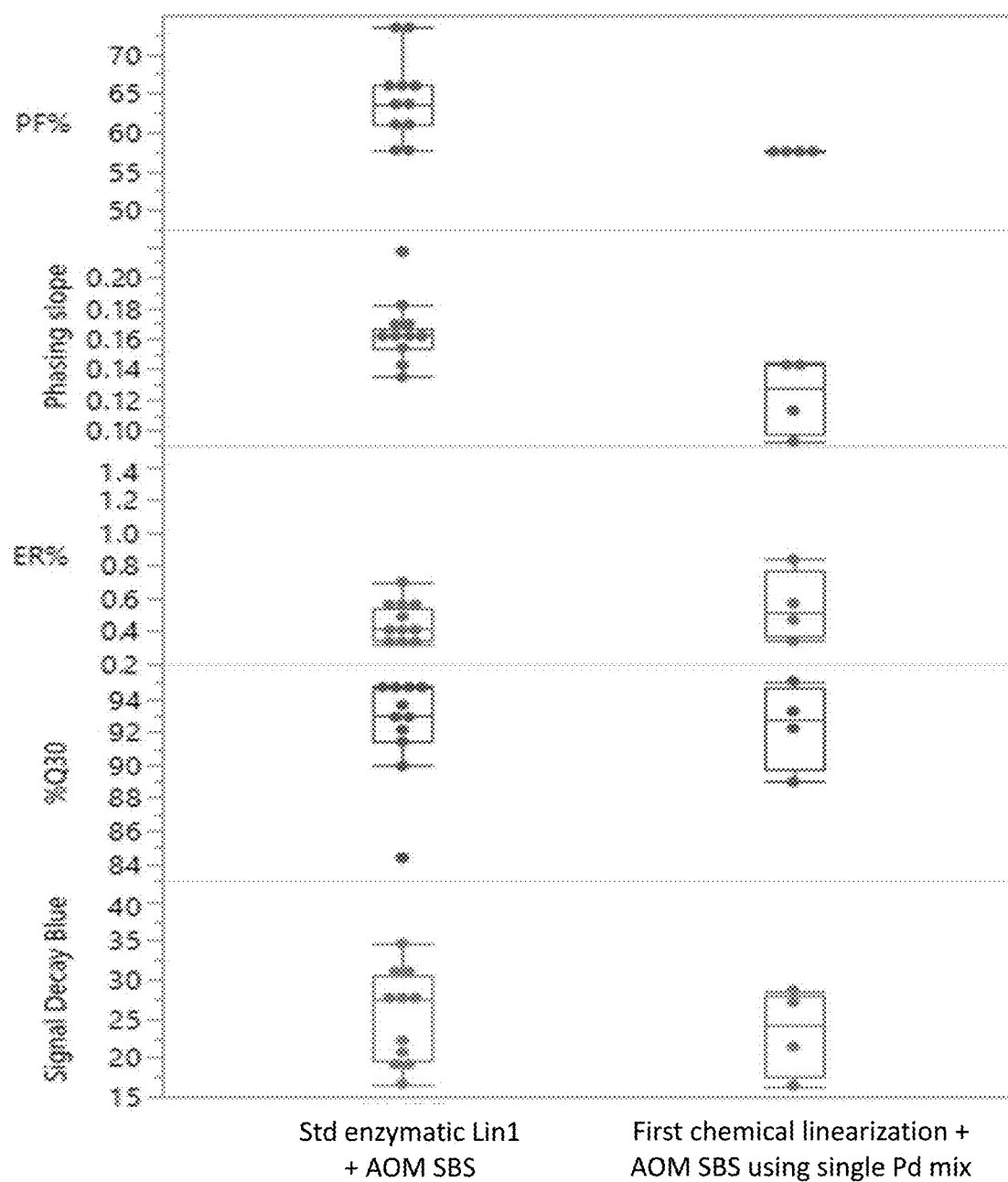
FIG. 10 illustrates the primary sequencing metrics (% PF, error rate, Q30 and signal decay) on Illumina's iSeq™ instrument (1×150 cycles) using fully functionalized (ffNs) with 3'-AOM blocking group and AOL linker moiety in which the same palladium cleavage mix was also used in the first step of chemical linearization of the SBS, as compared to the SBS of the same ffNs using standard enzymatic linearization.

In this example, the Pd cleavage mix used in the SBS was tested in the first chemical linearization step after clustering step. The experiment compared the chemical linearization to the standard enzymatic linearization where the cleavage of one of the double stranded polynucleotides was facilitated by USER to cleave the U position on the P5 primer. A 1×150 cycles SBS was conducted on Illumina's iSeq™ instrument using fully functionalized nucleotides (ffNs) with 3'-AOM blocking group and AOL linker moiety. In this example, the full set of AOM ffNs include 3'-AOM-ffA(DB)-AO-Dye 1, 3'-AOM-ffG (unlabeled), 3'-AOM-ffT(DB)-AOL-NR550S0, and 3'-AOM-ffC(DB)-AOL-Dye 2 as described in Example 6. The iSeq™ instrument was set up to take the first image with a green excitation light (~520 nm) and the second image with a blue excitation light (~450 nm) (employing the 2 excitations/1 emission protocols). The flow cell used on the iSeq™ instrument was grafted with modified P5/P7 primers to allow first chemical linearization of the P5 primer. The chemical linearization step was conducted in a Pd cleavage mix (10 mM of $[Pd(allyl)Cl]_2$ and 100 mM THP in a buffer solution containing DEEA) incubated 30 s at 63° C. The SBS sequencing metrics using the two different linearization methods is illustrated in FIG. 10. It was observed that all primary sequencing metrics fall within the standard observed range when the Pd cleavage mix was used in the first chemical linearization step. This experiment confirms that a single reagent mix may be used in two separate steps of sequencing—linearization step and the SBS cleaving step, which allows for further instrument (fluidic and cartridges) simplification.

What is claimed is:

1. A nucleoside or nucleotide comprising a nucleobase attached to a detectable label via a cleavable linker, wherein the nucleoside or nucleotide has the structure of Formula (I):

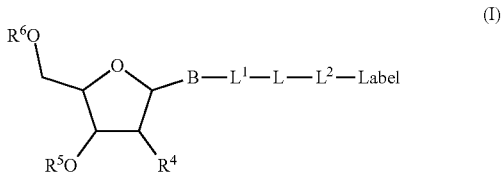

(I)

wherein B is the nucleobase;

R⁴ is H or OH;
R⁵ is

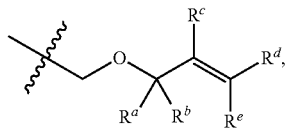

and each of $R^a$, $R^b$, $R^c$, $R^d$ and $R^e$ is independently H, halogen, or unsubstituted or substituted $C_1$-$C_6$ alkyl;

R⁶ is H, a hydroxy protecting group, or a reactive phosphorous containing group, or —OR⁶ is a monophosphate, diphosphate, triphosphate, thiophosphate, or a phosphate ester analog;

L is

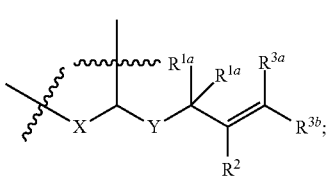

wherein
each of X and Y is independently O or S;
each of $R^{1a}$, $R^{1b}$, $R^2$, $R^{3a}$ and $R^{3b}$ is independently H, halogen, or unsubstituted or substituted $C_1$-$C_6$ alkyl; and
each of $L^1$ and $L^2$ is independently an optionally present linker moiety.

2. The nucleoside or nucleotide of claim 1,
wherein the detectable label is a fluorescent dye;
each of $R^a$, $R^b$, $R^c$, $R^d$ and $R^e$ is independently H, halogen, unsubstituted $C_1$-$C_6$ alkyl, or $C_1$-$C_6$ haloalkyl; and
each of $R^{1a}$, $R^{1b}$, $R^2$, $R^{3a}$ and $R^{3b}$ is independently H, halogen, unsubstituted $C_1$-$C_6$ alkyl, or $C_1$-$C_6$ haloalkyl.

3. The nucleoside or nucleotide of claim 1, wherein each of X and Y is O.

4. The nucleoside or nucleotide of claim 1, wherein each of $R^{1a}$, $R^{1b}$, $R^2$, $R^{3a}$ and $R^{3b}$ is H.

5. The nucleoside or nucleotide of claim 1, wherein at least one of $R^{1a}$, $R^{1b}$, $R^2$, $R^{3a}$ and $R^{3b}$ is halogen or unsubstituted $C_1$-$C_6$ alkyl.

6. The nucleoside or nucleotide of claim 1, wherein B is a purine, a deaza purine, or a pyrimidine.

7. The nucleoside or nucleotide of claim 1, wherein R⁵ is

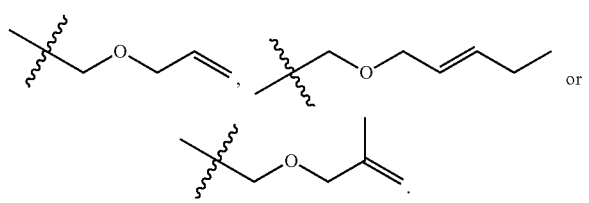

8. The nucleoside or nucleotide of claim 1, wherein $L^1$ is present, and $L^1$ comprises a moiety selected from the group consisting of a propargylamine, a propargylamide, an allylamine, an allylamide, and optionally substituted variants thereof.

9. The nucleoside or nucleotide of claim 8, wherein $L^1$ comprises

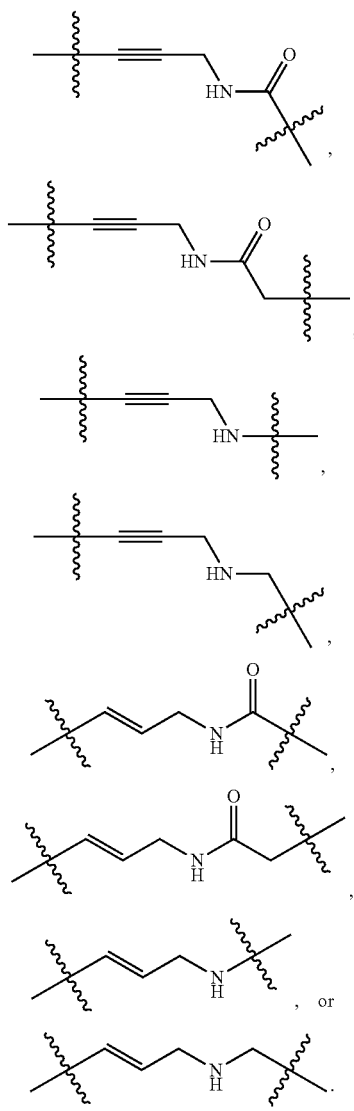

10. The nucleoside or nucleotide of claim 1, comprising the structure of Formula (Ia), (Ia'), (Ib), (Ic), (Ic') or (Id):

(Ia)

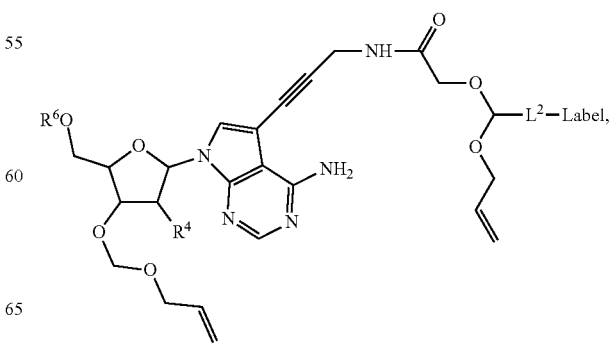

(Ia')

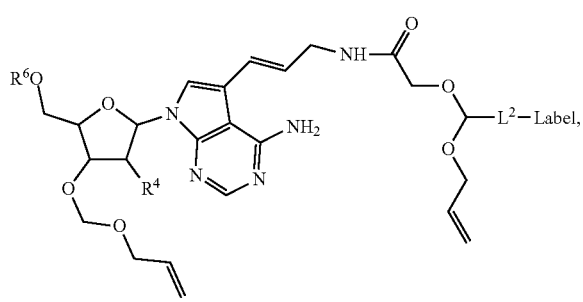

(Ib)

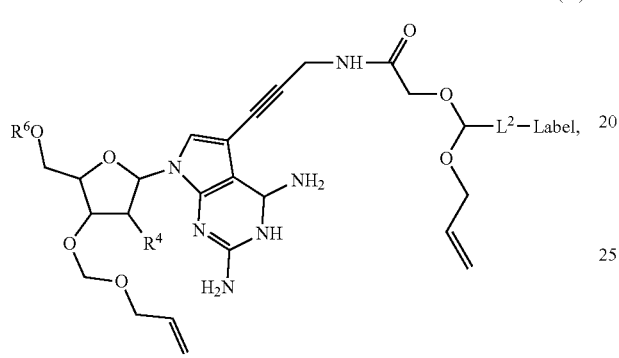

(Ic)

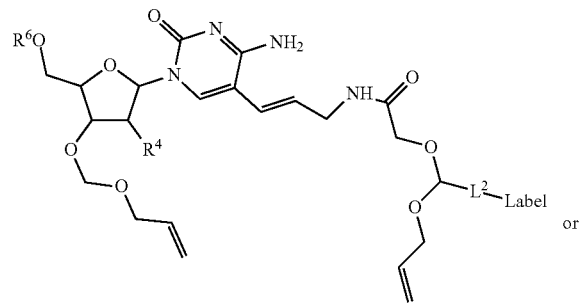

(Ic')

(Id)

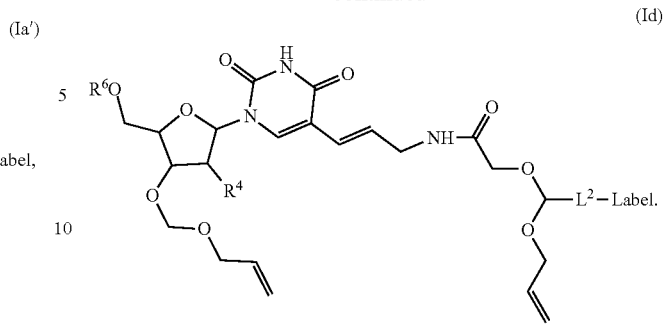

11. The nucleoside or nucleotide of claim 1, wherein $L^2$ is present, and $L^2$ comprises

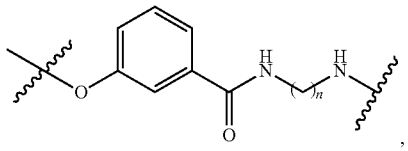

,

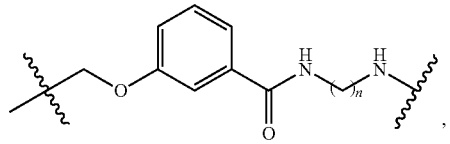

, or

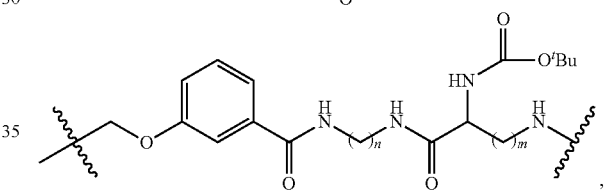

, wherein each of m and n is independently an integer of 1, 2, 3, 4, 5, 6, 7, 8, 9 or 10, and the phenyl moiety is optionally substituted.

12. The nucleoside or nucleotide of claim 11, wherein n is 5.

13. The nucleoside or nucleotide of claim 11, wherein m is 4.

14. The nucleoside or nucleotide of claim 1, wherein $R^4$ is H and $-OR^6$ is a triphosphate.

15. The nucleoside or nucleotide of claim 10, wherein $R^4$ is H and $-OR^6$ is a triphosphate.

16. The nucleotide of claim 15, wherein $L^2$ is present, and $L^2$ comprises

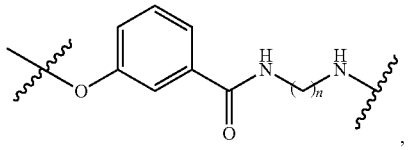

,

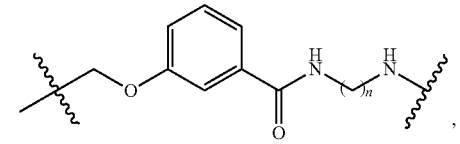

, or

-continued

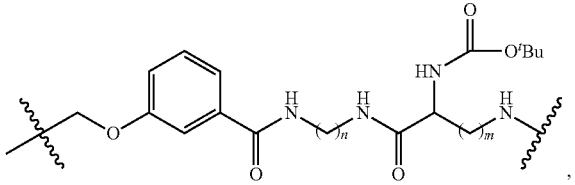

wherein each of m and n is independently an integer of 1, 2, 3, 4, 5, 6, 7, 8, 9 or 10, and the phenyl moiety is optionally substituted.

17. The nucleotide of claim 16, wherein n is 5.

18. An oligonucleotide or polynucleotide comprising the nucleotide of claim 14.

19. The oligonucleotide or polynucleotide of claim 18, wherein the oligonucleotide or polynucleotide is hybridized to a template polynucleotide.

20. The oligonucleotide or polynucleotide of claim 19, wherein the template polynucleotide is immobilized on a solid support.

21. The oligonucleotide or polynucleotide of claim 20, wherein the solid support comprises an array of a plurality of immobilized template polynucleotides.

22. An oligonucleotide or polynucleotide comprising the nucleotide of claim 15.

23. A method of preparing a growing polynucleotide complementary to a target single-stranded polynucleotide in a sequencing reaction, comprising incorporating the nucleotide of claim 14 into a growing complementary polynucleotide, wherein the incorporation of the nucleotide prevents the introduction of any subsequent nucleotide into the growing complementary polynucleotide.

24. A method of determining the sequence of a target single-stranded polynucleotide, comprising:
(a) incorporating the nucleotide of claim 14 into a copy polynucleotide strand complementary to at least a portion of the target polynucleotide strand;
(b) detecting the identity of the nucleotide incorporated into the copy polynucleotide strand; and
(c) chemically removing the detectable label and the 3'-OH blocking group from the nucleotide incorporated into the copy polynucleotide strand.

25. A kit comprising one or more nucleotides of claim 14.

26. The kit of claim 25, further comprising an enzyme, at least one Pd(0) scavenger, and one or more buffering agents.

27. The kit of claim 26, wherein the enzyme is a DNA polymerase, a terminal deoxynucleotidyl transferase, or a reverse transcriptase.

28. The kit of claim 26, wherein the at least one Pd(0) scavenger comprises one or more allyl moieties each independently selected from the group consisting of —O-allyl, —S-allyl, —NR-allyl, and —N+RR'-allyl,
wherein R is H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_6$-$C_{10}$ aryl, unsubstituted or substituted 5 to 10 membered heteroaryl, unsubstituted or substituted $C_3$-$C_{10}$ carbocyclyl, or unsubstituted or substituted 5 to 10 membered heterocyclyl; and
R' is H, unsubstituted $C_1$-$C_6$ alkyl or substituted $C_1$-$C_6$ alkyl.

29. The kit of claim 28, wherein the at least one Pd(0) scavenger is:

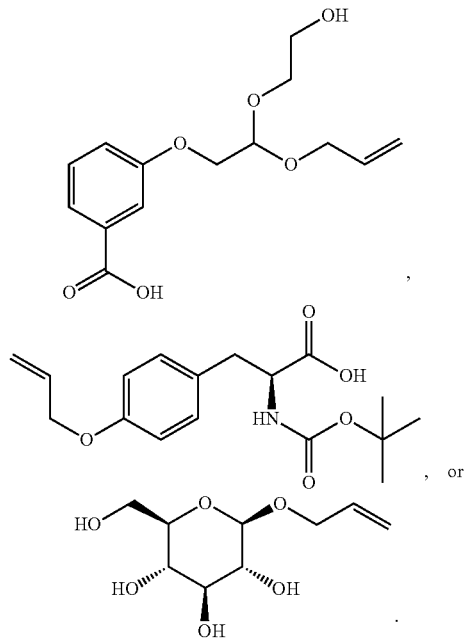

30. The kit of claim 25, further comprising a palladium catalyst.

31. The kit of claim 30, wherein the palladium catalyst is a Pd(0) catalyst generated in situ from a Pd(II) complex and one or more water soluble phosphines.

32. The kit of claim 31, wherein the Pd(II) complex is [Pd(Allyl)Cl]$_2$ or Na$_2$PdCl$_4$.

33. The kit of claim 31, further comprising one or more Pd(II) scavengers.

34. The kit of claim 33, wherein the one or more Pd(II) scavengers are selected from the group consisting of an isocyanoacetate (ICNA) salt, ethyl isocyanoacetate, methyl isocyanoacetate, cysteine or a salt thereof, L-cysteine or a salt thereof, N-acetyl-L-cysteine, potassium ethylxanthogenate, potassium isopropyl xanthate, glutathione, lipoic acid, ethylenediaminetetraacetic acid (EDTA), iminodiacetic acid, nitrilodiacetic acid, trimercapto-S-triazine, dimethyldithiocarbamate, dithiothreitol, mercaptoethanol, allyl alcohol, propargyl alcohol, thiol, tertiary amine, tertiary phosphine, and combinations thereof.

35. A kit comprising one or more nucleotides of claim 15.

36. The kit of claim 35, further comprising a DNA polymerase, at least one Pd(0) scavenger, and one or more buffering agents.

* * * * *

UNITED STATES PATENT AND TRADEMARK OFFICE
CERTIFICATE OF CORRECTION

PATENT NO. : 11,787,831 B2
APPLICATION NO. : 17/353512
DATED : October 17, 2023
INVENTOR(S) : Antoine Francais et al.

It is certified that error appears in the above-identified patent and that said Letters Patent is hereby corrected as shown below:

In the Specification

Column 9, Line 18, delete "isoxazollylalkyl," and insert -- isoxazolylalkyl, --.

Column 10, Line 57, delete "$R_b$" and insert -- $R_B$ --.

Column 26, Lines 49-58 (approx.), delete " 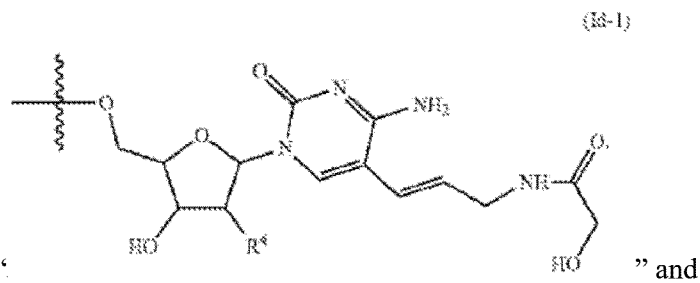 " and insert -- 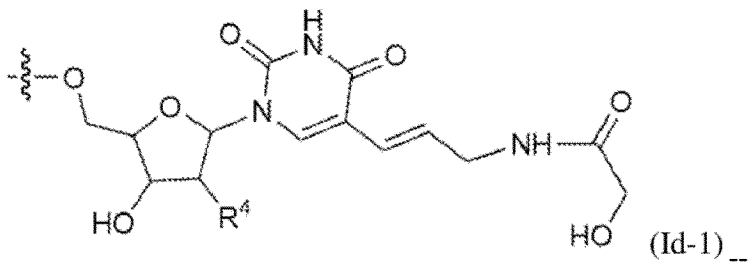 --.

Column 58, Line 43, delete "Pd(Allyl)Cl]$_2$" and insert -- [Pd(Allyl)Cl]$_2$ --.

Column 58, Line 45, delete "Pd(Allyl)Cl]$_2$" and insert -- [Pd(Allyl)Cl]$_2$ --.

Column 62, Line 65, delete "mol)." and insert -- μmol). --.

Column 63, Line 24 (approx.), delete "mol)." and insert -- μmol). --.

Signed and Sealed this
Twentieth Day of August, 2024

Katherine Kelly Vidal
*Director of the United States Patent and Trademark Office*

CERTIFICATE OF CORRECTION (continued)
U.S. Pat. No. 11,787,831 B2

Columns 69-70, Line 2 (approx.), delete "5′-triphosphate-3′-AOM-A(DB) nucleotide" and insert
-- 5′-triphosphate-3′-AOM-C(DB) nucleotide --.

Column 69-70, Lines 3-37 (approx.), delete

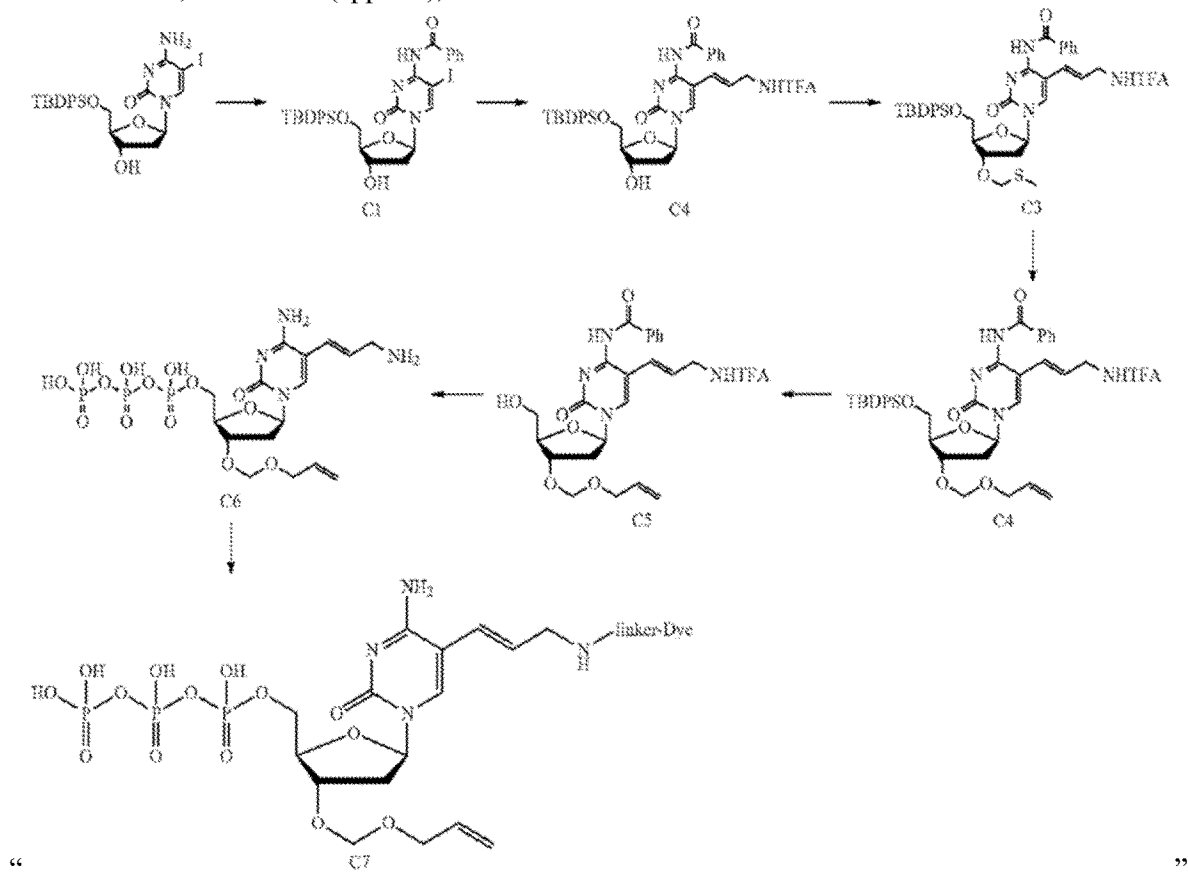

"
and insert

CERTIFICATE OF CORRECTION (continued)
U.S. Pat. No. 11,787,831 B2

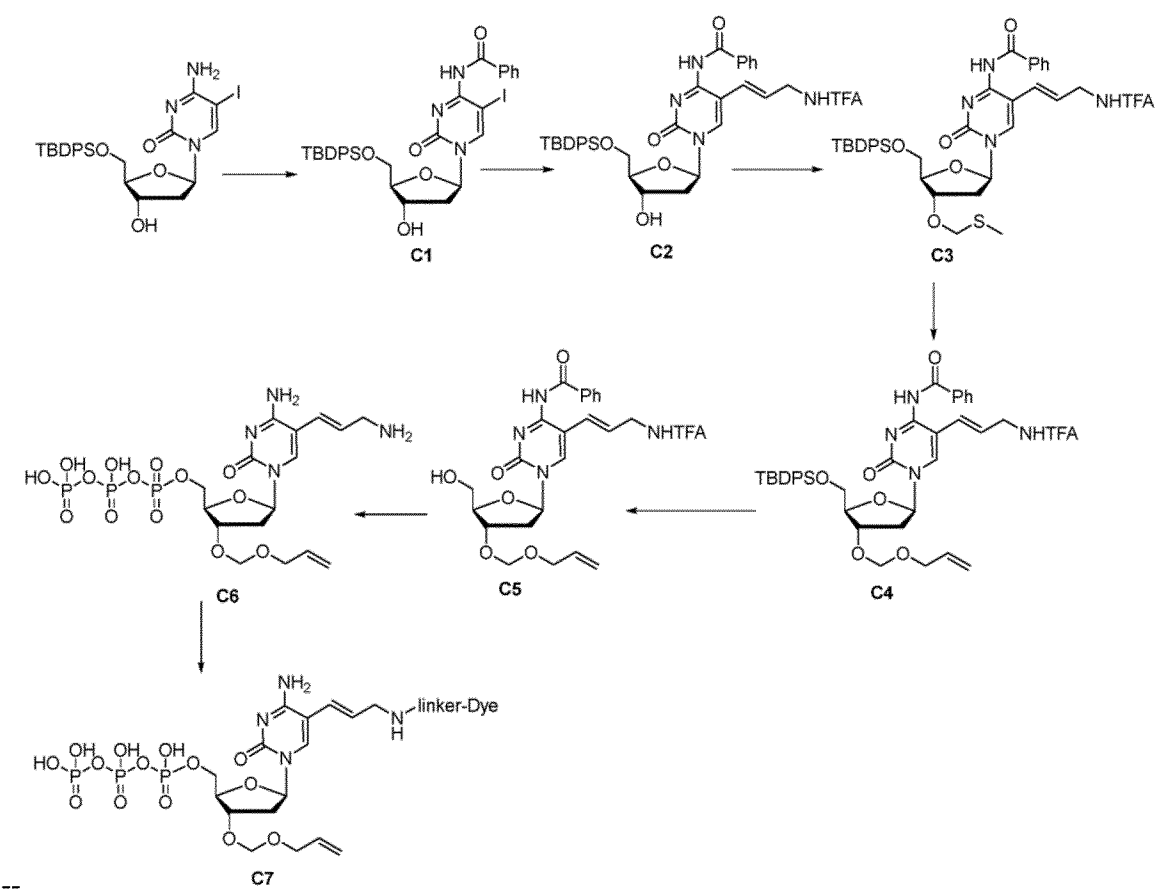

Columns 77-78, Lines 30-60 (approx.), delete

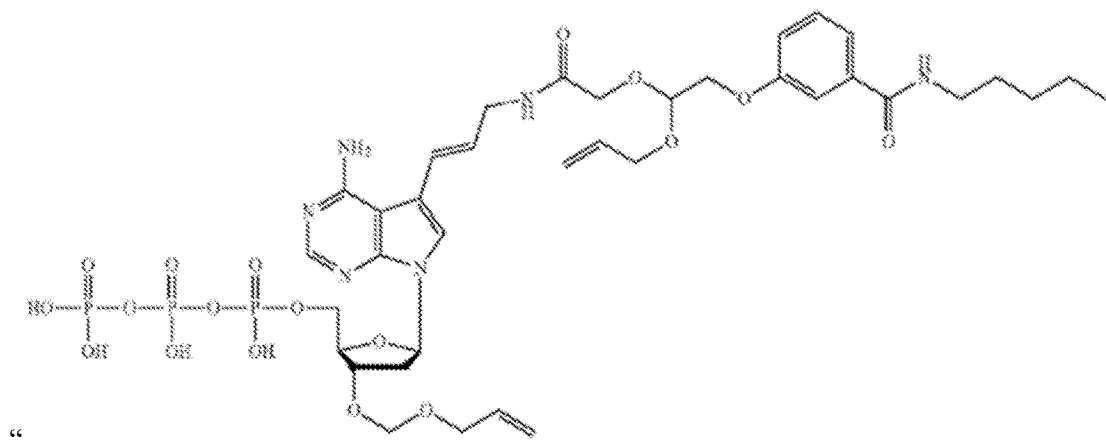

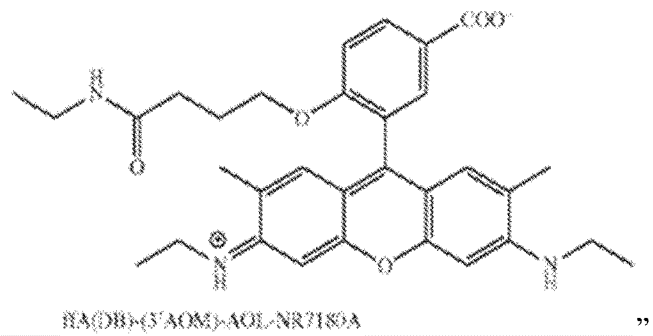
"
and insert
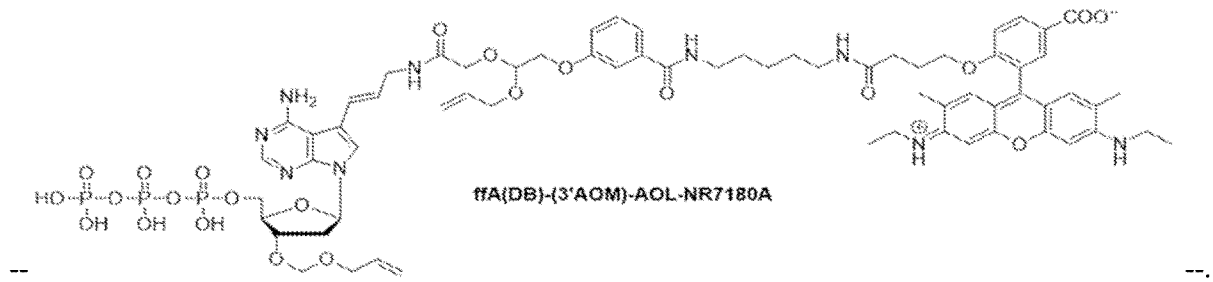
--  --.
Column 77, Line 66 (approx.), delete "mol)." and insert -- μmol). --.
Column 79, Line 21 (approx.), delete "mol)." and insert -- μmol). --.

CERTIFICATE OF CORRECTION (continued)
U.S. Pat. No. 11,787,831 B2

Columns 79-80, Lines 24-61 (approx.), delete

"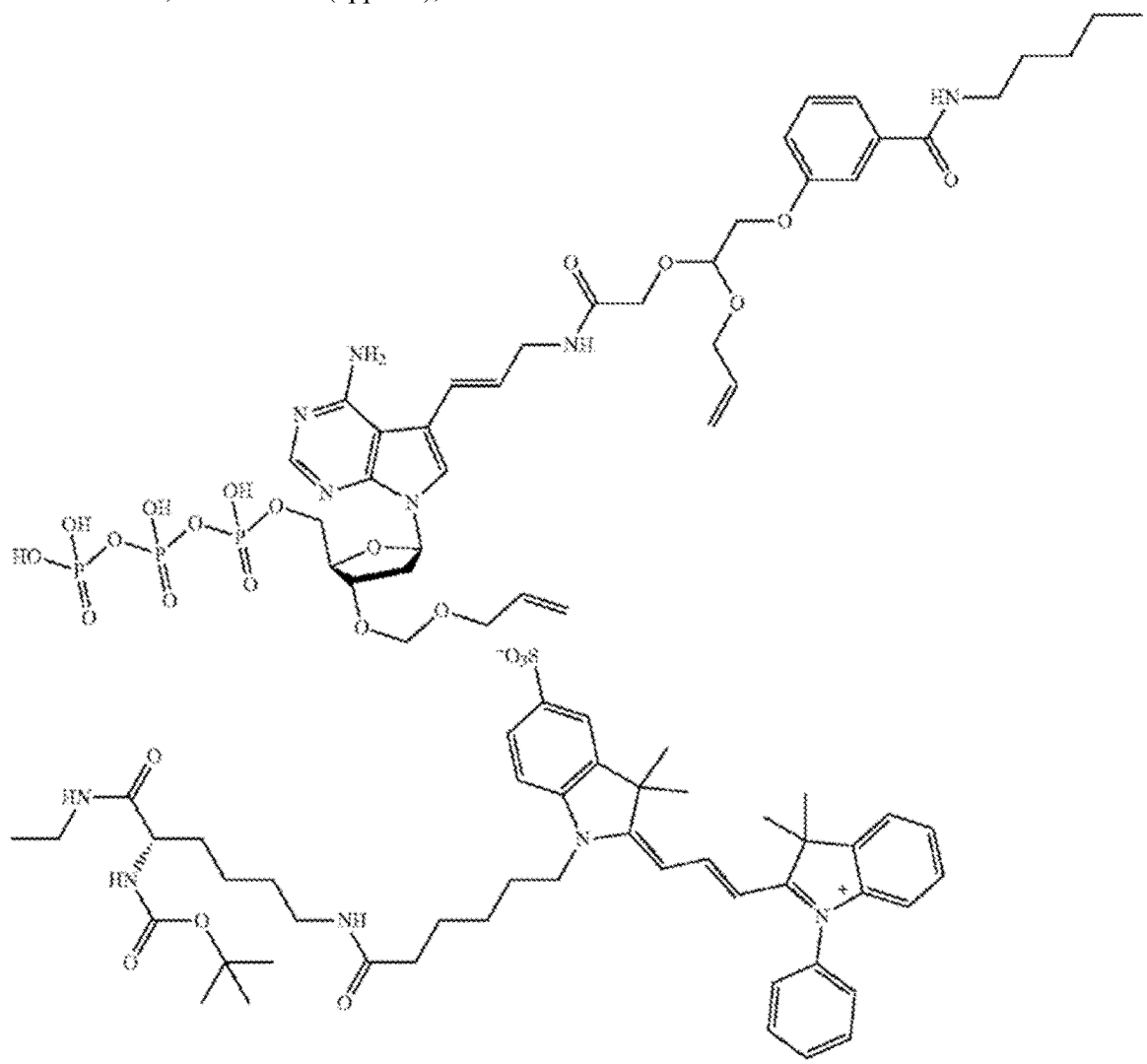"

and insert

--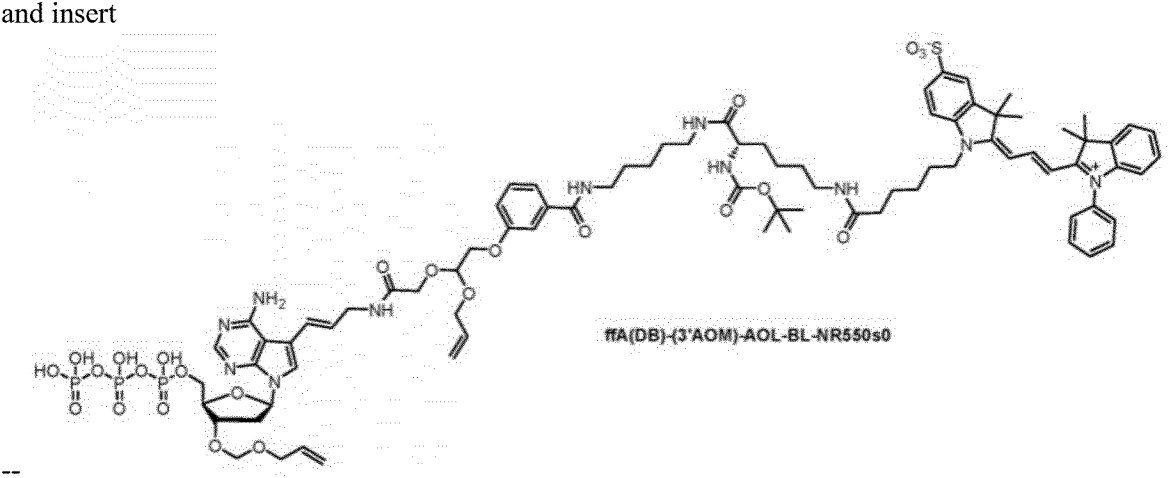--.

CERTIFICATE OF CORRECTION (continued)

Column 81, Line 19 (approx.), delete " 4.87 mol)." and insert -- 4.87 µmol). --.

Column 81, Line 44 (approx.), delete "5.6 mol)." and insert -- 5.6 µmol). --.

Columns 81-82, Lines 47-65 (approx.) and Column 84, Lines 1-23 (approx.), delete

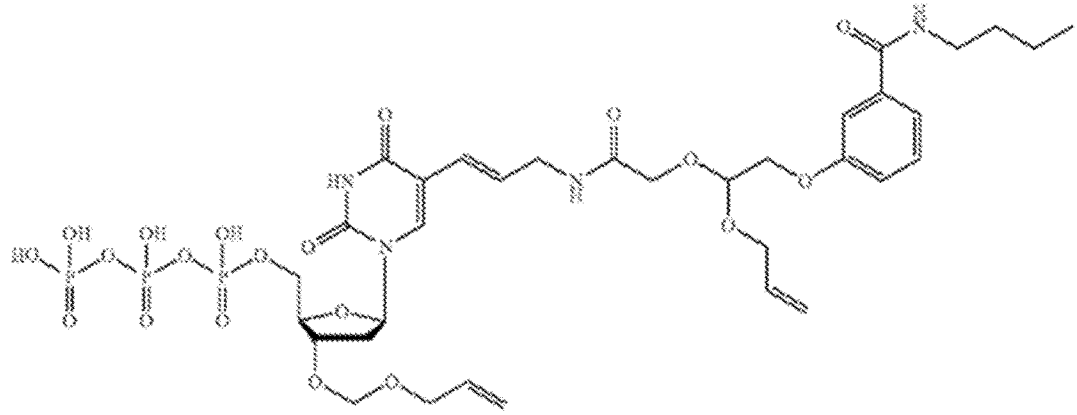

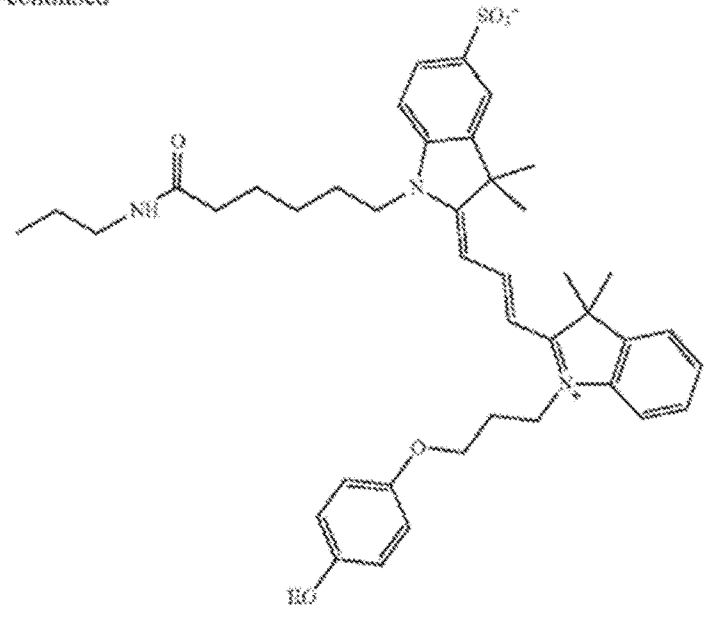

"

and insert

CERTIFICATE OF CORRECTION (continued)

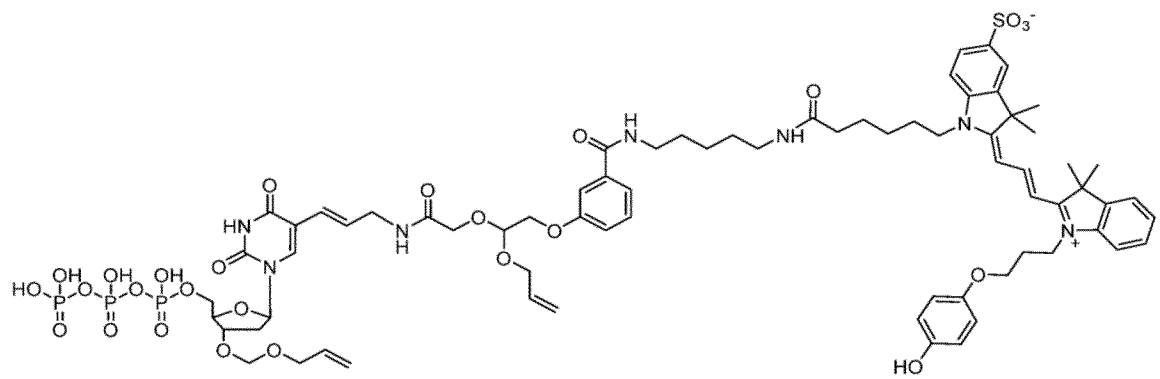

-- ffT(DB)-(3'AOM)-AOL-AF550POPOS0 --.

Column 83, Line 27 (approx.), delete "4.6 mol)." and insert -- 4.6 µmol). --.

In the Claims

Column 97, Line 54, in Claim 28, delete "—N+RR′-allyl," and insert -- —N⁺RR′-allyl, --.